US012667485B2

(12) United States Patent

Davis

(10) Patent No.: US 12,667,485 B2

(45) Date of Patent: Jun. 30, 2026

(54) EYE DROP PROPULSION DEVICE AND METHOD

(71) Applicant: Andrew Peter Davis, Bellevue, WA (US)

(72) Inventor: Andrew Peter Davis, Bellevue, WA (US)

( * ) Notice: Subject to any disclaimer, the term of this patent is extended or adjusted under 35 U.S.C. 154(b) by 0 days.

(21) Appl. No.: 19/284,385

(22) Filed: Jul. 29, 2025

(65) Prior Publication Data

US 2026/0144675 A1    May 28, 2026

Related U.S. Application Data

(60) Provisional application No. 63/726,308, filed on Nov. 28, 2024.

(51) Int. Cl.
A61F 9/00    (2006.01)

(52) U.S. Cl.
CPC .......... A61F 9/0026 (2013.01); A61F 9/0008 (2013.01); A61F 9/0017 (2013.01)

(58) Field of Classification Search
CPC ..... A61F 9/0008; A61F 9/0017; A61F 9/0026
See application file for complete search history.

(56) References Cited

U.S. PATENT DOCUMENTS

| | | | |
|---|---|---|---|
| 3,552,605 A | 1/1971 | Hein | |
| 4,111,200 A | 9/1978 | Sbarra et al. | |
| 4,392,590 A | 7/1983 | Hofmann-Igl | |

| | | | |
|---|---|---|---|
| 5,025,957 A | * | 6/1991 | Ranalletta ......... B05B 11/00444 |
| | | | 222/189.09 |
| 5,040,706 A | | 8/1991 | Davis et al. |
| 5,578,020 A | | 11/1996 | Mosley |
| 5,611,788 A | | 3/1997 | Marchment |
| 6,197,008 B1 | | 3/2001 | Hagele |
| 7,201,732 B2 | * | 4/2007 | Anderson ............. A61F 9/0008 |
| | | | 604/521 |

(Continued)

FOREIGN PATENT DOCUMENTS

| | | |
|---|---|---|
| CN | 105640768 A | 6/2016 |
| WO | 89/05166 | 6/1989 |

OTHER PUBLICATIONS

Nanodropper product information, retrieved from the Internet on Jul. 28, 2025, at https://nanodropper.com/features/, 1 page.

(Continued)

*Primary Examiner* — Guy K Townsend
(74) *Attorney, Agent, or Firm* — Lowe Graham Jones PLLC

(57) ABSTRACT

An eye drop propulsion device and method for propelling a drop of fluid towards an eye, including a compression chamber connected to a container configured to retain fluid, a dispenser aperture connected to the compression chamber and configured to be selectively occluded or not occluded, and a compressor configured to alter pressure in the compression chamber such that when the compressor is activated when the dispenser aperture is occluded, air is forced to flow from the compression chamber into the container, and when the compressor is deactivated, a vacuum is created in the compression chamber causing a portion of fluid in the container to flow into the compression chamber, and when the compressor is activated when the dispenser aperture is not occluded, a drop of fluid is propelled towards the eye.

11 Claims, 43 Drawing Sheets

(56)     References Cited

U.S. PATENT DOCUMENTS

| | | | |
|---|---|---|---|
| 7,527,613 B2 | 5/2009 | Gaynes | |
| 8,128,606 B2 * | 3/2012 | Anderson | A61F 9/0008 604/300 |
| 8,348,912 B2 * | 1/2013 | Rehkemper | A61F 9/0026 604/294 |
| D694,403 S | 11/2013 | Lensch | |
| D748,247 S | 1/2016 | MacRae et al. | |
| 9,610,192 B2 * | 4/2017 | Marx | A61F 9/0026 |
| 10,213,336 B2 * | 2/2019 | Lorch | A61F 9/0026 |
| D852,351 S | 6/2019 | Alvino et al. | |
| 10,383,790 B2 * | 8/2019 | Barkholt | A61F 9/0026 |
| 10,646,373 B2 | 5/2020 | Hunter et al. | |
| 10,758,407 B2 | 9/2020 | Mansfield | |
| 10,932,947 B2 | 3/2021 | Enemark | |
| 11,203,467 B2 | 12/2021 | Song et al. | |
| 11,213,424 B2 * | 1/2022 | Kinast | A61F 9/0026 |
| 11,679,028 B2 | 6/2023 | Quintana et al. | |
| 11,872,157 B2 | 1/2024 | Enemark | |
| D1,017,797 S | 3/2024 | Enemark | |
| 12,090,087 B2 * | 9/2024 | Ivri | A61J 1/1443 |
| 12,097,145 B2 * | 9/2024 | Quintana | A61J 1/1443 |
| 12,193,973 B2 * | 1/2025 | Jacobs | G08B 5/36 |
| 2005/0053501 A1 | 3/2005 | Akahori | |
| 2005/0077315 A1 | 4/2005 | Pavlu et al. | |
| 2005/0107755 A1 | 5/2005 | Berger et al. | |
| 2005/0131358 A1 * | 6/2005 | Skolik | A61M 11/02 604/181 |
| 2008/0233053 A1 * | 9/2008 | Gross | A61K 31/138 128/200.14 |
| 2009/0236374 A1 * | 9/2009 | Pardes | B05B 11/1032 222/494 |
| 2009/0259204 A1 * | 10/2009 | Galdeti | A61F 9/0026 222/173 |
| 2009/0272769 A1 | 11/2009 | Contreras et al. | |
| 2009/0318883 A1 * | 12/2009 | Sugahara | B05B 11/1052 222/105 |
| 2010/0022971 A1 | 1/2010 | Marx | |
| 2010/0286633 A1 * | 11/2010 | Marx | A61F 9/0026 604/296 |
| 2013/0006202 A1 * | 1/2013 | Marx | A61F 9/0026 604/300 |
| 2014/0213989 A1 * | 7/2014 | Kelly | A61F 9/0008 604/296 |
| 2014/0228783 A1 * | 8/2014 | Kraft | G07F 15/04 604/300 |
| 2014/0371688 A1 * | 12/2014 | Rezaei Abbassi | A61F 9/0026 604/290 |
| 2015/0051557 A1 | 2/2015 | Muir et al. | |
| 2017/0112664 A1 | 4/2017 | Ferkel | |
| 2017/0333250 A1 | 11/2017 | Foshee et al. | |
| 2018/0085251 A1 * | 3/2018 | Hunter | B05B 17/0661 |
| 2018/0092772 A1 * | 4/2018 | Mosalam | A61F 9/0008 |
| 2018/0193190 A1 * | 7/2018 | Ajaelo | G16H 20/13 |
| 2019/0224044 A1 | 7/2019 | Song et al. | |
| 2020/0055644 A1 * | 2/2020 | Höhm | B05B 11/04 |
| 2020/0197218 A1 | 6/2020 | Newell et al. | |
| 2020/0206031 A1 * | 7/2020 | Lim | A61F 9/0008 |
| 2023/0329905 A1 * | 10/2023 | Gale | A61F 9/0026 |
| 2023/0338188 A1 | 10/2023 | Kuwano | |

OTHER PUBLICATIONS

Office Action dated Dec. 22, 2017, in U.S. Appl. No. 14/386,516, filed Sep. 19, 2014, 12 pages.

Charters, L., "New RainDrop Dispenser Aid aims to simplify use of single-use eye drops," Ophthalmology Times, Jul. 15, 2025, Rain Eye Drops LLC, retrieved from the Internet on Dec. 24, 2025, at https://www.ophthalmologytimes.com/view/new-raindrop-dispenser-aid-aims-to-simplify-use-of-single-use-eye-drops, 3 pages.

Ophthalmic Squeeze Dispenser (OSD) Technology Platform, Multidose Systems, Eye Care Dropper product information, Aptar, retrieved from the Internet at https://aptar.com/products/pharmaceutical/ophthalmic-squeeze-dispenser-technology-platform/ on Aug. 4, 2025, 1 page.

AutoDrop(R) & AutoSqueeze(TM) product information, Owen Mumford, retrieved from the Internet through owenmumford.com and Amazon.com as "OP 6000 Autodrop Eye Guide" and "Peermax Drop Smart Eye Drop Guide," on Aug. 4, 2025, 5 pages.

Horrom, "New device invented by VA nurse makes using eyedrops easier," DropEase product information, VA News, Mar. 10, 2022, retrieved from the Internet at https://news.va.gov/101006/new-device-invented-by-va-nurse-makes-using-eyedrops-easier/, on Aug. 4, 2025, 1 page.

Eye Drop Helper—with Free Travel Pouch product information, XactDrop, retrieved from the Internet through Amazon.com on Aug. 4, 2025, 2 pages.

EziDrops Eye Drop Applicator product information, EziDrops, retrieved from the Internet through Amazon.com, on Aug. 4, 2025, 2 pages.

GentleDrop product information, GentleDrop, retrieved from the Internet through Amazon.com on Aug. 4, 2025, 1 page.

Optejet(R) Technology topical eye medication dispenser product information, Eyenovia, retrieved from the Internet at https://eyenovia.com/optejet-technology/ on Aug. 4, 2025, 2 pages.

Precision Dropper product information, Precision Dropper, retrieved from the Internet through Amazon.com, on Aug. 4, 2025, 4 pages.

\* cited by examiner

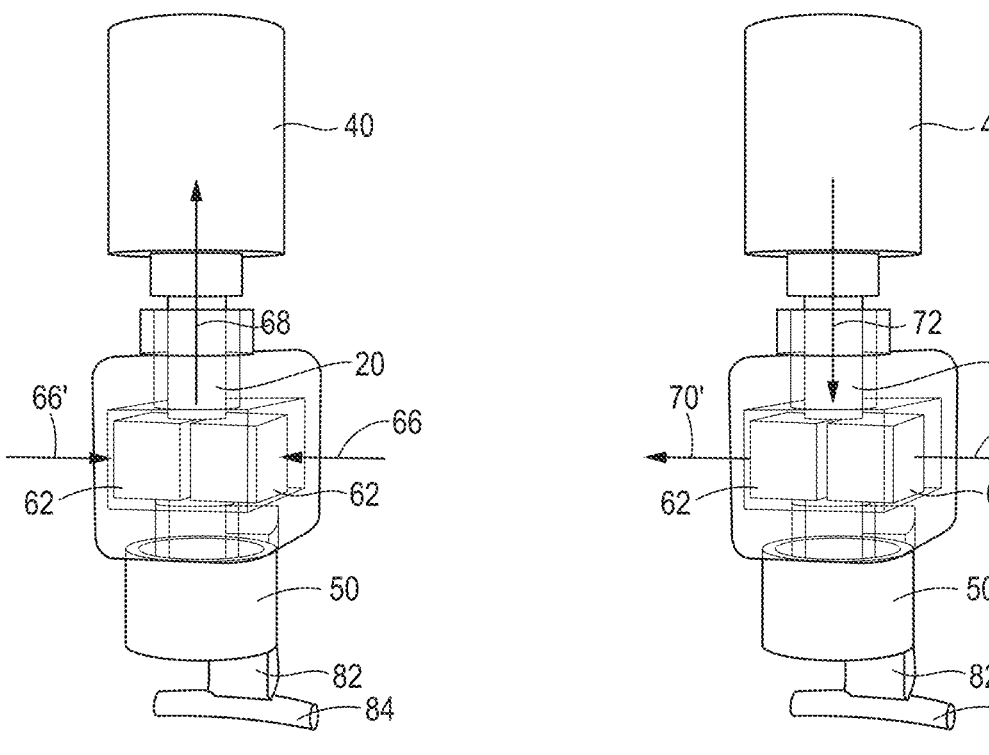
*FIG. 5A*                    *FIG. 5B*
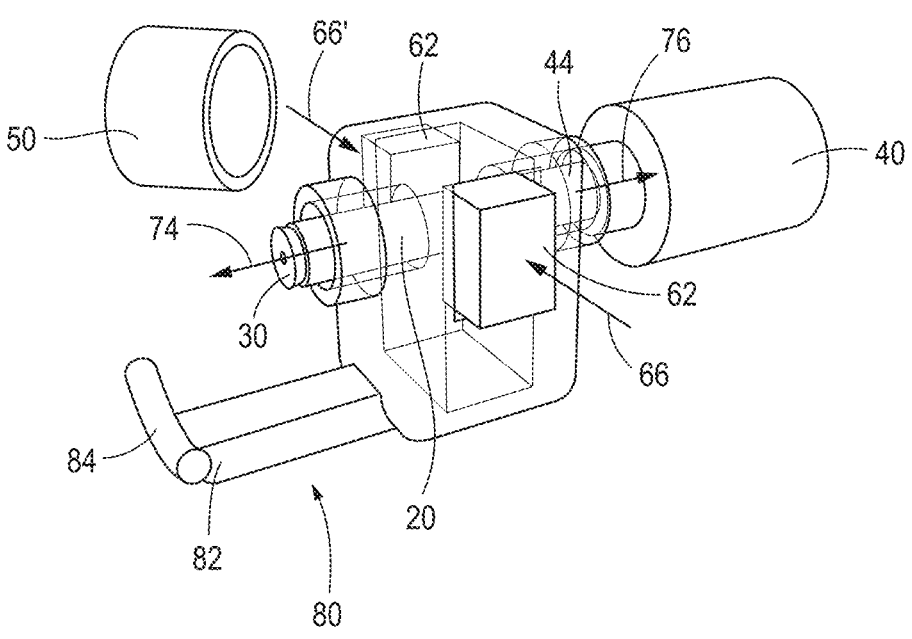
*FIG. 5C*

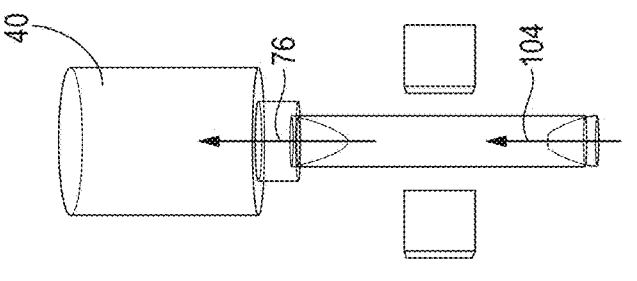
*FIG. 8E*
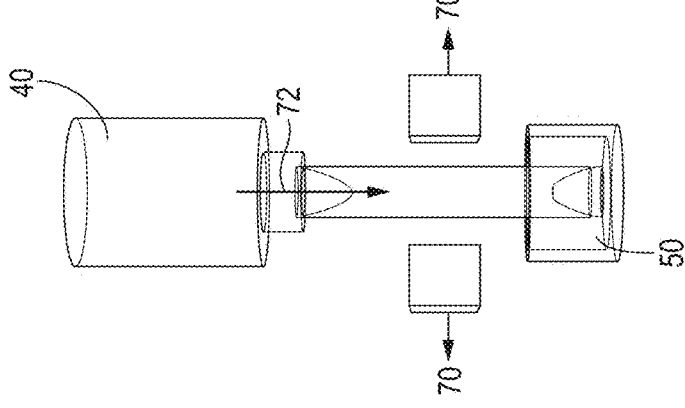
*FIG. 8D*
*FIG. 8C*
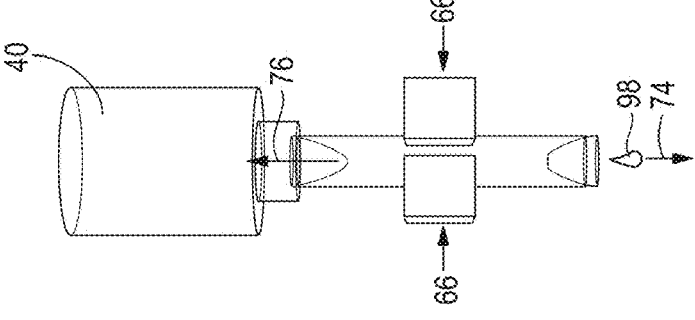
*FIG. 8B*
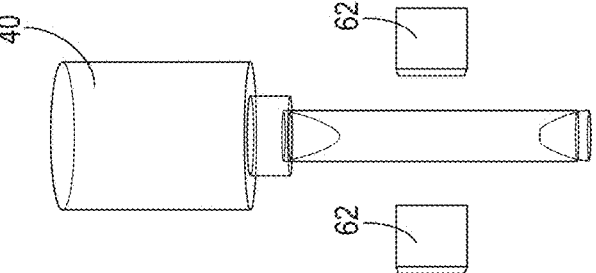
*FIG. 8A*

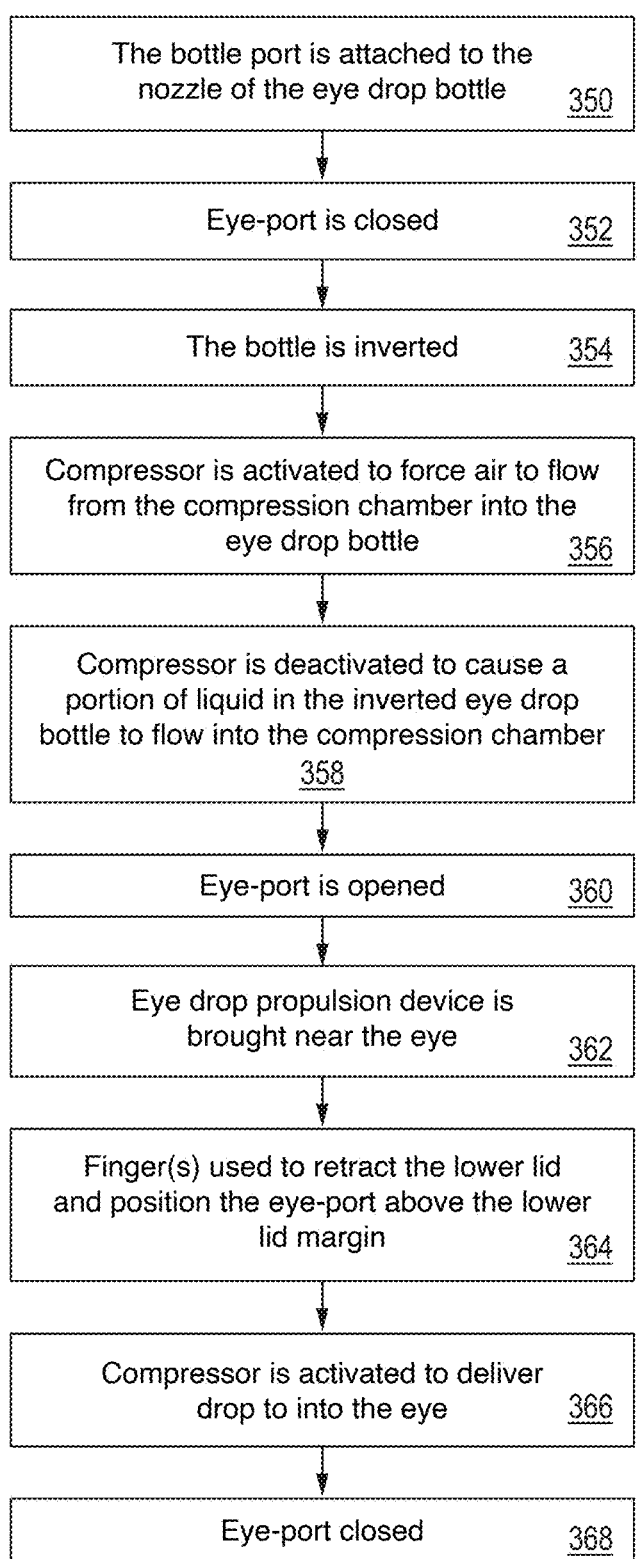

The bottle port is attached to the
nozzle of the eye drop bottle          350

Eye-port is closed          352

The bottle is inverted          354

Compressor is activated to force air to flow
from the compression chamber into the
eye drop bottle          356

Compressor is deactivated to cause a
portion of liquid in the inverted eye drop
bottle to flow into the compression chamber
358

Eye-port is opened          360

Eye drop propulsion device is
brought near the eye          362

Finger(s) used to retract the lower lid
and position the eye-port above the lower
lid margin          364

Compressor is activated to deliver
drop to into the eye          366

Eye-port closed          368

*FIG. 10B*

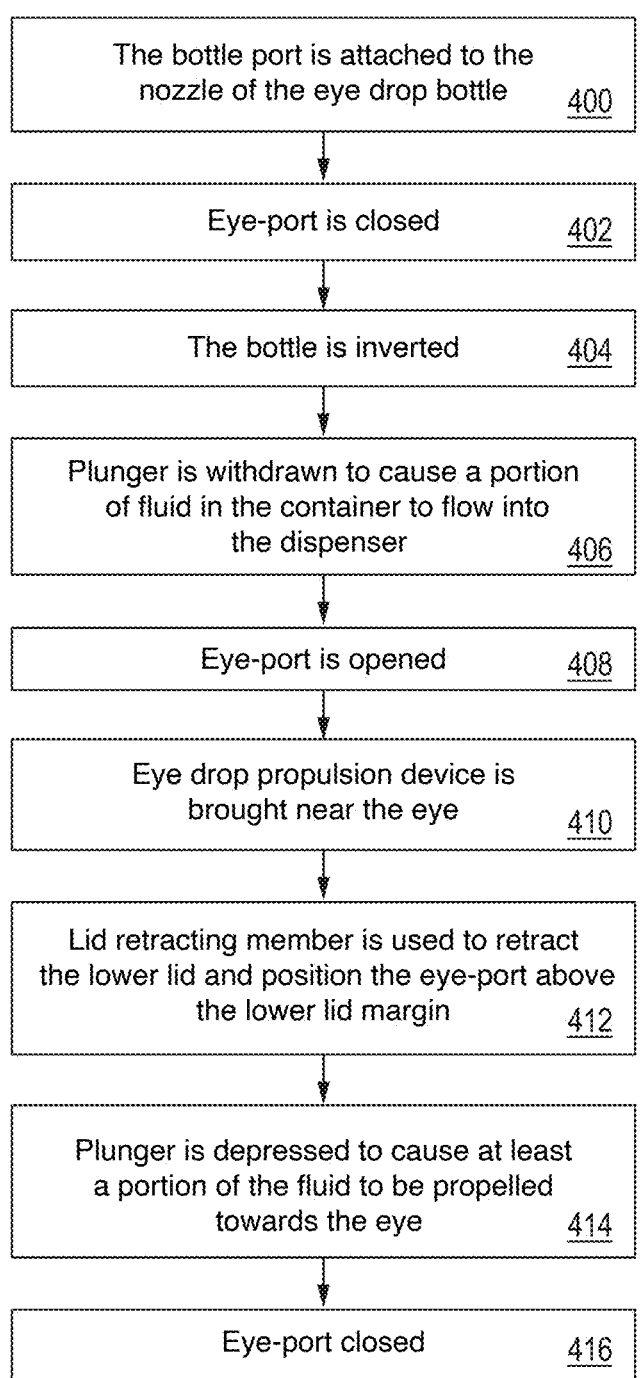

The bottle port is attached to the
nozzle of the eye drop bottle          400

Eye-port is closed          402

The bottle is inverted          404

Plunger is withdrawn to cause a portion
of fluid in the container to flow into
the dispenser          406

Eye-port is opened          408

Eye drop propulsion device is
brought near the eye          410

Lid retracting member is used to retract
the lower lid and position the eye-port above
the lower lid margin          412

Plunger is depressed to cause at least
a portion of the fluid to be propelled
towards the eye          414

Eye-port closed          416

*FIG. 11A*

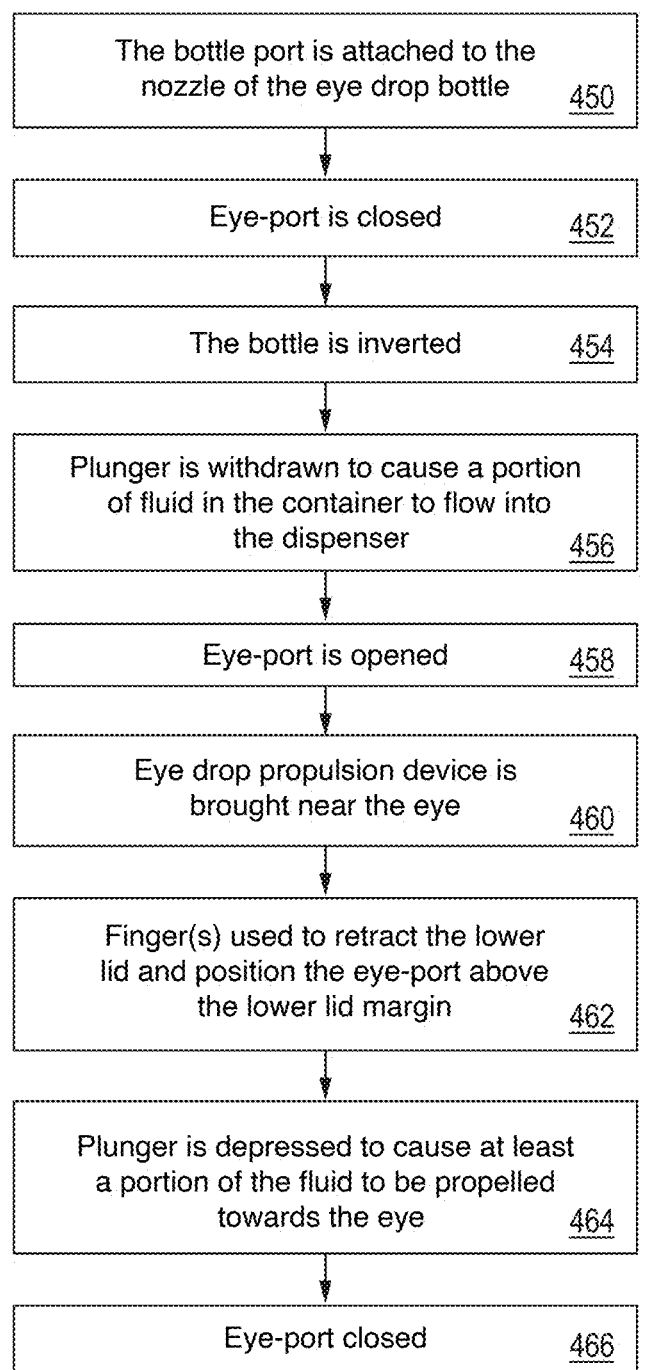

The bottle port is attached to the nozzle of the eye drop bottle    450

Eye-port is closed    452

The bottle is inverted    454

Plunger is withdrawn to cause a portion of fluid in the container to flow into the dispenser    456

Eye-port is opened    458

Eye drop propulsion device is brought near the eye    460

Finger(s) used to retract the lower lid and position the eye-port above the lower lid margin    462

Plunger is depressed to cause at least a portion of the fluid to be propelled towards the eye    464

Eye-port closed    466

*FIG. 11B*

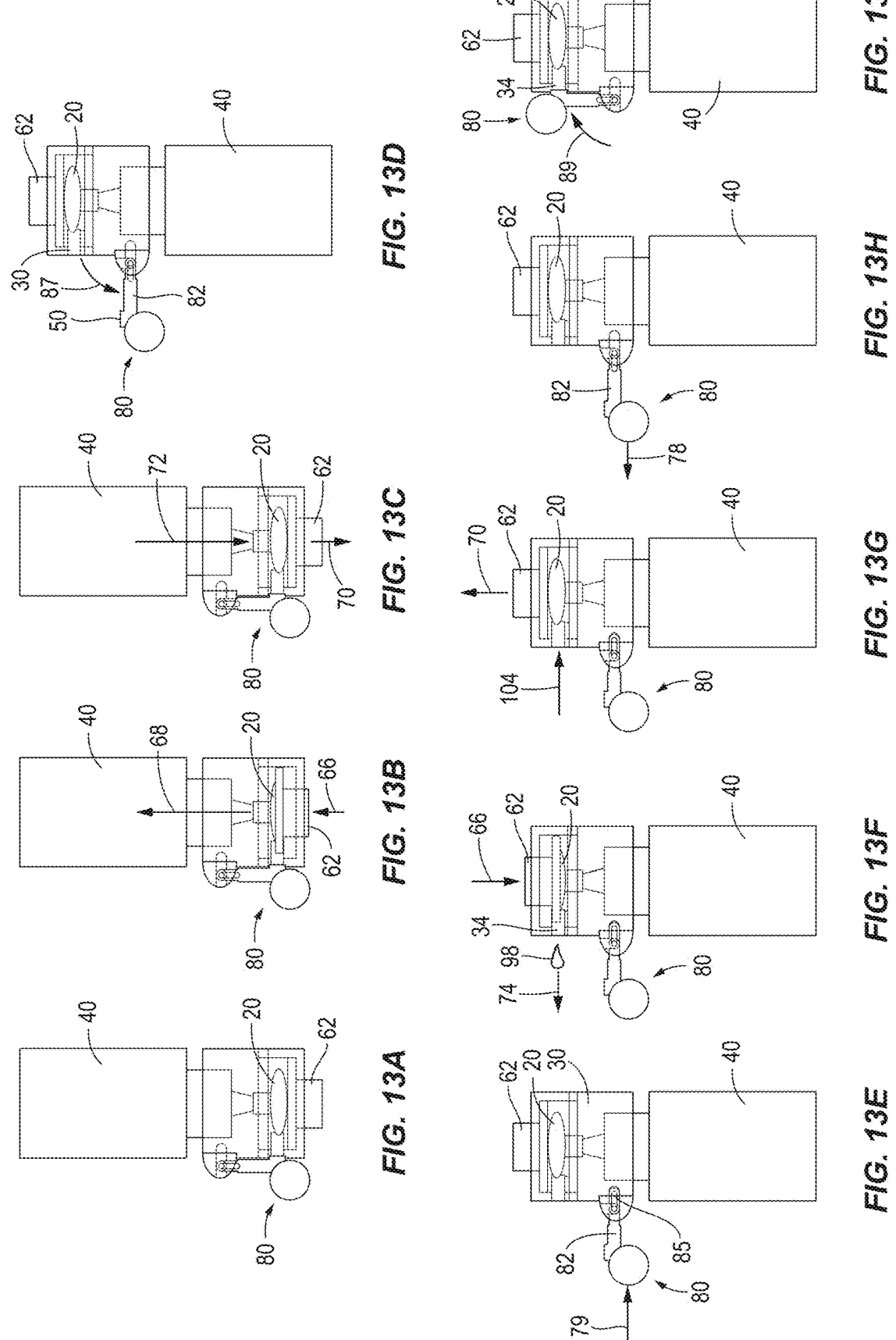

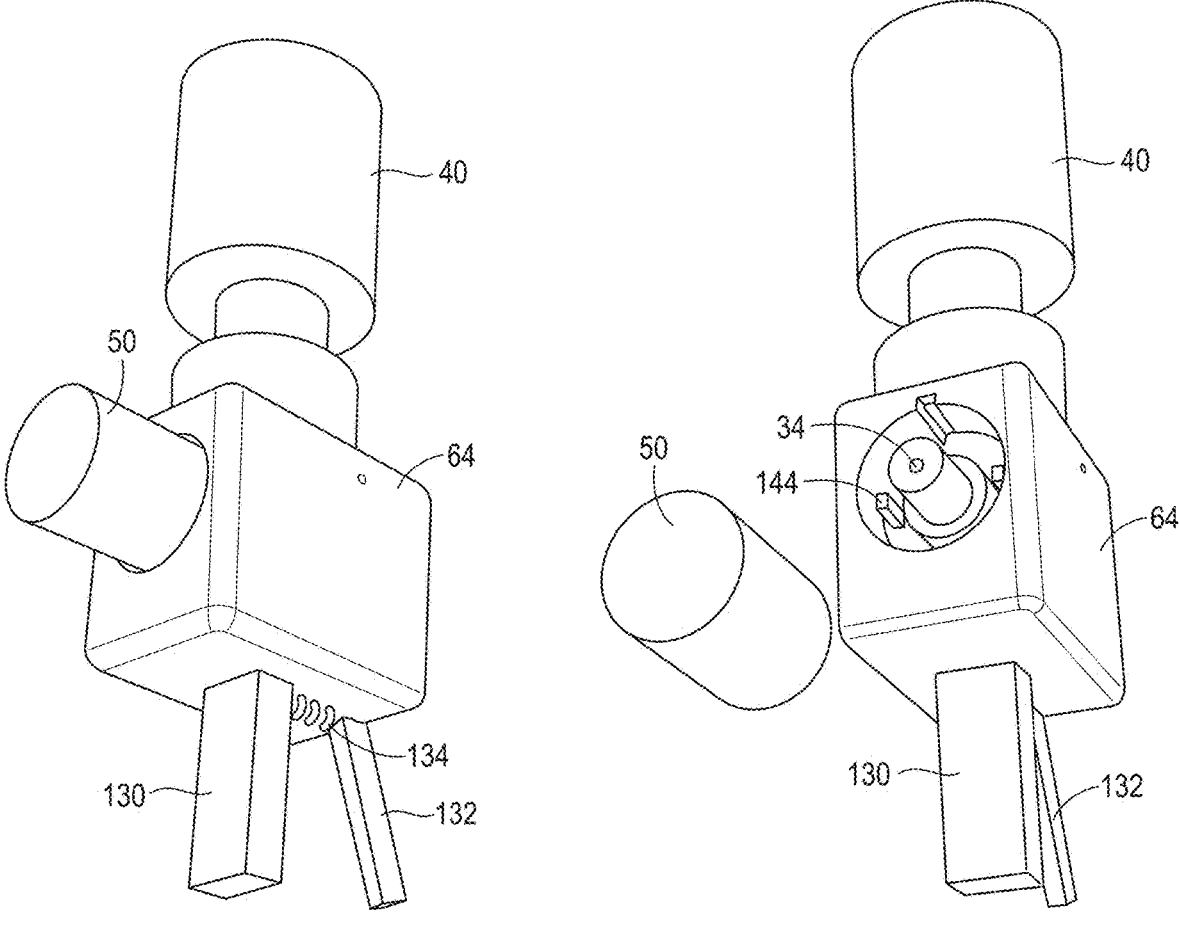
*FIG. 19A*                    *FIG. 19B*

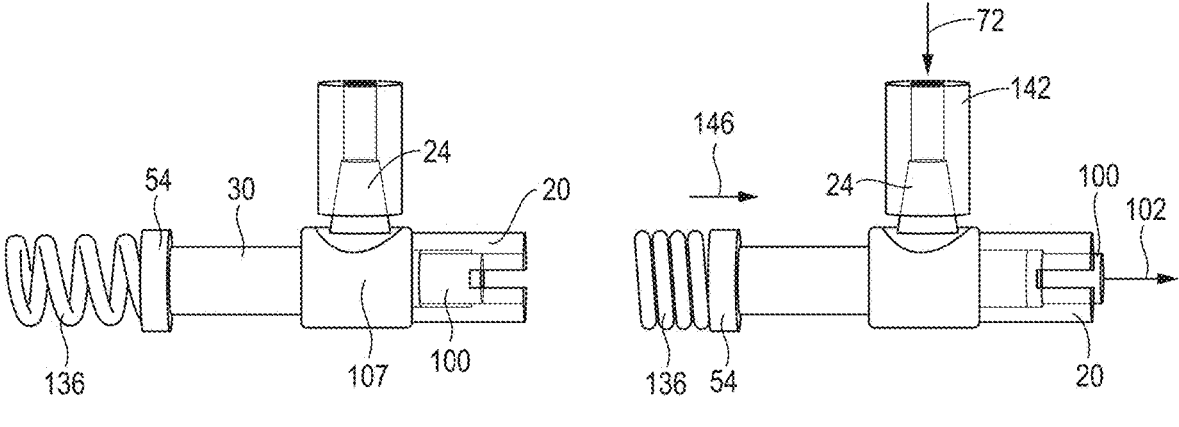
FIG. 20A                              FIG. 20B
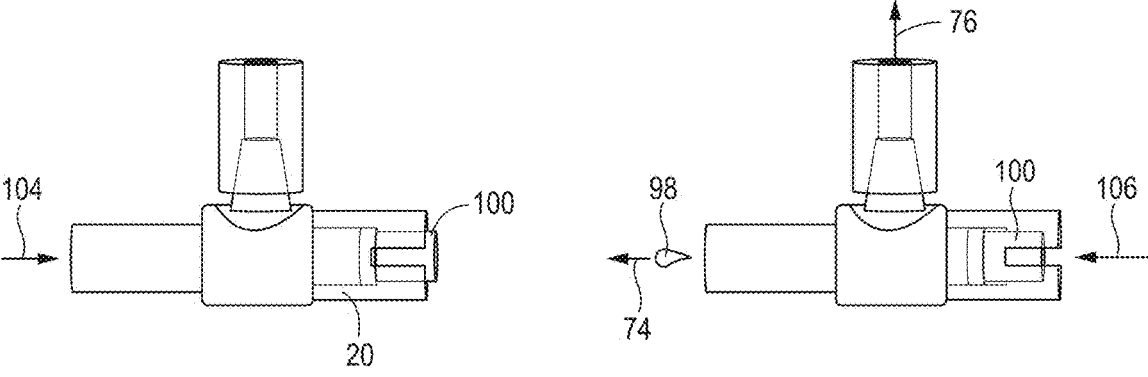
FIG. 20C                              FIG. 20D

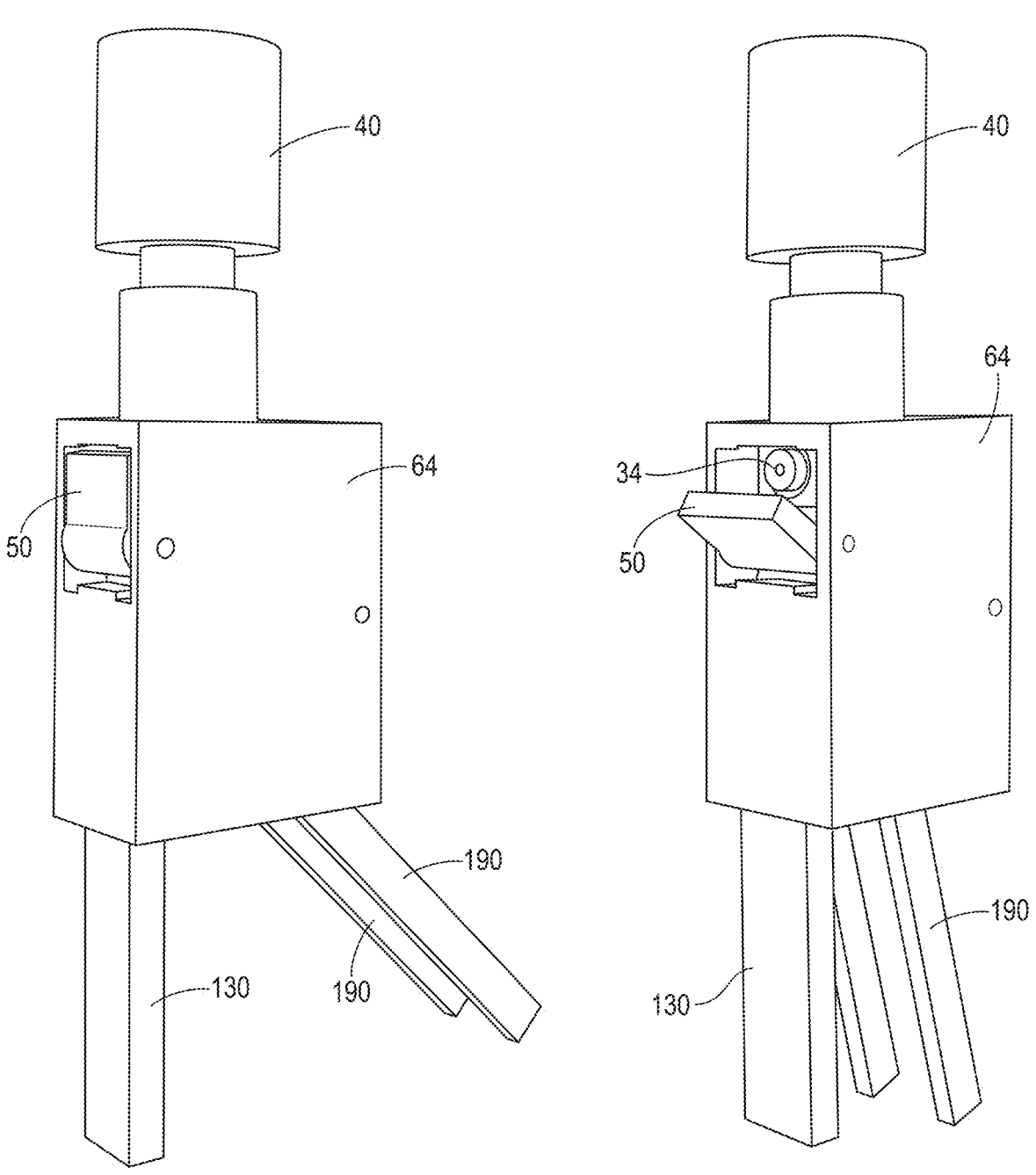
*FIG. 25A*          *FIG. 25B*

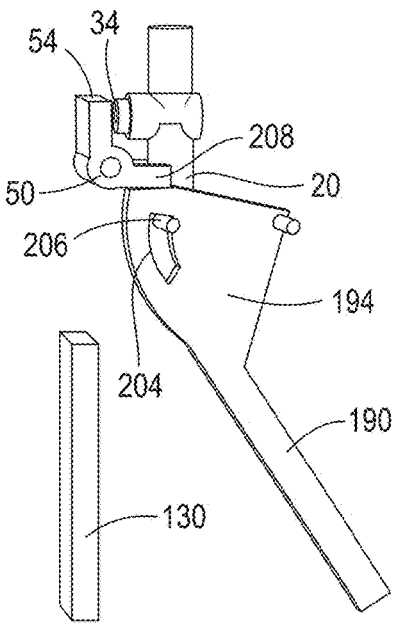
FIG. 26A
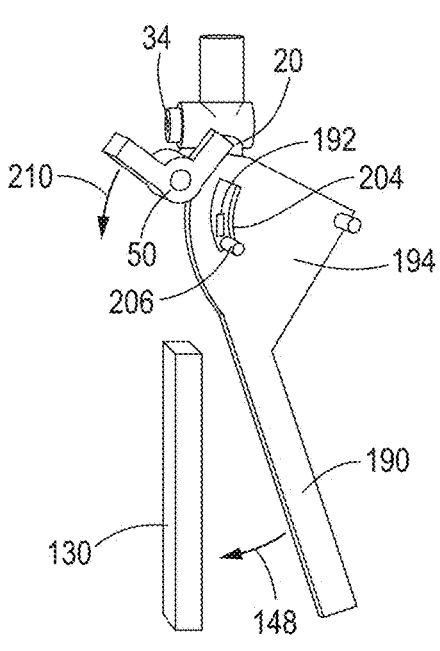
FIG. 26C
FIG. 26B
FIG. 26D
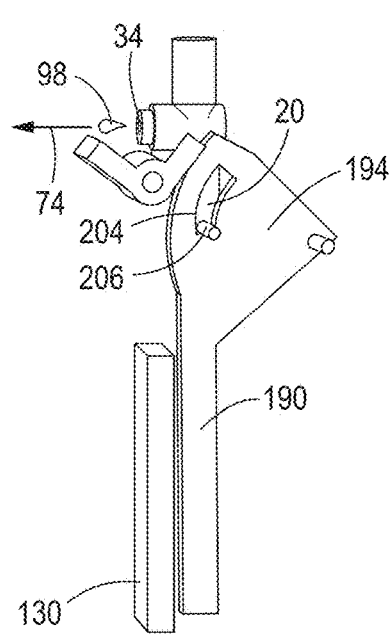

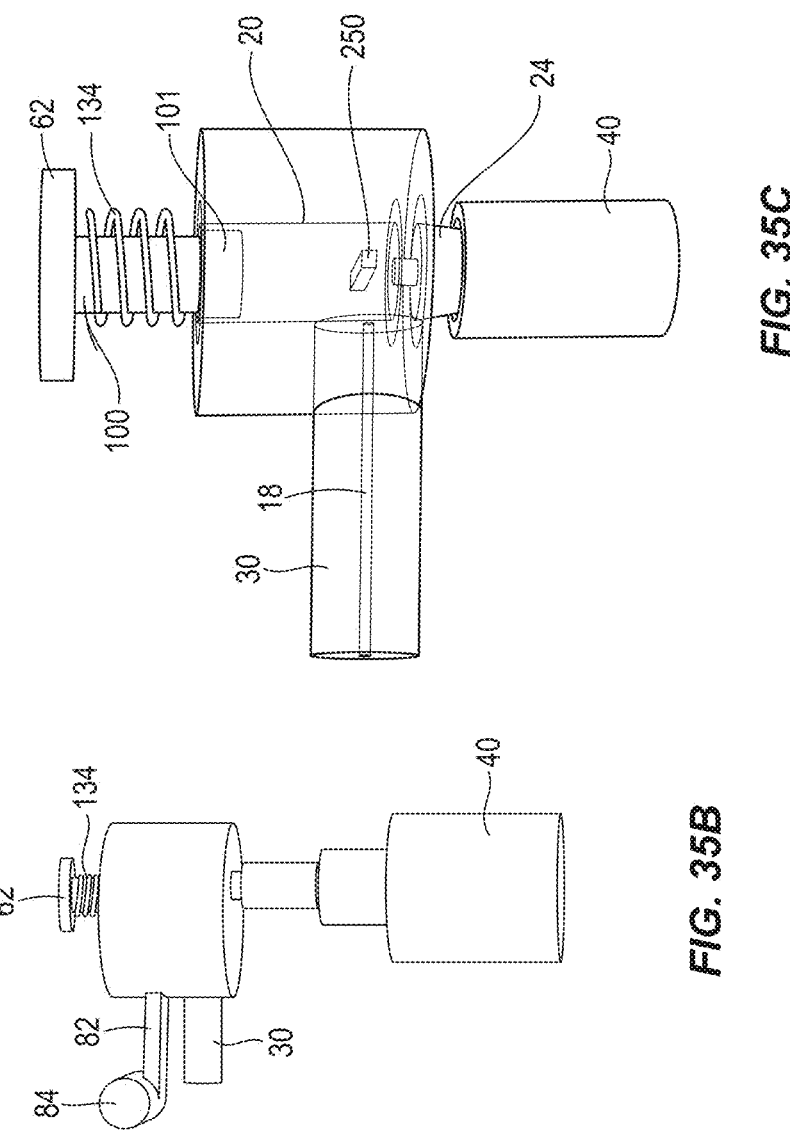
*FIG. 35C*
*FIG. 35B*
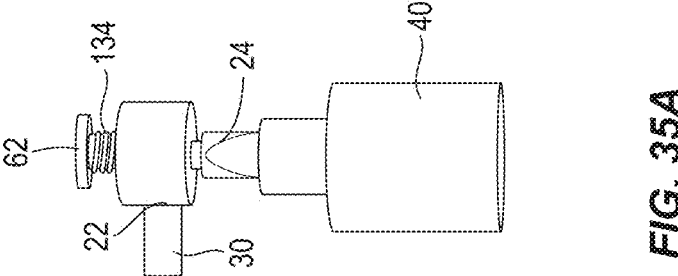
*FIG. 35A*

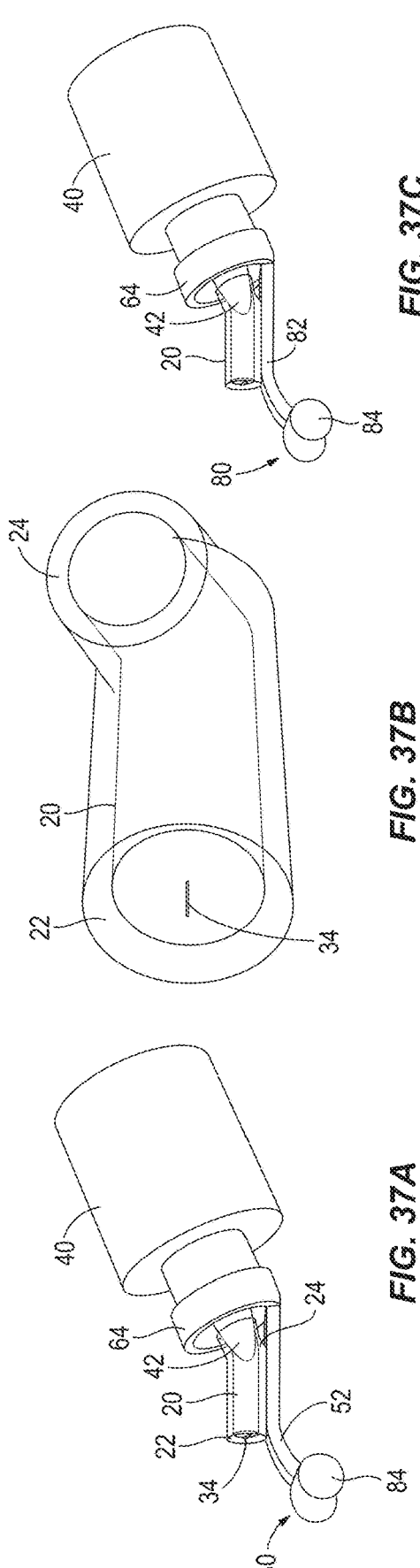
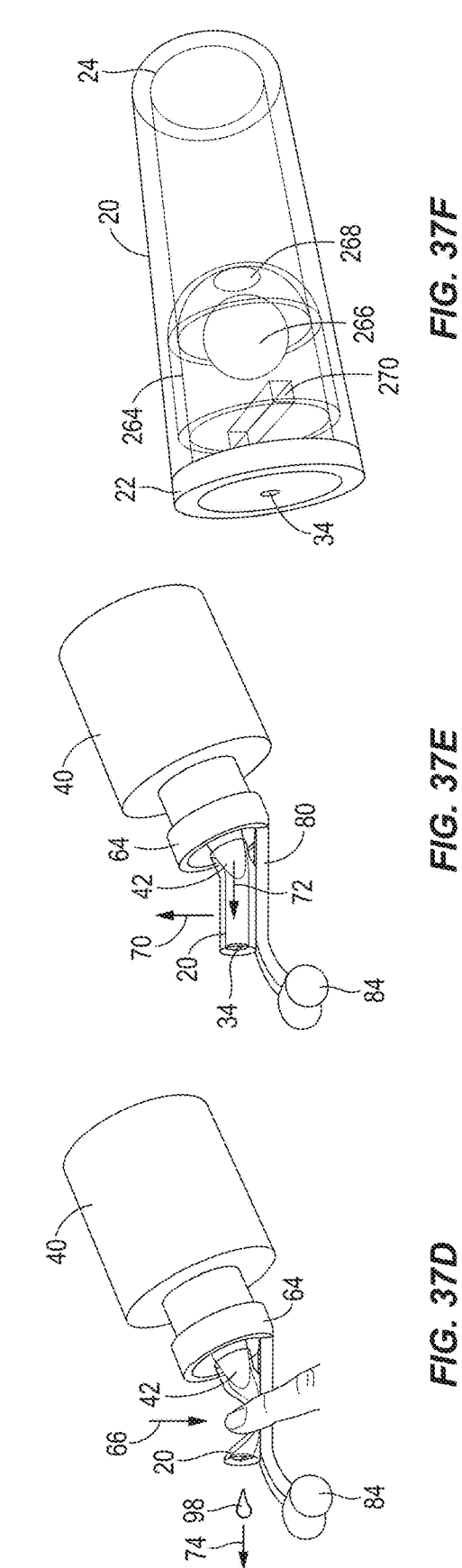
*FIG. 37C*
*FIG. 37B*
*FIG. 37A*
*FIG. 37F*
*FIG. 37E*
*FIG. 37D*

EYE DROP PROPULSION DEVICE AND METHOD

PRIORITY CLAIM

This application claims the benefit of priority from U.S. Provisional Patent Application No. 63/726,308, filed Nov. 28, 2024, the contents of which are incorporated herein by reference in their entirety.

BACKGROUND OF THE INVENTION

The self-administration of eye drops can be particularly challenging. Targeting one's delicate, sensitive eye, even to alleviate pain or discomfort, often causes stress and anxiety. Often the elderly can have difficulty squeezing the bottle, especially with arthritis. Holding the bottle steady near the eye can be difficult if there is any type of tremor. Tilting the head back is often necessary to deliver the drop, making it difficult for anyone with neck problems and making even more difficult to aim the drop or hold the bottle steady. Using a mirror can be difficult, especially if there is visual impairment or difficulty in getting close enough to a mirror. There is significant wasting of the eye drops due to missing the eye, and then having to put in multiple drops to ensure that at least one drop got in. Drops that miss the eye and land on the skin can cause significant irritation of the skin. Holding the bottle, tilting the head, holding the eye open, positioning a mirror, and squeezing the bottle can be a daunting task for many individuals.

The are many products on the market to help make giving eye drops easier. Many involve a bottle holder to make it easier to squeeze the bottle, and a guide to hold the bottle above the eye while the head is tilted back. Other products let the bottle rest on the bridge of the nose. Some devices attempt to provide a spray or mist to apply multiple drops in the hope that a least some will reach the eye target. Each of these existing products or methods continue the same disadvantages identified above, among others. The ideal device is one that allows application of a drop of fluid and does not require the user to have to squeeze a stiff bottle, tilt their head back, or use a mirror.

SUMMARY OF THE INVENTION

The present invention allows a patient to self-administer an eye drop with much greater ease, even with their eyes closed or for a patient who is blind. In one embodiment, a compression chamber assembly with at least two openings, one opening (bottle-port) configured to attach to the nozzle of an eye drop bottle in a watertight fashion and a second opening (eye-port) configured to point towards the eye, joins with one or more compressors configured to enable compression and decompression of the compression chamber, which is used to control pressure within the compression chamber. The bottle-port securely attaches to a nozzle of the eye drop bottle in a watertight fashion and is configured to adapt to the varying dimensions of the many different available eye drop bottles. The eye-port has an aperture configured to allow a drop of fluid to be propelled to the eye and an occluding member that is able to occlude both inflow and outflow through the aperture. The compression chamber includes a reservoir to hold fluid from the eye drop bottle. In operation, the combination of the compression chamber and compressor(s) (a) generates sufficient pressure in the compression chamber when it is compressed and the eye-port is not occluded (i.e., not blocked, obstructed or closed off) such that a drop of fluid from the reservoir is propelled through the eye-port with sufficient velocity and trajectory to the eye; (b) generates sufficient negative pressure in the compression chamber relative to the pressure in the eye drop bottle when the compression chamber is decompressed and the eye-port occluded (i.e., blocked, obstructed or closed off) such that fluid flows from the tilted or inverted eye drop bottle through the bottle-port and into the reservoir of the compression chamber; and (c) prevents a persistent vacuum in the eye drop bottle by either injecting air into the bottle before the withdrawal of fluid or by allowing the eye drop bottle to vent after the withdrawal of fluid.

In operation, the invention (a) delivers a drop through the eye-port when the compression chamber is compressed and when the eye-port is not occluded, propelling the drop towards the eye with a sufficient velocity and trajectory to reach the eye with the patient's head in a substantially upright position; (b) withdraws a sufficient volume of fluid from the eye drop bottle through the bottle-port into the reservoir of the compression chamber when the eye-port is occluded and the compression chamber is decompressed with the eye drop bottle in a tilted or inverted position; and (c) repeats the compression and decompression cycles without creating a persistent vacuum in the eye drop bottle.

In one embodiment, an eye drop propulsion device for propelling a drop of fluid towards an eye includes a compression chamber, a container configured to retain and communicate fluid into the compression chamber, a dispenser aperture configured to be selectively occluded or not occluded, and a compressor configured to alter pressure in the compression chamber such that when the compressor is activated when the dispenser aperture is occluded, air is forced to flow from the compression chamber into the container, and when the compressor is deactivated, a vacuum is created in the compression chamber causing a portion of fluid in the container to flow into the compression chamber, and when the compressor is activated when the dispenser aperture is not occluded, a drop of the fluid is propelled towards the eye. In alternative embodiments, a reservoir connected to the compression chamber and configured to retain fluid and communicate that fluid towards the dispenser aperture. In other embodiments, the container is oriented such that it is inverted before the compressor is deactivated when the dispenser aperture is occluded. In yet other embodiments, the compressor is sized relative to the compression chamber to generate a drop of fluid propelled towards the eye. In other embodiments, the compressor is a user member applying pressure against the compression chamber, for example, a person using their finger(s) to squeeze the compression chamber. In yet other embodiments, the drop is propelled towards the eye without the aid of gravity, for example, in a generally non-vertical alignment that does not require tipping the head back or the use of gravity to release a drop in a generally downward direction towards the eye. In other embodiments, a cover is used to selectively occlude the dispenser aperture. In yet other embodiments, a retractor is used to support the propulsion device aligned with the eye before the drop of the fluid is propelled towards the eye. In other embodiments, a retractor is used to retract a lower lid of the eye before the drop of the fluid is propelled towards the eye. In alternative embodiments, the drop of fluid is propelled towards the eye with sufficient velocity to reach the eye. In alternative embodiments, at least one of the compression chamber, compressor, and dispenser aperture are sized to allow the drop of fluid to be propelled.

In one embodiment, a method of propelling a drop of fluid towards an eye includes the steps of connecting a container of fluid to a compression chamber having a dispenser aperture configured to be selectively occluded or not occluded, with the dispenser aperture occluded, activating a compressor configured to alter pressure in the compression chamber to force air to flow from the compression chamber into the container and deactivating the compressor to cause a portion of fluid in the container to flow into the compression chamber, and with the dispenser aperture not occluded, activating the compressor to propel a drop of fluid from the dispenser aperture towards the eye. In an alternative embodiment, the method further includes inverting the container before deactivating the compressor with the dispenser aperture occluded. In other embodiments, the method includes retracting a lower lid of the eye before activating the compressor to propel the drop of fluid from the dispenser aperture towards the eye. In yet other embodiments, the method includes aligning the dispenser aperture above a lower lid of the eye before activating the compressor to propel the drop of fluid from the dispenser aperture towards the eye. In other embodiments, the method includes using a second compressor to propel the drop of fluid from the dispenser aperture towards the eye. In alternative embodiments, at least one of the compression chamber, compressor, and dispenser aperture are sized to allow a drop of fluid to be propelled.

In a different embodiment, an eye drop propulsion device for propelling a drop of fluid towards an eye includes a dispenser aperture configured to be selectively occluded or not occluded, a container configured to retain and communicate fluid into the compression chamber, and a compression chamber connected to the dispenser and having a plunger configured to alter pressure in the compression chamber such that when the plunger is withdrawn from the compression chamber when the dispenser aperture is occluded, the vacuum created in the compression chamber causes a portion of fluid in the container to flow into the compression chamber, and when the plunger is depressed into the compression chamber when the dispenser aperture is not occluded, a drop of the fluid is propelled towards the eye. In alternative embodiments, a reservoir connected to the compression chamber and configured to retain fluid and communicate that fluid towards the dispenser aperture. In other embodiments, the container is oriented such that it is inverted before the compressor is deactivated when the dispenser aperture is occluded. In yet other embodiments, the compressor is sized relative to the compression chamber to generate a drop of fluid propelled towards the eye. In other embodiments, the compressor is a user member applying pressure against the compression chamber, for example, a person using their finger(s) to squeeze the compression chamber. In yet other embodiments, the drop is propelled towards the eye without the aid of gravity, for example, in a generally non-vertical alignment that does not require tipping the head back or the use of gravity to release a drop in a generally downward direction towards the eye. In other embodiments, a cover is used to selectively occlude the dispenser aperture. In yet other embodiments, a retractor is used to support the propulsion device aligned with the eye before the drop of the fluid is propelled towards the eye. In other embodiments, a retractor is used to retract a lower lid of the eye before the drop of the fluid is propelled towards the eye. In other embodiments, the drop of fluid is propelled towards the eye with sufficient velocity to reach the eye. In alternative embodiments, at least one of the compression chamber, compressor, and dispenser aperture are sized to allow a drop of fluid to be propelled.

In a different embodiment, a method of propelling a drop of fluid towards an eye includes the steps of connecting a container of fluid to a compression chamber having a dispenser aperture configured to be selectively occluded or not occluded and sized to allow a drop of fluid to be propelled, with the dispenser aperture occluded, withdrawing a plunger configured to alter pressure in the compression chamber to cause a portion of fluid in the container to flow into the compression chamber, and with the dispenser aperture not occluded, depressing the plunger to propel a drop of fluid from the dispenser aperture towards the eye. In an alternative embodiment, the method further includes inverting the container before withdrawing the plunger with the dispenser aperture occluded. In other embodiments, the method further includes retracting a lower lid of the eye before activating the compressor to propel the drop of fluid from the dispenser aperture towards the eye. In yet other embodiments, the method includes aligning the dispenser aperture above a lower lid of the eye before activating the compressor to propel the drop of fluid from the dispenser aperture towards the eye. In alternative embodiments, at least one of the compression chamber, compressor, and dispenser aperture are sized to allow a drop of fluid to be propelled.

In a different embodiment, an eye drop propulsion device for propelling a drop of fluid towards an eye includes a compression chamber, a container configured to retain and communicate fluid into the compression chamber, a dispenser aperture configured to be occluded or not occluded, and a compressor configured to alter pressure in the compression chamber such that when the compressor is activated and the dispenser aperture is not occluded, a drop of fluid is propelled towards the eye, and when the compressor is deactivated and the dispenser aperture is occluded, a vacuum is created in the compression chamber causing a portion of fluid in the container to flow into the compression chamber. In alternative embodiments, a reservoir is connected to the compression chamber and configured to retain fluid and communicate that fluid towards the dispenser aperture. In other embodiments, the compressor is sized relative to the compression chamber to generate a drop of fluid propelled towards the eye. In yet other embodiments, the compressor is a user member applying pressure against the compression chamber. In alternative embodiments, the drop is propelled towards the eye without the aid of gravity. In other embodiments, a retractor is used to support the propulsion device aligned with the eye before the drop of the fluid is propelled towards the eye. In yet other embodiments, a retractor is used to retract a lower lid of the eye before the drop of the fluid is propelled towards the eye. In alternative embodiments, the drop of fluid is propelled towards the eye with sufficient velocity to reach the eye. In other embodiments, at least one of the compression chamber, compressor, and dispenser aperture are sized to allow the drop of fluid to be propelled. In yet other embodiments, the device further includes a vacuum release aperture in the compression chamber configured to selectively alleviate a vacuum within the container.

In a different embodiment, an eye drop propulsion device for propelling a drop of fluid towards an eye includes a compression chamber, a container configured to retain and communicate fluid into the compression chamber, and a dispenser aperture connected to the compression chamber, wherein the dispenser aperture is configured to allow fluid sufficient to form at least a drop to be added to the compression chamber from the container without fluid exiting the dispenser aperture, and the dispenser aperture is configured to allow the at least a drop of fluid to be propelled towards the eye when a compressor configured to alter pressure in the compression chamber is activated. In alternative embodiments, the compressor is sized relative to the compression chamber to generate the drop of fluid propelled towards the eye. In other embodiments, the drop is propelled towards the eye without the aid of gravity. In yet other embodiments, a retractor is used to support the propulsion device aligned with the eye before the drop of the fluid is propelled towards the eye. In alternative embodiments, a retractor is used to retract a lower lid of the eye before the drop of the fluid is propelled towards the eye. In other embodiments, the drop of fluid is propelled towards the eye with sufficient velocity to reach the eye. In yet other embodiments, the dispenser aperture is configured to be positioned above a level of fluid sufficient to form the at least a drop when fluid is added to the compression chamber from the container, and positioned below the level of fluid sufficient to form the at least a drop when the compressor is activated.

BRIEF DESCRIPTION OF THE DRAWINGS

Preferred and alternative examples of the present invention are described in detail below with reference to the following drawings.

FIGS. 5A-5C show the operation of a variation of the eye drop propulsion device of FIGS. 3-4.

FIGS. 8A-8E show the operation of the eye drop propulsion device of FIGS. 7A-7F.

FIG. 10B shows a flowchart detailing one method of using the present invention having a user member as the retractor.

FIG. 11A shows a flowchart detailing one method of using the present invention having a plunger compressor assembly and a retractor assembly.

FIG. 11B shows a flowchart detailing one method of using the present invention having a plunger compressor assembly and a user member as the retractor.

FIGS. 13A-13I show the operation of the eye drop propulsion device of FIG. 12 with a modified retractor assembly.

FIGS. 19A-19B show an eye drop propulsion device according to an embodiment of the present invention using a spring-based discharge assembly.

FIGS. 20A-20D show an eye drop propulsion device according to an embodiment of the present invention using a pin compressor assembly.

FIGS. 25A-25E show an eye drop propulsion device according to an embodiment of the present invention configured to automatically cover and uncovers an eye-port and fill or load and discharge the compression chamber in a single operation of the compressor assembly.

FIGS. 26A-26D show the operation of the eye drop propulsion device of FIGS. 25A-25E when force is applied to the compressor assembly.

FIGS. 35A-35C show an eye drop propulsion device according to an embodiment of the present invention illustrating a self-occluding option in a horizontal configuration, both with and without a retractable retractor assembly.

FIGS. 37A-37H show an embodiment of the present invention having a self-occluding option, along with its exemplary operation.

DETAILED DESCRIPTION OF THE PREFERRED EMBODIMENT

Figure 1:
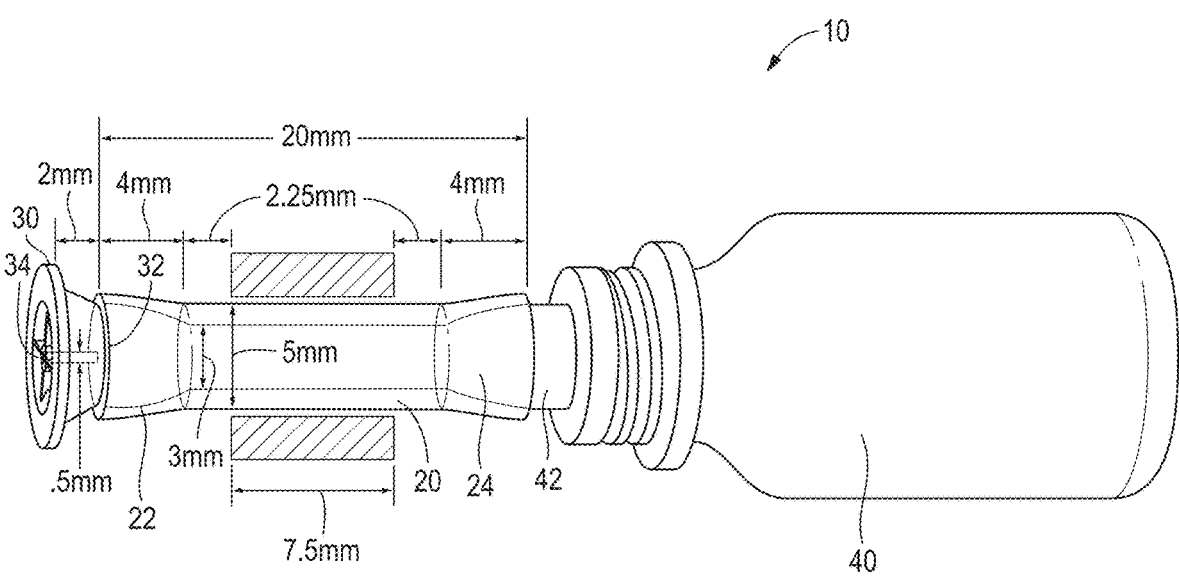
FIG. 1 shows an eye drop propulsion device according to an embodiment of the present invention, not including an eye-drop cover.

An eye drop propulsion device 10 to be used with an eye (not shown) is described with reference to FIGS. 1 and 2. The eye drop propulsion device 10 includes a compression chamber 20, a dispenser 30, and an eye drop bottle 40. The compression chamber 20, in this embodiment preferably made of flexible silicone or the like, includes an opening at a first end referred to herein as an eye-port 22 and an opening at a second end referred to herein as a bottle-port 24. The dispenser 30 includes a plug 32 at a first end, preferably made of plastic or the like and configured to communicate fluid or liquid (terms used interchangeably herein) from the compression chamber 20 into the dispenser 30, wherein the plug 32 is preferably configured to securely fit in watertight fashion into the eye-port 22 of the compression chamber 20. The plug 32 may be secured into the eye-port 22 in removable fashion, for example by friction fit, screwed into threads within the eye-port of the compression chamber 20, or otherwise, or in non-removable fashion, for example by glue, melting the plug 32 to the compression chamber 20, or the like. The dispenser 30 includes a dispenser aperture 34 at a second end opposite the first end configured to allow expulsion of liquid under pressure from the eye-port 22 of the compression chamber 20 via the plug, through the dispenser and out the dispenser aperture. While the diameter and length of the dispenser aperture 34 can vary depending on the desired amount of liquid to be allowed via the aperture and force and distance that a drop will be propelled, based on experimentation an aperture measuring about 0.5 mm and a length of about 2 mm has been found optimal for propelling typically a drop of liquid from the aperture. Both the diameter of the dispenser aperture 34 and the length primarily impact the speed at which a drop 98 is propelled. As used herein, in certain embodiments the dispenser 30 may not be present, and only a dispenser aperture 34 may be connected to or form part of the compression chamber 20 at or near the eye-port 22. The eye drop bottle 40 may be any type of container used to dispense a liquid eye drop solution that includes a nozzle 42 (*d*) having a nozzle aperture 44 from which liquid eye drops are dispensed. The bottle-port 24 is attached to the nozzle 42 of the eye drop bottle 40, preferably in a removable fashion, for example by friction fit, screwed into threads on the nozzle or bottle corresponding to threads in the bottle-port, or the like, but may also be secured in a non-removable fashion, for example by glue, manufacturing the tube to the nozzle, or the like. It should be noted that the eye drop bottle (or container), as described herein, need not be fully or even partially vertical in operation. Rather, it need only be oriented downward sufficient that at least a portion of the liquid retained therein accumulates in the nozzle for transmission to the compression chamber or dispenser, depending on the embodiment.

As used herein, a drop of liquid is not defined solely as a tear-shaped portion of liquid, but as a small volume (i.e., parcel, mass, collection, body, quantum or portion) of fluid of any shape that moves as a cohesive unit in a generally linear fashion towards the eye and that contacts the eye at a single directed location. There are typically approximately 20 drops per cubic centimeter (cc) (aka one milliliter (mL)), and a drop is typically approximately 0.05 ml. The precise size may vary, however, based on other characteristics of the liquid at issue, for example, viscosity or whether the liquid is a suspension. Examples of typical liquids used for eye drops include lubricating drops, medicated drops, and rewetting drops. The invention is readily adaptable to application of any type of eye drop without undue experimentation.

Preferred embodiments of the present invention provide for propelling a drop of fluid towards the eye, including by sizing the compression chamber volume, area compressed by the compressor(s), and length and diameter of the dispenser aperture. Despite being sized to propel a drop of fluid, more than a drop of fluid may be propelled due to variables including the type and viscosity of fluid, the degree of pressure applied by the compressor(s), and the like, without departing from the scope of the present invention.

As used herein, the terms propel or propelling eye drops describes the targeted movement of a liquid drop from the eye drop propulsion device towards the eye without the aid of gravity, which is distinct from applying a liquid drop through the aid of gravity and by tilting a user's head to position the eye drop bottle generally vertically (or at an angle) to the eye for application. Whereas typical eye drop application require holding the bottle, tilting the head, holding the eye open, and squeezing the bottle to release a drop that falls downwards due to gravity towards the eye, the present invention safely propels a drop towards the eye in a generally horizontal direction without the need to tilt the head or otherwise rely on gravity to move the liquid from the bottle to the eye. As used herein, propelling a drop is also different from spraying a mist, which involves dispersing numerous drops or droplets (very small drops) in a non-targeted, wide or cloud-like pattern (e.g., perfume sprayer, humidifier, or aerosol can), compared to propelling a drop, which involves a targeted, directed, and focused movement of the drop towards the eye.

Figure 3:
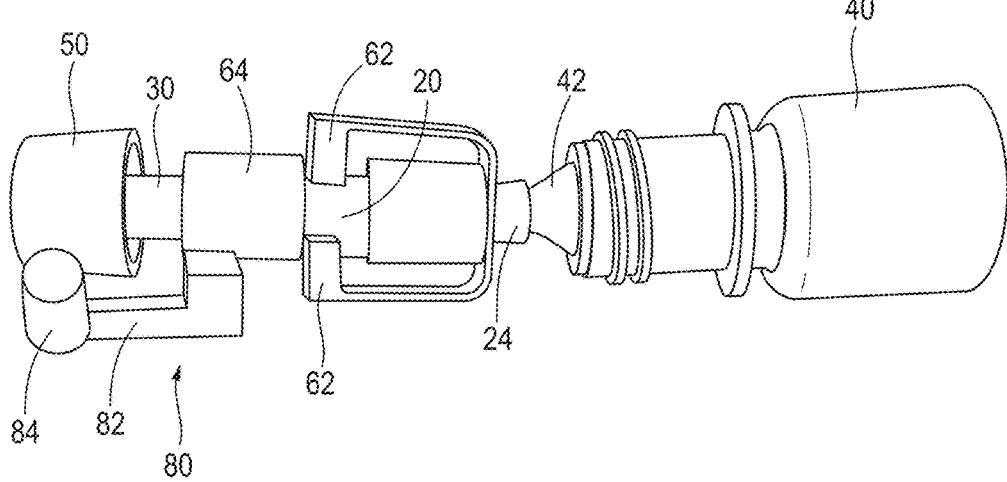
FIG. 3 shows an eye drop propulsion device including a compressor assembly and a retractor assembly according to an embodiment of the present invention.
Figure 4:
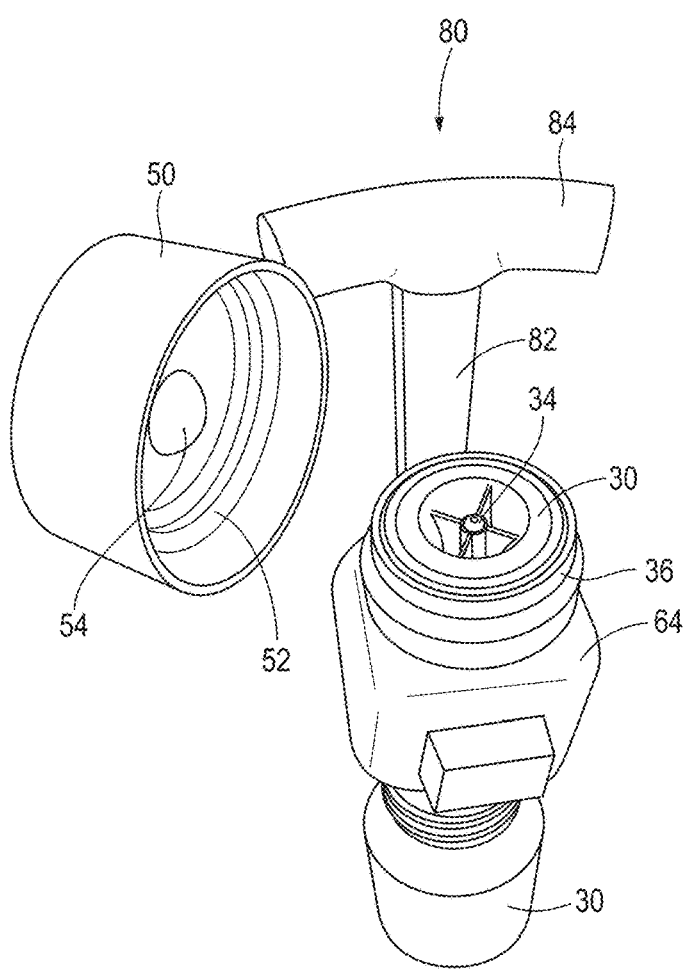
FIG. 4 shows an enlarged view of the dispenser and retractor assembly of the eye drop propulsion device of FIG. 3.

Variations of an alternative embodiment of the eye drop propulsion device 10 is shown with reference to FIGS. 3-5. These embodiments further includes additional structure including a retractor assembly as described below, but may otherwise include similarly referenced features. These embodiments further include an eye-port cover 50 configured to removably attach to and selectively occlude outflow of liquid from the eye-port 22 via the dispenser aperture 34 of the dispenser 30, a compressor assembly 60 configured to create positive pressure in the compression chamber 20 upon activation and a vacuum when deactivated, and a retractor assembly 80 configured to retract a lower eye lid. As described in greater detail below, inclusion of the retractor assembly 80 is only one variation of the present invention. It will be appreciated that any alternative embodiment may not include the retractor assembly, which is an optional feature.

In two similar embodiments shown with reference to FIGS. 3 and 4, the eye-port cover 50 includes threads 52 that correspond to threads 36 on the second end of the dispenser 30 allowing the eye-port cover to be removably attached to and removed from the dispenser via the mated threads. In alternative embodiments, the eye-port cover may be removably attached to the dispenser 30 via friction fit, a snap-lock configuration, a sliding cover, a spring-loaded cover, or the like. The eye-port cover 50 may include a specific occlusion cap or tip 54, preferably a silicone protrusion, aligned with the dispenser aperture 34 of the dispenser 30 when the eye-port cover is in place to occlude outflow of liquid from the eye-port 22 via the dispenser aperture 34 of the dispenser 30. In a preferred embodiment, the eye-port cover 50 and occlusion cap 54 are configured such that there is no significant change in pressure in the compression chamber 20 when the eye-port cover 50 is secured to the dispenser 30. The occlusion cap 54 may be a separate feature or an integrated part of the eye-port cover. In alternative embodiments described herein, modification may be made to the dispenser and dispenser aperture size to provide self-occlusion of the dispenser aperture without the need for an eye-port cover 50 and/or occlusion cap.

In embodiments shown with reference to FIGS. 3-5, the compressor assembly 60 is activated via one or more compressor(s) 62 configured to squeeze or pinch the compression chamber 20 upon exertion of force, for example, by a user pressing the compressor(s) together, or a button or other activation device (not shown) that activated the compression. While the embodiment shown in FIG. 3 does not include a separate housing, in the embodiment shown with in FIG. 4, the compressor assembly 60 includes a housing 64 configured to support the compressor(s) 62 proximate to the compression chamber 20. In yet an alternative embodiment, the eye-port cover 50 may be configured to removably connect to the housing 64 when occluding outflow of liquid, rather than directly to the dispenser 30. As used throughout, a housing separate from the dispenser 30 is optional, as the dispenser may provide sufficient support for other components that a separate housing structure is not needed, or that the dispenser is considered a housing, for example, to support the compression chamber 20, the compressor(s) 62, the eye-port cover 50, the retractor assembly 80, and the like.

The operation of the compression assembly 60 is further described with reference to FIG. 5, which shown an embodiment with a housing similar to that shown in FIG. 4. As shown further with reference to FIG. 5A, with the eye drop bottle 40 in an inverted position with the nozzle 42 pointed generally downwards (sufficiently aligned with gravity that liquid within the eye drop bottle is concentrated at the nozzle), and with the eye-port cover 50 that includes an occlusion cap 54 in place to occlude outflow of liquid from the eye-port 22, the compressor(s) 62 is activated (i.e., pressed), for example in the direction shown by arrows 66, 66', the compression chamber 20 is squeezed, pinched or otherwise compressed, forcing air to flow from the compression chamber 20 into the eye drop bottle 40 generally in the direction shown by arrow 68. As shown with reference to FIG. 5B, as the compressor(s) 62 is deactivated (i.e., released), for example in the direction shown by arrows 70, 70', a vacuum is created in the compression chamber 20, which causes a portion of liquid in the inverted eye drop bottle 40 to flow into the compression chamber 20 generally in the direction shown by arrow 72. As shown with reference to FIG. 5C, the eye-port cover 50 is then removed, which opens the dispenser aperture 34 of the dispenser 30. The compressor(s) 62 is again activated (i.e., pressed), for example in the direction shown by arrows 66, 66', which again compresses the compression chamber 20, thereby propelling at least a portion of the liquid in the compression chamber 20 from the eye-port 22 via the aperture 34 of the dispenser 30 in the direction shown by arrow 74, in operation towards an eye. The anticipated application of the present invention is with a human eye, but it will be appreciated that it has application to any eye (e.g., animal) benefitting from eye-drop solution. It should be noted that even though some fluid may also be propelled from the compression chamber 20 through the bottle-port 24 into the eye drop bottle 40 in the direction shown by arrow 76, there is enough resistance from the nozzle aperture 44 of the eye drop bottle 40, as well as from the fact that the bottle is a closed chamber except for the nozzle aperture, that a sufficient volume of liquid is still propelled through the eye-port without having the need to occlude the bottle-port 24.

As shown with reference to FIGS. 3-5, embodiments of the present invention include a retractor assembly that preferably includes a retractor 82 and a retractor pad 84, which may be configured either to permanently extend from the compression chamber 20 (e.g., via the housing 64) or be dynamically retracted or extended, as desired, into position during operation, for example via a hinge (not shown). Under either configuration, in operation, the retractor 82 and retractor pad 84 are positioned and then retract the lower lid as shown in FIG. 5C when at least a portion of the liquid in the compression chamber 20 is propelled from the eye-port 22 via the dispenser aperture 34 of the dispenser 30 in the direction generally shown by arrow 74, for example towards a typical human eye 86 (see FIG. 6).

As used herein, the eye 86 refers to all parts around the eyeball and including surrounding structures such as the conjunctiva and fornix. The eye includes characteristics such as a lower lid 88 having lower lid margin 90 and a lower conjunctiva and lower fornix 94 (i.e., the pocket between the mucous membrane covering the inside of the lower lid (88) and the mucous membrane covering the lower part of the eye), and an upper lid 96.

As used herein, the compression chamber 20 and compressor(s) 62 may come in a wide variety of shapes, sizes and configurations. Compression chambers may, for example, be tubes, bladders, syringes, or any container having sufficient volume to provide for modification of pressure therein upon application of one or more compressors and sufficient structure to support at least an eye-port and a bottle-port. In certain embodiments, the compression chamber may be configured to a combination of air and liquid. In other embodiments, the compression chamber may be configured to hold only air, but include integrated or otherwise connected a separate reservoir (not shown) to hold liquid for use in the present invention. The compression chamber may be oriented in a variety of ways, for example including horizontal, vertical or at an angle with respect to the dispenser aperture and eye drop bottle. As described herein, the compressor(s) include anything from a user's fingers applying pressure (e.g., pinching) the compression chamber to buttons, blocks, rollers, plungers, or any structure configured to apply pressure to at least a part of the compression chamber to modify the volume therein.

Figure 6A:
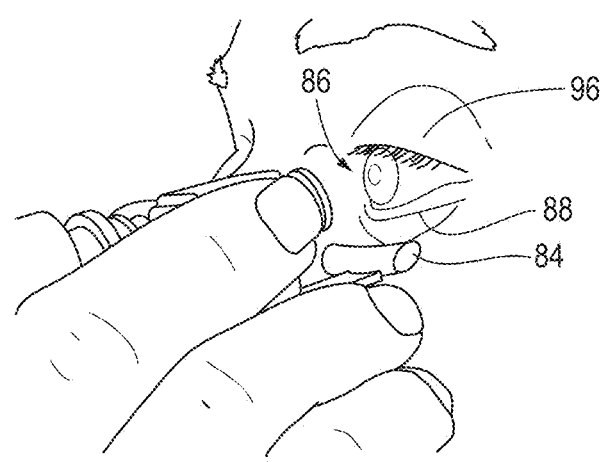
FIGS. 6A-6C show the operation of the eye drop propulsion device with a retractor assembly in relationship to an eye.
Figure 6B:
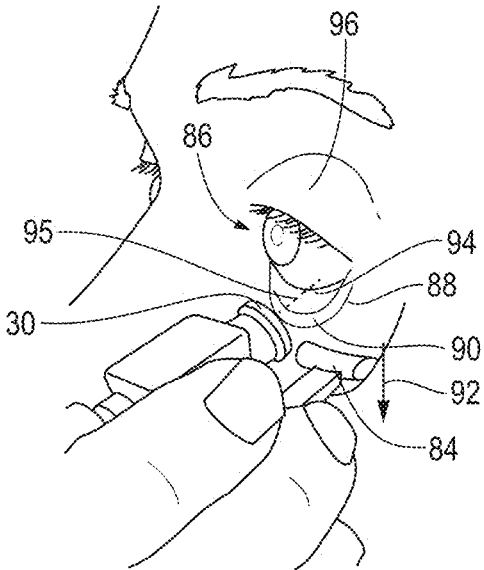
Figure 6C:
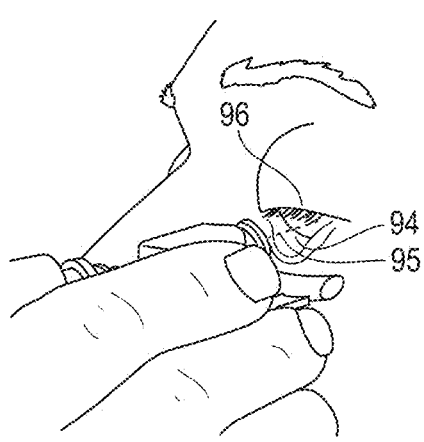

A preferred method of the present invention is described further with reference to FIG. 6. In FIG. 6A, the retractor pad 84 of the retractor 82 is positioned just under the lower lid margin 90. In FIG. 6B, the lower lid 88 is retracted downward generally in the direction shown by arrow 92 by the retractor pad 84, thereby positioning the lower lid margin 90 of the lower lid 88 beneath the "line of fire" shown generally along the dotted lines 94 between the dispenser aperture 34 and the open eye 86, specifically targeting the lower conjunctiva and fornix 94. As shown with reference to FIG. 6C, the lower conjunctiva and fornix 94 can still be targeted even with the upper lid 96 closed.

Regardless of the type of compression chamber, compressor(s), housing, or use of a retractor assembly, the operation of various embodiments of the present invention may be further explained as either a single path configuration having 2-poles (see FIGS. 7 and 8) or a dual path configuration having 3-poles (see FIG. 9). The fundamentals of these two configurations further explain the operation of the various embodiments described herein.

Figure 7A:
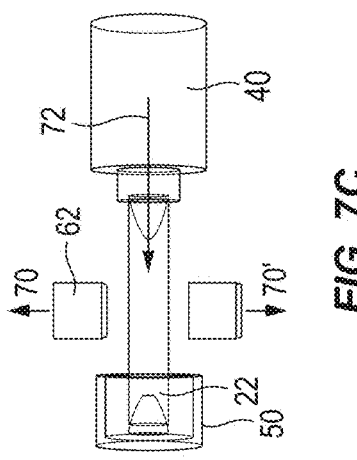
FIGS. 7A-7F show an eye drop propulsion device according to an embodiment of the present invention including an eye-drop cover.
Figure 7B:
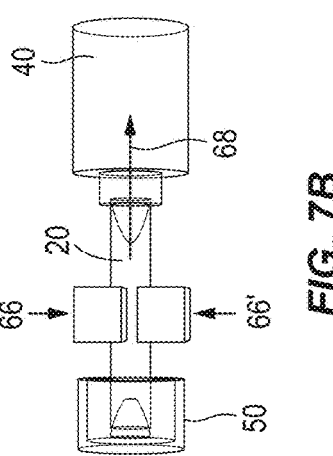
Figure 7C:
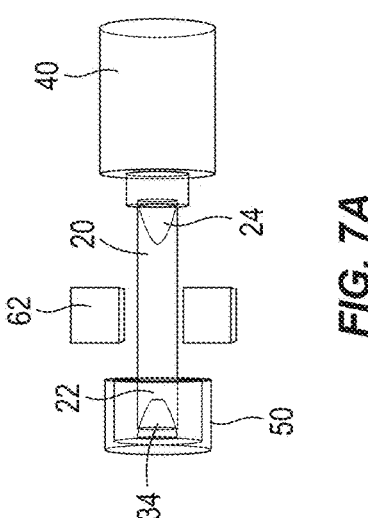
Figure 7D:
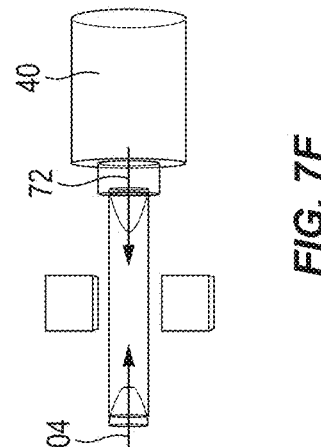
Figure 7E:
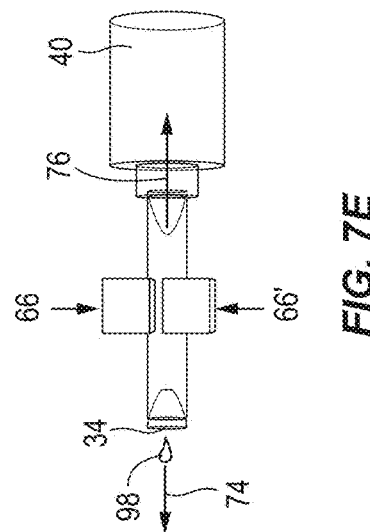
Figure 7F:
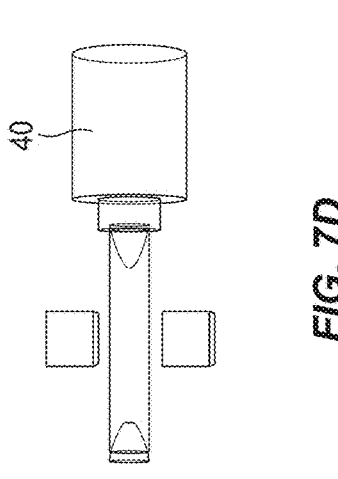

FIGS. 7A-7F illustrate a single path configuration. FIG. 7A shows an embodiment of the eye drop propulsion device 10 including the compression chamber 20 having the eye-port 22 and the bottle-port 24 connected to the eye drop bottle 40, along with the dispenser 30 connected to the compression chamber 20 and having a dispenser aperture 34 and eye-port cover 50 to occlude the dispenser aperture 34, together with a compressor assembly 60 having compressor(s) 62. The single path in this embodiment is between the eye drop bottle 40 to the dispenser aperture 34 via the compression chamber 20, with the 2-poles referred to as the eye drop bottle 40 and the dispenser aperture 34. As shown in FIG. 7B, the compression chamber 20 is compressed using compressor(s) 62 generally in the direction shown by arrows 66, 66', which forces air (and perhaps a portion of any fluid remaining in the compression chamber if the device was previously used) into the eye drop bottle 40 generally in the direction shown by arrow 68. This operation creates a positive pressure in the bottle relative to the atmosphere (i.e., the total amount of liquid and air in the system is now occupying a smaller space). As shown in FIG. 7C, as the compressor(s) 62 are released generally in the direction shown by arrows 70,70', the elasticity of the compression chamber (in one example, a silicone tube) forces the compression chamber to reopen, creating a vacuum in the compression chamber 20 causing fluid to flow from the eye drop bottle 40 generally in the direction shown by arrow 72 into the compression chamber 20, equalizing pressure between the bottle and chamber. Because this is a closed system with the occluding eye-port cover 50 in place, the pressures within the bottle and chamber are at atmospheric pressure. FIG. 7D shows the device with the occluding eye-port cover 50 removed. As shown in FIG. 7E, when the compression chamber 20 is again activated using compressor(s) 62, typically a drop 98 of fluid from the eye drop bottle 40 is propelled from the dispenser aperture 34 towards the eye 86 generally in the direction shown by arrow 74 at the same time that a small amount of fluid is forced from the compression chamber 20 back into the eye drop bottle 40 generally in the direction shown by arrow 76. As shown in FIG. 7F, once the compressor(s) are released, the pressure within the compression chamber 20 and eye drop bottle returns to equilibrium since the dispenser aperture 34 is open, preparing the device to repeat the process to expel another drop as may be desired.

Experimentation has confirmed what occurs if a single cycle is used with the single path configuration described above with reference to FIG. 7 without first pressurizing the eye drop bottle 40, as shown with reference to FIGS. 8A-10E. This applies in embodiments where the eye drop propulsion device 10 is not configured to be self-occluding, for example as described with reference to FIG. 37, where the compression chamber has a self-occluding aperture that prevents air from flowing in through the aperture both during and after the release of the compressor, thereby preventing the fluid in the compression chamber from being drawn back into the container, making the need for a separate "reloading" cycle unnecessary In FIG. 8A, the cycle starts with the cover off and the compression chamber 20 having been loaded with fluid. In FIG. 8B, the compressor(s) 62 are activated generally in the direction shown by arrows 66,66', propelling a drop 98 generally in the direction shown by arrow 74. As explained above, some part of the liquid in the compression chamber 20 is forced back into the eye drop bottle 40 generally in the direction shown by arrow 76. In FIG. 8C, the occluding eye-port cover 50 (which may further include the separate occlusion cap 54) is replaced while the compression chamber 20 is still compressed by compressor(s) 62. In FIG. 8D, the compressor(s) 62 are released (with the eye-port cover 50 still occluding the dispenser aperture 34), creating a vacuum in the compression chamber 20 relative to the pressure in the eye drop bottle 40, forcing fluid to flow from the bottle into the compression chamber generally in the direction shown by arrow 72. Because approximately the total amount of fluid and air are now occupying a larger space in a closed system, the pressure in both the bottle and compression chamber is less than atmospheric pressure. In FIG. 8E, the occluding eye-port cover 50 is removed, and the higher atmospheric pressure forces air into the compression chamber 20 generally in the direction shown by arrow 104 and thus most of the fluid in the compression chamber 20 to flow back towards the eye drop bottle 40 generally in the direction shown by arrow 76. There is nothing left in the compression chamber to expel through the eye-port when the compressors are compressed again. In this case, two cycles are needed to avoid creating a significant vacuum behind the liquid being held in the compression chamber 20 to prepare the device or "reload" for further use.

Figures 9A, 9B, 9C, 9D:
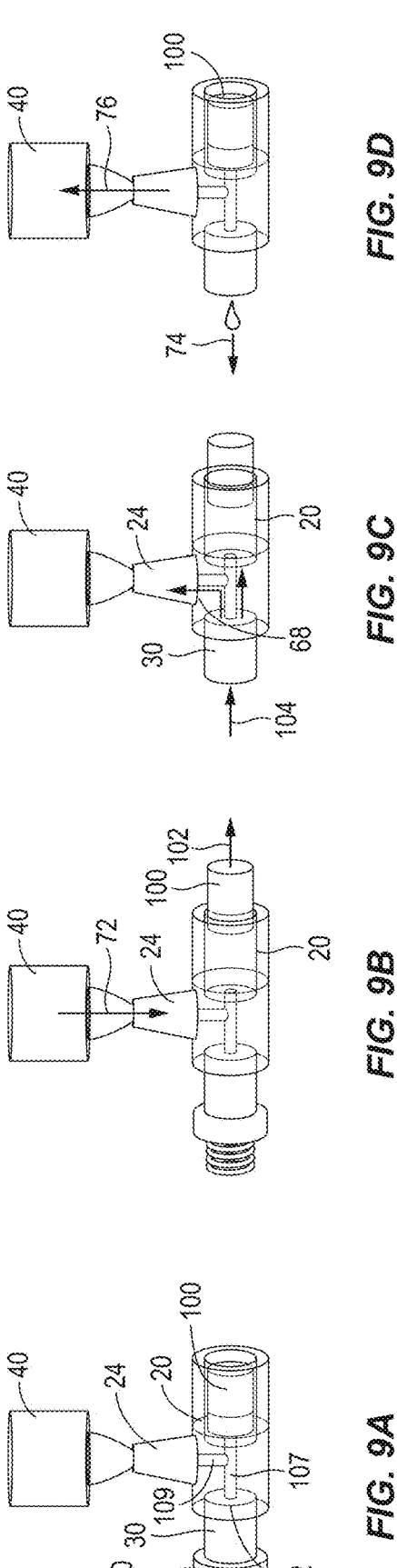
FIGS. 9A-9D show an eye drop propulsion device according to an embodiment of the present invention using a plunger compressor assembly.

As shown with reference to FIGS. 9A-9D, a dual path configuration is described. FIG. 9A shows an embodiment of the eye drop propulsion device 10 wherein the compression chamber 20 extends along a separate eye-port path extension 107 to the eye-port 22 connected to the dispenser 30 and a separate bottle-port path extension 109 to the bottle-port 24 connected to the eye drop bottle 40. Both the eye-port path extension 107 and the bottle-port path extension 109 are herein considered part of the compression chamber 20. In the embodiment shown, the separate paths from the eye-port 22 and bottle-port 24 join before entering a main chamber of the compression port. The eye-port cover 50 and/or occlusion cap 54 occlude the dispenser aperture 34 (not shown). In this embodiment, the compressor assembly 60 includes a plunger 100 as the compressor 62, wherein the plunger is connected and occupying space within the compression chamber and configured to selectively reduce or expand the capacity of the compression chamber as it is operated, thereby altering the pressure therein. The dual path in this embodiment refers to single path between the compression chamber 20 and eye drop bottle 40 and another path between the compression chamber 20 and the dispenser 30. The 3-poles refers to the compression chamber 20, the eye drop bottle 40, and the dispenser 30.

In FIG. 9B, the plunger 100 is withdrawn from compression chamber 20 generally in the direction shown by arrow 102, creating a vacuum in the compression chamber 20 relative to the eye drop bottle 40, causing fluid to flow from the eye drop bottle 40 into the compression chamber 20 generally in the direction shown by arrow 72. In an alternative embodiment, the fluid may flow into a separate chamber or reservoir (now shown), preferably within the compression chamber, but in fluidic communication with the dispenser 30. Once the plunger 100 stops moving and the compression chamber 20 is filled with fluid, the chamber and bottle reach equilibrium, both having an equal pressure lower than atmospheric pressure. In FIG. 9C, the occluding eye-port cover 50 has been removed. Because both the compression chamber 20 and the eye drop bottle 40 have a lower atmospheric pressure, air will flow via the dispenser aperture 34 along both the eye-port path extension 107 generally in the direction shown by arrow 104 and the bottle-port path extension 109 generally in the direction shown by arrow 68. Based on experimentation, most of the air flows into the eye-drop bottle 40 as the compression chamber 20 is a relatively small, rigid space already filled with fluid. As shown in FIG. 9D, when the plunger 100 is depressed, a drop 98 is expelled from the dispenser aperture 34 generally in the direction shown by arrow 74, and a small amount of fluid flows into the eye drop bottle 40 generally in the direction shown by arrow 76, and the device returns to its initial state.

As used herein, the volume of the compression chamber 20 and size or area of compression of the compressor(s) 62 are configured based on the desire for a drop 98 versus multiple drops to be dispensed for each action or cycle of the invention. For both the single and dual path configurations, in a preferred embodiment, the compression chamber 20 volume is preferably slightly larger than the size of a drop (e.g., 0.05 ml), to provide sufficient volume for the drop while allowing necessary space for connection to the eye-port 22 and bottle-port 24 such that when the compressor(s) is operated the compression chamber maintains it structural integrity. The existence of volume in the compression chamber beyond that sufficient to propel a drop (0.05 ml) also results in a small portion of the fluid to be pushed back into the eye drop bottle 40 during operation.

Figure 2:
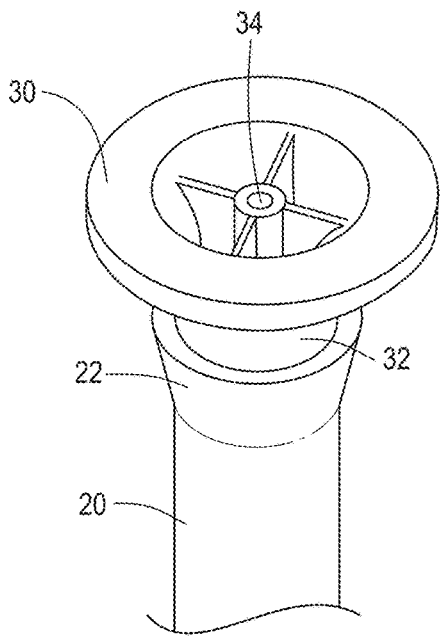
FIG. 2 shows an enlarged view of a dispenser of the eye drop propulsion device of FIG. 1.

To illustrate this aspect of the present invention, reference is made back to FIGS. 1 and 2, now specifically to the exemplary dimensions to explain the fundamental operation of the various embodiments of the present invention. This embodiment shows use of a silicone tube as the compression chamber 20, where the tube length is 20 mm with an outer diameter of 5 mm, an inner diameter of 3 mm, and a tube wall thickness of 1 mm. The eye-port 22 and bottle-port 24 are both approximately 4 mm in length. The compression chamber length subject to compression by the compressor(s) 62 is approximately 7.5 mm. That leaves approximately 4-5 mm total on either side of the compressed area combined, which constitutes the non-compressed portions of the compression chamber and, along with the eye-port and bottle-port, are necessary to connection to maintain structural integrity. Experimentation has confirmed that in this exemplary embodiment, preferably a minimum of approximately 2 mm between the compressor(s) the eye-port and bottle-port, respective, is appropriate to allow adequate room for compression of the compression chamber. Accordingly, the volume of the compression chamber 20 (here a silicone tube) subject to compression during operation is calculated using the equation $pi \times R \times R \times L = 3.14 \times 1.5 \times 1.5 \times 7.5 = 52.98 = 0.053$ ml, which is slightly larger than a typical eye drop as used herein of 0.5 ml. Thus, the volume of the compression chamber compressed approximates the volume of the desired drop. The size and length of the dispenser aperture, in this example the dispenser aperture being 0.5 mm in diameter and having a length of approximately 2 mm, impacts the speed of compression and is a factor in determining the resulting force and distance that the drop 98 will be propelled towards the eye. While not precise and subject to variation depending on the viscosity of the fluid and operation of the compressor assembly 60 as part of the compression chamber 20, increasing the volume of the compression chamber 20 in relation to the size and therefore area compressed by the compressor(s) 62 allows for multiple drops to be chambered and propelled without the need to reset or "reload" the eye drop propulsion device 10.

A preferred method of the present invention is described further with reference FIG. 10 (single path, 2-pole configuration) and FIG. 11 (dual path, 3-pole configuration).

Figure 10A:
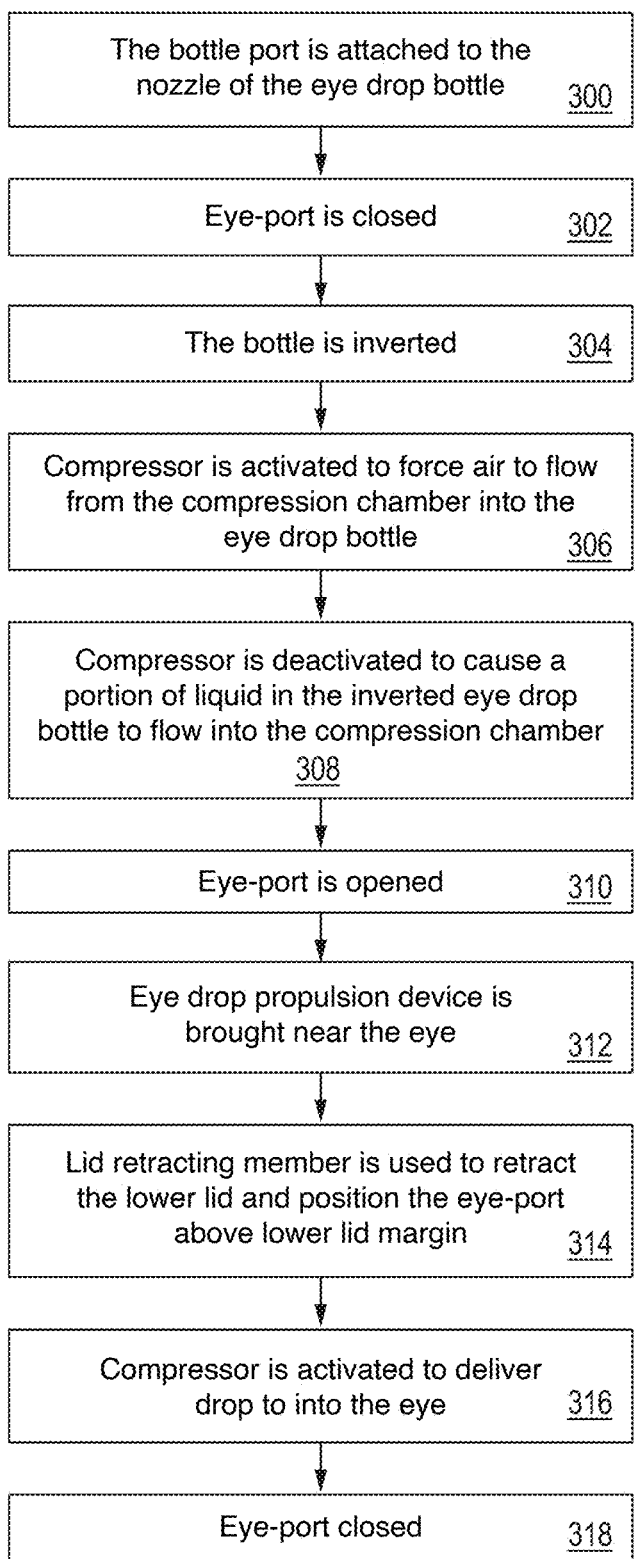
FIG. 10A shows a flowchart detailing one method of using the present invention including a retractor assembly.

Referring to FIG. 10A, the methodology of a single path, 2-pole configuration is described, for example with further reference to FIGS. 7-8 with use of the retractor assembly 80. At block 300, the nozzle 42 of the eye drop bottle 40 is inserted into the bottle-port 24 of the compression chamber 20. At block 302, the eye-port is closed, for example the cover 50 and occlusion cap 54 are used to fully occlude the eye-port 22. In one embodiment, the eye-port cover 50 is attached to the dispenser 30 or housing 64 such that the occlusion cap 54 aligns with and fully occludes the dispenser aperture 34. At block 304, the eye drop bottle 40 is inverted or tilted with the nozzle 42 pointed generally downwards (sufficiently aligned with gravity that liquid within the eye drop bottle is concentrated at the nozzle). At block 306, the compressor(s) 62 is activated (i.e., pressed), for example in the direction shown by arrows 66, 66', forcing air to flow from the compression chamber 20 into the eye drop bottle 40 generally in the direction shown by arrow 68. At block 308, as the compressor(s) 62 is deactivated (i.e., released), for example in the direction shown by arrows 70, 70', creating a vacuum in the compression chamber 20, which causes a portion of liquid in the inverted eye drop bottle 40 to flow into the compression chamber 20 generally in the direction shown by arrow 72. At block 310, the eye-port is opened, for example the cover 50 and cap 54 are used to at least partially open the eye-port 22. In one embodiment, the eye-port cover 50 is removed from the dispenser 30 or housing 64 such that the cap 54 clears occlusion of the dispenser aperture 34. At block 312, the eye drop propulsion device 10 is brought near the eye, and preferably positioned on or near the skin below the lower lid margin 90. At block 314, the retractor assembly 80 is used to retract the lower lid 88 downward so that the dispenser aperture 34 is aimed above the lower lid margin 90 and towards the lower conjunctiva and fornix 94 and/or support the eye drop propulsion device 10. While in this position, at block 316, the compressor 62 is activated (i.e., pressed), thereby propelling a drop towards the lower conjunctiva and fornix 94. Testing has confirmed that a drop is propelled into the eye with remarkable consistency. At block 318, the eye-port is closed, for example the cover 50 and/or occlusion cap 54 are used to fully occlude the dispenser aperture 34 of the eye-port 22, to await another eye drop instillation.

It will be appreciated that certain of these steps could be removed, modified or otherwise altered without diminishing the unique methodology. For example, the bottle-port may have already been attached to the nozzle of the eye drop bottle, such as in an embodiment where the compression chamber 20 and/or compressor assembly 60 is already affixed to, manufactured with, or otherwise part of the eye drop propulsion device 10 with dispenser 30. In such embodiment, step 300 would be obviated. In another example, if a first usage through block 318 occurs, the method may begin at block 304. Alternatively, if after a first usage blocks 318 occurs, and further blocks 304-308 occurs, the device may be ready for immediate use starting at block 310. In other words, a portion of liquid may already be "loaded" into the compression chamber and be ready for expulsion, for example to apply a drop to a second eye. In another example, blocks 306-308 can readily and efficiently be accomplished in a single continuous step. Likewise, blocks 312 through 316 can readily and efficiently accomplished in a single continuous step. In a different embodiment, the methodology of the steps of retracting the lower lid of the eye and aligning the dispenser aperture above the lower lid of the eye are not required as optional, given that the invention may propel the drop generally towards the eye sufficient to effectuate the purpose. Other examples of methodology modification consistent with the present invention and dependent on the specific features of the particular embodiment may be apparent without undue experimentation.

It will be appreciated that while several of the embodiments or methods describe inverting the eye drop bottle 40 generally downwards (sufficiently aligned with gravity that liquid within the eye drop bottle is concentrated at the nozzle), this is only required in embodiments where the eye drop bottle is oriented such that due to gravity the fluid contained therein is not concentrated at the nozzle. The embodiments and methods described herein may readily be modified such that the orientation of the eye drop bottle is generally downwards (sufficiently aligned with gravity that liquid within the eye drop bottle is concentrated at the nozzle) throughout operation of the device such that inversion of the eye drop bottle is not required and need not be included as a separate method step.

Referring to FIG. 10B, the methodology of a single path, 2-pole configuration is described, for example with further reference to FIGS. 7-8 but without use of the retractor assembly 80. In this methodology, a user's fingers alone can be used to support and position the eye drop propulsion device 10. At block 350, the nozzle 42 of the eye drop bottle 40 is inserted into the bottle-port 24 of the compression chamber 20. At block 352, the eye-port is closed, for example the cover 50 and occlusion cap 54 are used to fully occlude the eye-port 22. In one embodiment, the eye-port cover 50 is attached to the dispenser 30 or housing 64 such that the occlusion cap 54 aligns with and fully occludes the dispenser aperture 34. At block 354, the eye drop bottle 40 is inverted with the nozzle 42 pointed generally downwards (sufficiently aligned with gravity that liquid within the eye drop bottle is concentrated at the nozzle). At block 356, the compressor(s) 62 is activated (i.e., pressed), for example in the direction shown by arrows 66, 66', forcing air to flow from the compression chamber 20 into the eye drop bottle 40 generally in the direction shown by arrow 68. At block 358, as the compressor(s) 62 is deactivated (i.e., released), for example in the direction shown by arrows 70, 70', creating a vacuum in the compression chamber 20, which causes a portion of liquid in the inverted eye drop bottle 40 to flow into the compression chamber 20 generally in the direction shown by arrow 72. At block 360, the eye-port is opened, for example the cover 50 and occlusion cap 54 are used to at least partially open the eye-port 22. In one embodiment, the eye-port cover 50 is removed from the dispenser 30 or housing 64 such that the occlusion cap 54 clears occlusion of the dispenser aperture 34. At block 362, the eye drop propulsion device 10 is brought near the eye, and preferably positioned on or near the skin below the lower lid margin 90. At block 364, a user's fingers alone can be used to support and position the eye drop propulsion device 10 and retract the lower and/or upper lids 88, 96. A user could also be asked to simply look up before the drop is dispensed to assist in targeting the drop to hit the lower conjuctiva. In this embodiment, a user's finger or fingers may be used to retract the lower lid 88 downward so that the dispenser aperture 34 is aimed above the lower lid margin 90 and towards the lower conjunctiva and fornix 94. While in this position, at block 366 the compressor 62 is activated (i.e., pressed), thereby propelling a drop towards the lower conjunctiva and fornix 94. At block 368, the eye-port is closed, for example the cover 50 and occlusion cap 54 are used to fully occlude the eye-port 22, to await another eye drop instillation.

As outlined above with respect to FIG. 10A methodology, it will be appreciated that certain of the steps illustrated in FIG. 10B could be removed, modified or otherwise altered without diminishing the unique methodology. For example, the bottle-port may have already been attached to the nozzle of the eye drop bottle, such as in an embodiment where the compression chamber 20 and/or compressor assembly 60 is already affixed to, manufactured with, or otherwise part of the eye drop propulsion device 10 with dispenser 30. In such embodiment, step 350 would be obviated. In another example, if a first usage through block 368 occurs, the method may begin at block 354. Alternatively, if after a first usage blocks 368 occurs, and further blocks 354-358 occurs, the device may be ready for immediate use starting at block 360. In other words, a portion of liquid may already be "loaded" into the compression chamber and be ready for expulsion, for example to apply a drop to a second eye. In another example, blocks 356-358 can readily and efficiently be accomplished in a single continuous step. Likewise, blocks 362 through 366 can readily and efficiently accomplished in a single continuous step. Other examples of methodology modification consistent with the present invention and dependent on the specific features of the particular embodiment may be apparent without undue experimentation.

Another embodiment of a single path, 2-pole system would not require first injecting air into the eye drop bottle during the initial loading cycle, but may work as follows: the eye-port cover first occludes the eye-port while the compression chamber is compressed. The compression chamber would then be released, drawing fluid into the compression chamber. The bottle-port would then be occluded. The eye-port would then be opened, and the compression chamber compressed to propel the drop. The bottle-port would then be opened, to bring the entire system back to atmospheric pressure. To begin the cycle again, the compression chamber would be compressed, and the eye-port then closed. This embodiment requires obviates the need to have a loading cycle to pressurize the bottle and fill the chamber.

Referring to FIG. 11A, the methodology of a dual path, 3-pole configuration is described, for example with further reference to FIG. 9, but with use of the retractor assembly 80. At block 400, the nozzle 42 of the eye drop bottle 40 is inserted into the bottle-port 24 of the dispenser 30 or compression chamber 20. At block 402, the eye-port is closed, for example the cover 50 and occlusion cap 54 are used to fully occlude the eye-port 22. In one embodiment, the eye-port cover 50 is attached to the dispenser 30 or housing 64 such that the occlusion cap 54 aligns with and fully occludes the dispenser aperture 34. At block 404, the eye drop bottle 40 is inverted with the nozzle 42 pointed generally downwards (sufficiently aligned with gravity that liquid within the eye drop bottle is concentrated at the nozzle). At block 406, the plunger 100 is activated (i.e., withdrawn), for example in the direction shown by arrow 102, causing a portion of fluid in the container to flow into the dispenser generally in the direction shown by arrow 72. At block 408, the eye-port is opened, for example the cover 50 and cap 52 are used to at least partially open the eye-port 22. In one embodiment, the eye-port cover 50 is removed from the dispenser 30 or housing 64 such that the cap 52 clears occlusion of the dispenser aperture 34. At block 410, the eye drop propulsion device 10 is brought near the eye, and preferably positioned on or near the skin below the lower lid margin 90. At block 412, the retractor assembly 80 is used to retract the lower lid 88 downward so that the dispenser aperture 34 is aimed above the lower lid margin 90 and towards the lower conjunctiva and fornix 94 and/or support the eye drop propulsion device 10. While in this position, at block 414, the plunger 100 is activated (i.e., depressed), thereby propelling a drop towards the lower conjunctiva and fornix 94. Testing has confirmed that a drop is propelled into the eye with remarkable consistency. At block 416, the eye-port is closed, for example the cover 50 and occlusion cap 54 are used to fully occlude the eye-port 22, to await another eye drop instillation.

It will be appreciated that certain of these steps could be removed, modified or otherwise altered without diminishing the unique methodology. For example, the bottle-port may have already been attached to the nozzle of the eye drop bottle, such as in an embodiment where the compression chamber 20 and/or compressor assembly 60 is already affixed to, manufactured with, or otherwise part of the eye drop propulsion device 10 with dispenser 30. In such embodiment, step 400 would be obviated. In another example, if a first usage through block 416 occurs, the method may begin at block 404. Alternatively, if after a first usage block 416 occurs, and further blocks 400 and 404-406 occurs, the device may be ready for immediate use starting at block 408. In other words, a portion of liquid may already be "loaded" into the dispenser or compression chamber and be ready for expulsion, for example to apply a drop to a second eye. In another example, blocks 410 through 414 can readily and efficiently accomplished in a single continuous step. Other examples of methodology modification consistent with the present invention and dependent on the specific features of the particular embodiment may be apparent without undue experimentation.

Referring to FIG. 11B, the methodology of a dual path, 3-pole configuration is described, for example with further reference to FIG. 9 without use of the retractor assembly 80. In this methodology, a user's fingers alone can be used to support and position the eye drop propulsion device 10. At block 450, the nozzle 42 of the eye drop bottle 40 is inserted into the bottle-port 24 of the dispenser 30 or compression chamber 20. At block 452, the eye-port is closed, for example the cover 50 and occlusion cap 54 are used to fully occlude the eye-port 22. In one embodiment, the eye-port cover 50 is attached to the dispenser 30 or housing 64 such that the occlusion cap 54 aligns with and fully occludes the dispenser aperture 34. At block 454, the eye drop bottle 40 is inverted with the nozzle 42 pointed generally downwards (sufficiently aligned with gravity that liquid within the eye drop bottle is concentrated at the nozzle). At block 456, the plunger 100 is activated (i.e., withdrawn), for example in the direction shown by arrow 102, causing a portion of fluid in the container to flow into the dispenser generally in the direction shown by arrow 72. At block 458, the eye-port is opened, for example the cover 50 and occlusion cap 54 are used to at least partially open the eye-port 22. In one embodiment, the eye-port cover 50 is removed from the dispenser 30 or housing 64 such that the occlusion cap 54 clears occlusion of the dispenser aperture 34. At block 460, the eye drop propulsion device 10 is brought near the eye, and preferably positioned on or near the skin below the lower lid margin 90. At block 462, the retractor assembly 80 is used to retract the lower lid 88 downward so that the dispenser aperture 34 is aimed above the lower lid margin 90 and towards the lower conjunctiva and fornix 94. While in this position, at block 464, the plunger 100 is activated (i.e., depressed), thereby propelling a drop towards the lower conjunctiva and fornix 94. Testing has confirmed that a drop is propelled into the eye with remarkable consistency. At block 466, the eye-port is closed, for example the cover 50 and occlusion cap 54 are used to fully occlude the eye-port 22, to await another eye drop instillation.

It will be appreciated that certain of these steps could be removed, modified or otherwise altered without diminishing the unique methodology. For example, the bottle-port may have already been attached to the nozzle of the eye drop bottle, such as in an embodiment where the compression chamber 20 and/or compressor assembly 60 is already affixed to, manufactured with, or otherwise part of the eye drop propulsion device 10 with dispenser 30. In such embodiment, step 450 would be obviated. In another example, if a first usage through block 466 occurs, the method may begin at block 454. Alternatively, if after a first usage block 466 occurs, and further blocks 450 and 454-456 occurs, the device may be ready for immediate use starting at block 458. In other words, a portion of liquid may already be "loaded" into the dispenser or compression chamber and be ready for expulsion, for example to apply a drop to a second eye. In another example, blocks 460 through 464 can readily and efficiently accomplished in a single continuous step. Other examples of methodology modification consistent with the present invention and dependent on the specific features of the particular embodiment may be apparent without undue experimentation.

Figure 12A:
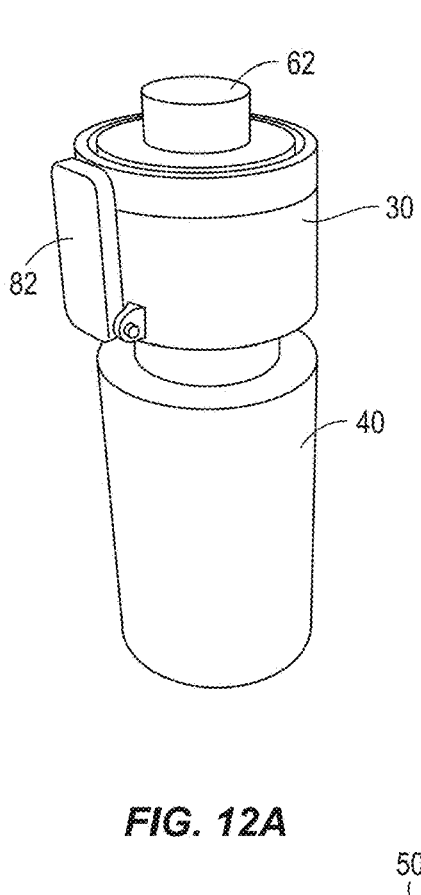
FIGS. 12A-12C show an eye drop propulsion device according to an embodiment of the present invention using a disc-shaped compressor assembly.
Figure 12B:
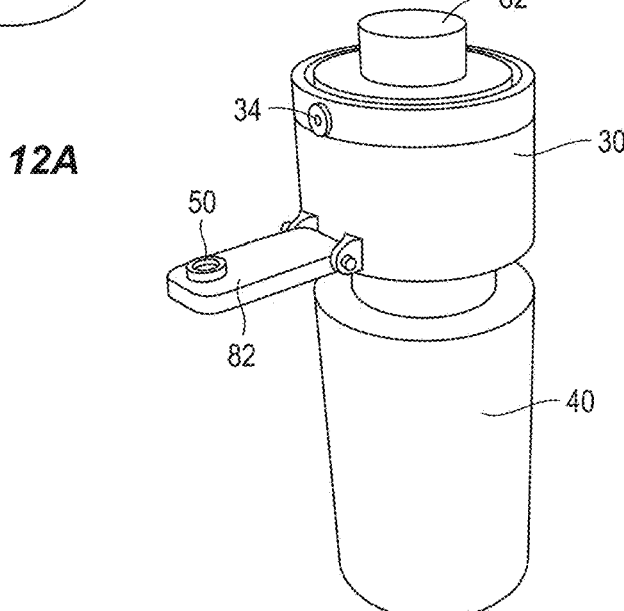
Figure 12C:
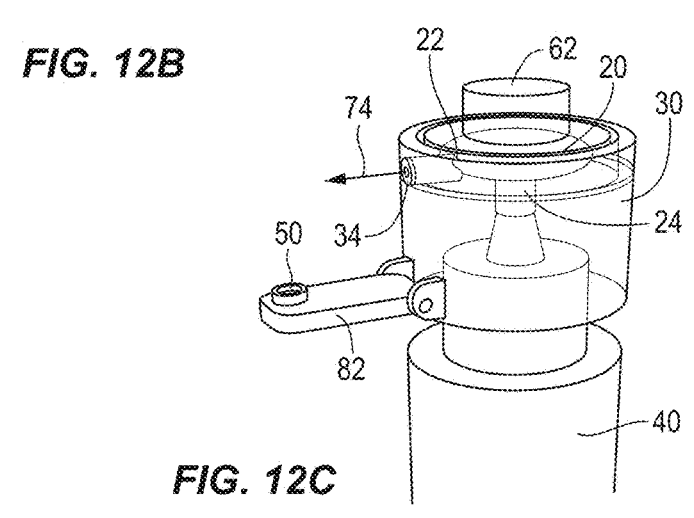

An alternative embodiment is shown with reference to FIGS. 12A-12C. In this embodiment, the dispenser 30 may be configured to be removably attached to the eye drop bottle 40, for example via dispenser threads (not shown) that correspond to eye drop bottle threads (not shown), or via other attachment means such as friction fit, a snap-lock configuration, a sliding cover, a spring-loaded cover, or the like or the like. Within the dispenser 30 resides the compression chamber 20, in this embodiment disc shaped, having the eye-port 22 oriented at a substantially perpendicular angle to the bottle-port 24, which allows propulsion of the drop (not shown) generally in the direction shown by arrow 74 towards the eye (not shown) substantially horizontal when the eye drop bottle is held upright. Note that any non-linear angle may be equally effective in this embodiment, while still allow the eye drop bottle to be held substantially vertical with respect to the direction of drop propulsion. It should be noted again in this embodiment, as is also the case for all other embodiments, the eye drop bottle (or container), as described herein, need not be fully or even partially vertical in operation, but only be oriented downward sufficient that at least a portion of the liquid retained therein accumulates in the nozzle for transmission to the compression chamber or dispenser, depending on the embodiment. The dispenser 30 is configured such that it attaches to the eye drop bottle 40 in a way that allows the bottle-port 24 to securely mate with the nozzle 42 (not marked) of the eye drop bottle 40. In this embodiment, the compressor 62 is a button configured to apply pressure to the compression chamber 20 when activated (i.e., depressed) and remove pressure when deactivated (i.e., released) as described above in operation to "load" fluid from the bottle into the compression chamber and then to "expel" fluid from the compression chamber via the dispenser aperture 34, respectively, to propel the drop towards the eye. The compressor 62 may return to its deactivated position based solely on decompression of the compression chamber pressure against the button, or be aided by a spring or other bias assembly connected to the compressor 62. In this embodiment, the retractor 82 is configured to act as the eye-port cover 50 that occludes the dispenser aperture 34 to load the fluid when the compressor is first depressed, then is removed when the drop is propelled upon the compressor being depressed a second time. As shown further with reference to FIGS. 6A-6C, the retractor 82 may also be configured to extend and retract the lower lid 88 downward so that the dispenser aperture 34 is aimed above the lower lid margin 90 and towards the lower conjunctiva and fornix 94. While in this position, the compressor 62 is activated (i.e., pressed), thereby propelling a drop towards the lower conjunctiva and fornix 94.

Figure 14C:
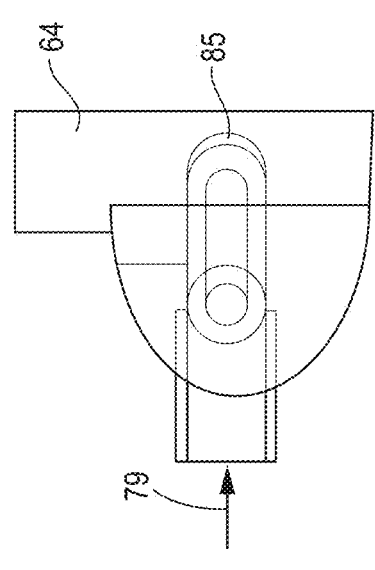
FIGS. 14A-14C show an enlarged view of a part of the retraction assembly of the eye drop propulsion device of FIG. 13.
Figure 14B:
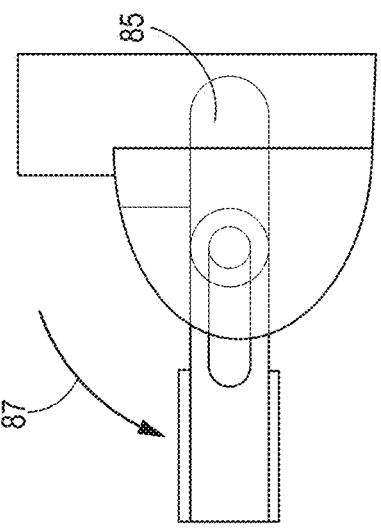
Figure 14A:
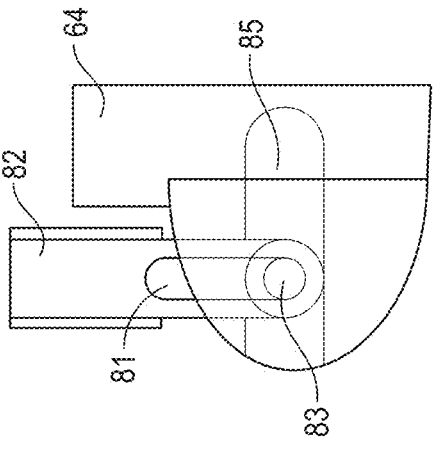

FIGS. 13A-13I show the operation of the eye drop propulsion device 10 of FIG. 12 with a modified retractor assembly 80 that is configured to lock the retractor 82 in an open position, preferably using a friction-based or snap-fit connection between the retractor and the dispenser. FIGS. 14A-14C show an enlarged view of a part of the retraction assembly of the eye drop propulsion device 10 of FIG. 13. As shown in particular with reference to FIGS. 14A-14C, the retractor assembly 80 includes a retractor slot 81 configured to rotate on a retractor axle 83 either connected to or integrally formed as part of dispenser 30. In operation, once the retractor 82 has rotatably moved towards a horizontal position generally in the direction shown by arrow 79, it can be pushed into a retractor slot 85 connected to or integrally formed as part of dispenser 30, generally in the direction shown by arrow 79, which locks it into position.

In FIG. 13A, the eye drop propulsion device 10 is inverted generally downwards (sufficiently aligned with gravity that liquid within the eye drop bottle is concentrated at the nozzle). In FIG. 13B, the compressor 62 is activated (depressed) generally in the direction shown by arrow 66, forcing air into the eye drop bottle generally in the direction shown by arrow 68. In FIG. 13C, the compressor is deactivated (released) generally in the direction shown by arrow 70, moving liquid from the eye drop bottle 40 into the compression chamber 20, generally in the direction shown by arrow 72. In FIG. 13D, the eye drop propulsion device 10 is returned to a generally upright position, and the retractor assembly 80 is rotated generally in the direction shown by arrow 87, or to a position generally aligning the dispenser aperture 34 with the eye (not shown), moving the retractor 82 and the eye-port cover and occlusion cap 54 away from the dispenser aperture 34. In one embodiment, as the retractor 82 moves away from the dispenser 30, the snap fit removably connecting the retractor 82 to the dispenser 30 is disengaged and the dispenser aperture 34 is opened. In FIG. 13E, the retractor 82 is pushed into the retractor slot 85 generally in the direction shown by arrow 79, which locks it in position In FIG. 13F, the compressor 62 is activated (depressed) generally in the direction shown by arrow 66, which propels a drop 98 from the dispenser aperture 34 towards the eye generally in the direction shown by arrow 74. In FIG. 13G, the compressor 62 is deactivated (released) generally in the direction shown by arrow 70, and air flows into the compressor chamber 20 generally in the direction shown by arrow 104 and the system returns to atmospheric pressure. In FIG. 13H, the retractor 82 is deactivated by pulling it out of the retractor slot 85 generally in the direction shown by arrow 78. In FIG. 13I, the retractor is rotationally moved back into its closed position generally in the direction shown by arrow 89, allowing the retractor 82, which functions as the eye-port cover 50 and/or occlusion cap 54, to occlude the dispenser aperture 34, preferably held in place with a snap fit as describe above, or the like.

Figures 15A, 15B, 15C:
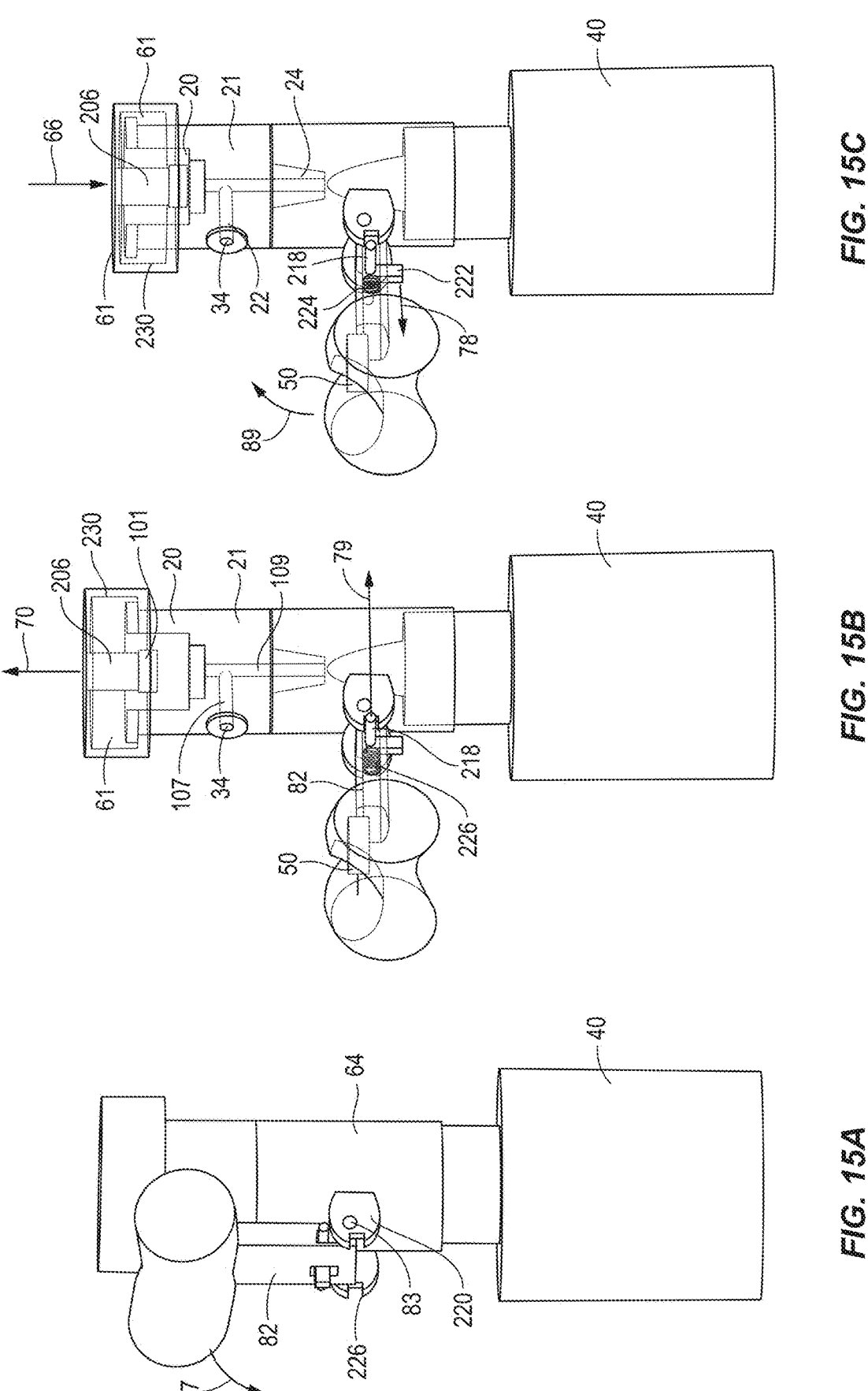
FIGS. 15A-15C show an eye drop propulsion device according to an embodiment of the present invention using a dual path, 3-pole configuration.
Figures 16A, 16B, 16C:
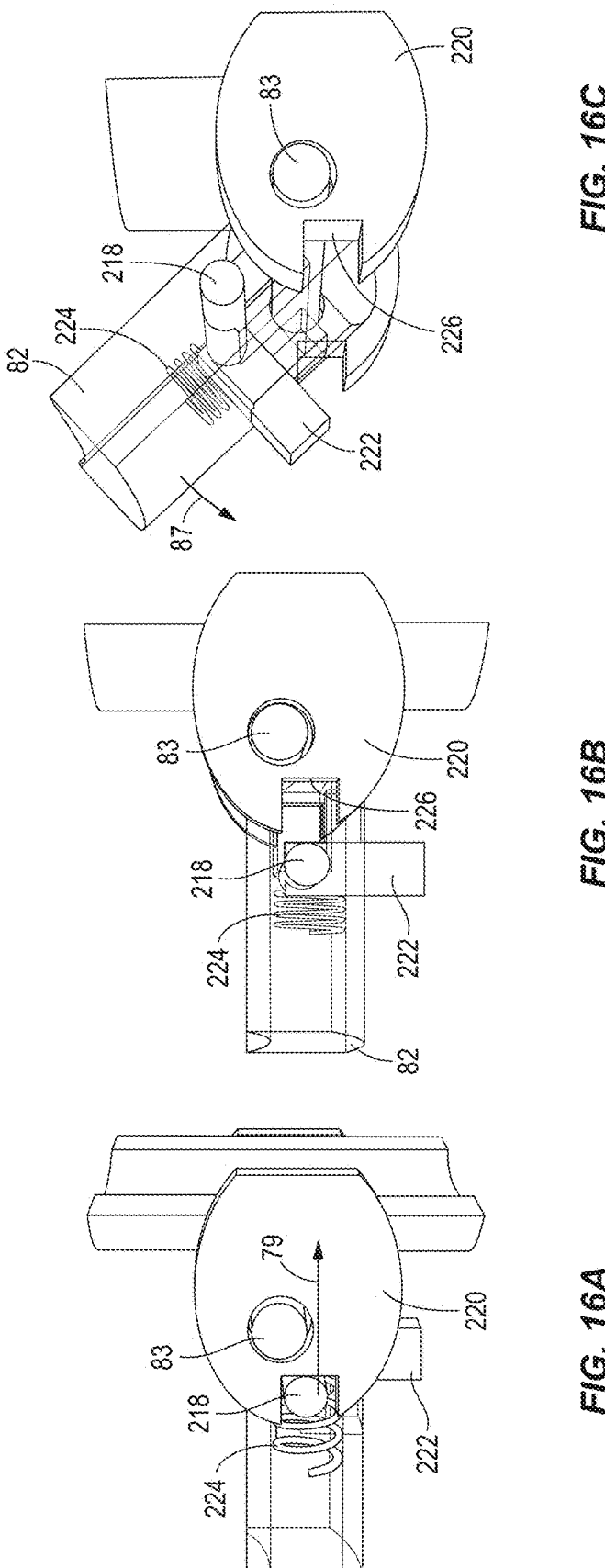
FIGS. 16A-16C show an enlarged view of a part of the retraction assembly of the eye drop propulsion device of FIG. 15.

FIGS. 15A-15C show an alternative embodiment of the present invention having a dual path, 3-pole configuration. This embodiment describes an alternative embodiment of a retractor assembly 80 with further reference to FIGS. 16A-16C. In FIG. 15A, the retractor axle 83 of the retractor assembly 80 is either connected to or integrally formed as part of the dispenser 30 or the housing 64, for example via a retractor flange 220. The retractor assembly further includes a spring-mounted retractor latch 218, a retractor latch tab 222, and a retractor latch spring 224. In this embodiment, the retractor 82 is configured to occlude the dispenser aperture 34, in one embodiment by use of an eye-port cover 50 and/or occlusion cap 54 that may be friction fit or snap-fit to the dispenser 30. As the retractor 82 is rotated away from the dispenser aperture 34 generally in the direction shown by arrow 87, the snap-fit of the eye-port cover 50 is released and the dispenser aperture 34 is opened. Referring to FIGS. 16A-16C, when the retractor 82 is in the substantially horizontal position, the retractor latch spring 224 forces the retractor latch 218 to advance into a retractor notch 226 in the retractor flange 220, which locks the retractor 82 into the activated position by movement generally in the direction shown by arrow 79. To rotate the retractor 82 back to the closed or substantially vertical position, the retractor latch tab 222 is pulled away from dispenser 30 to unlock generally in the direction shown by arrow 78, which in turn pulls the retractor latch 218 out of the retractor notch 226, and allows the retractor to rotate back to a more vertical position generally in the direction shown by arrow 89 to engage the snap-fit of the eye-port cover 50 to the dispenser aperture 34. FIGS. 15B-15C show the inner components of this embodiment, including the compression chamber 20 having the eye-port path extension 107 from the compression chamber to the dispenser aperture 34 and the bottle-port path extension 109 from the bottle-port to the compression chamber 20. The device further includes a plunger 100 attached to a plunger cover 230 having a flanged opening, configured to withdraw the plunger from the compression chamber a predetermined distance to draw liquid from the eye drop bottle into the compression chamber to load the device. To load the device with fluid, the device is substantially inverted and the plunger cover 230 pulled downwards. To activate the compressor assembly 60, the device is returned to its substantially non-inverted position and the plunger cover 230 is depressed generally in the direction shown by arrow 66 causing the plunger 100 to advance into the compression chamber 20 to propel a drop 98 from the dispenser aperture once loaded, as explained further below.

Figures 17A, 17B, 17C, 17D, 17E, 17F:
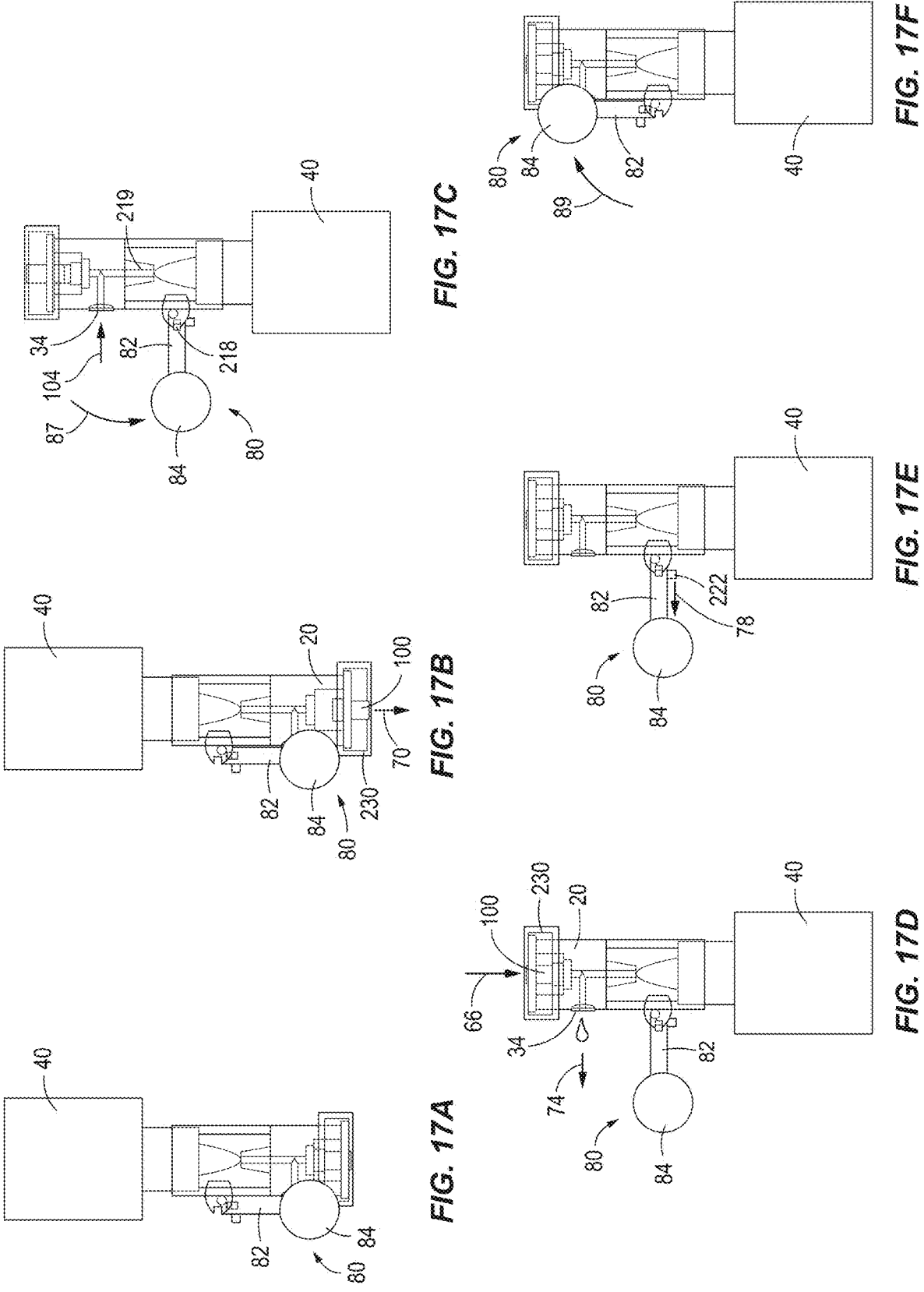
FIGS. 17A-17F show the operation of the eye drop propulsion device of FIG. 15.

FIGS. 17A-17F show the operation of the eye drop propulsion device 10 of FIG. 15. In FIG. 17A, the eye drop propulsion device including the eye drop bottle 40 is inverted or pointed generally downwards (sufficiently aligned with gravity that liquid within the eye drop bottle is concentrated at the eye drop bottle nozzle). In FIG. 17B, the plunger cap 230 is activated or pulled down generally in the direction shown by arrow 70, which pulls the plunger 100 out of the compression chamber 20 a predetermined distance, creating a vacuum in the compression chamber 20 and drawing fluid into the compression chamber 20. The plunger cap 230 is configured to prevent the plunger 100 from being pulled out of the compression chamber 20 more than the predetermined distance. In FIG. 17C, the device is return to its substantially upright orientation. Note that any non-linear angle may be equally effective in this or any other embodiment, while still allowing the eye drop bottle to be held substantially vertical with respect to the direction of drop propulsion to target the eye. The retractor is activated (e.g., rotated) generally in the direction shown by arrow 87, where the retractor latch 218 is forced into the retractor notch 226 in the retractor flange 220, which locks the retractor 82 in the activated position. The dispenser aperture 34 is now open and air flows into the compression chamber generally in the direction shown by arrow 104 to bring the system back to atmospheric pressure. In FIG. 17D, the plunger cap 230 is activated (e.g., depressed) generally in the direction shown by arrow 66, which pushes the plunger 100 into the compression chamber 20 and propels a drop 98 from the dispenser aperture 34 generally in the direction shown by arrow 74. In FIG. 17E, the retractor latch tab 222 is pulled away from the housing generally in the direction shown in arrow 78, which in turn pulls the retractor latch 218 out of the retractor notch 226, and allows the retractor 82 to rotate back to vertical position generally in the direction shown in arrow 89 to engage the snap-fit of the eye-port cover 50 to the dispenser aperture 34.

Figure 18A:
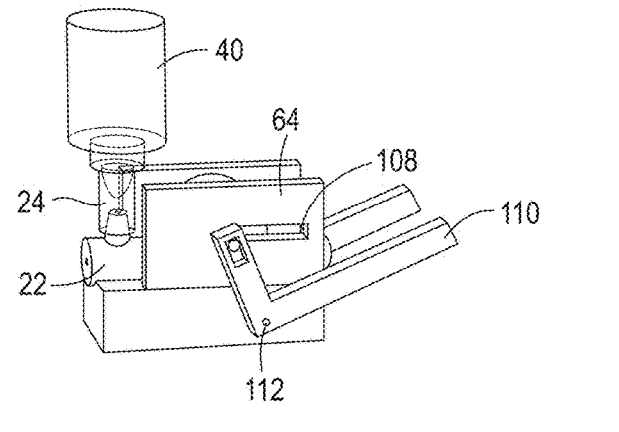
FIGS. 18A-18D show an eye drop propulsion device according to an embodiment of the present invention using a rolling pin compressor assembly.
Figure 18B:
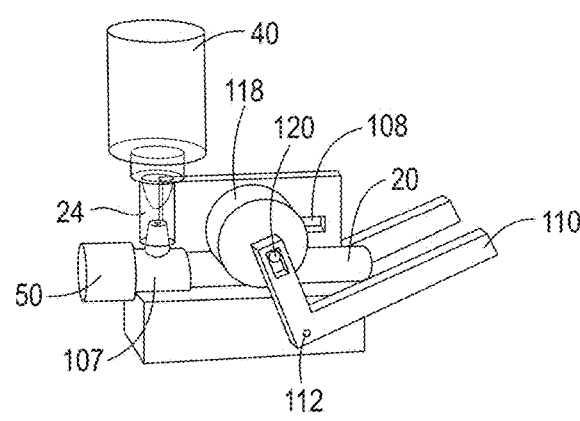

In an alternative embodiment shown with reference to FIGS. 18A-18D, the compressor assembly 60 uses a rolling disk as the compressor. FIGS. 18A-18B show an embodiment of the eye drop propulsion device 10 including the compression chamber 20, wherein the compression chamber 20 extends along the separate eye-port path extension 107 to the eye-port 22 connected to the dispenser 30 and the separate bottle-port path extension 109 to the bottle-port 24 connected to the eye drop bottle 40, and includes the eye-port cover 50 and/or occlusion cap 54. In this embodiment, the housing 64 has a lever slot 108, the housing supporting a compressor assembly 60 including a lever arm 110 configured to rotate on a lever axle 112. The embodiment further includes a rolling disk 118 configured to rotate on rolling disk axle 120, which pushes the disk along the compression chamber 20 forwards and backwards as the rolling disk axle 120 slides along in the level slot 108 as the lever arm 110 articulates with the rolling disk axle 120.

Figure 18C:
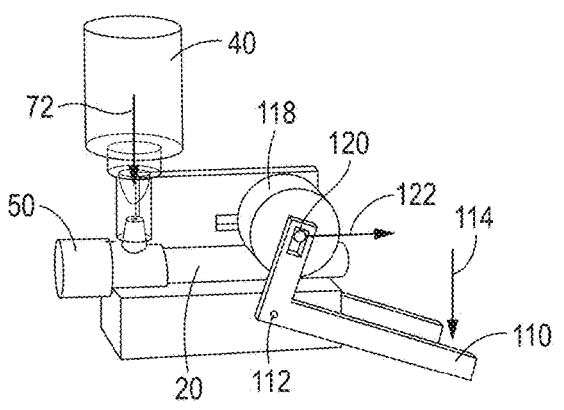
Figure 18D:
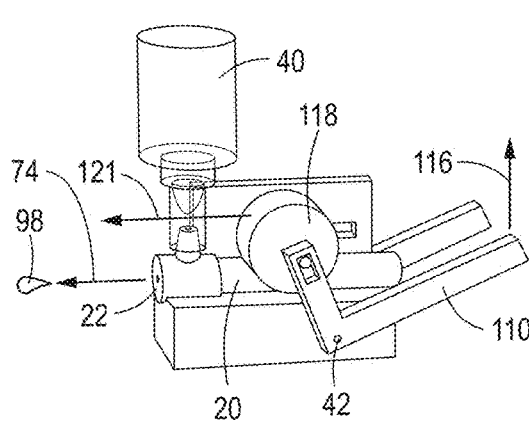
Figure 19C:
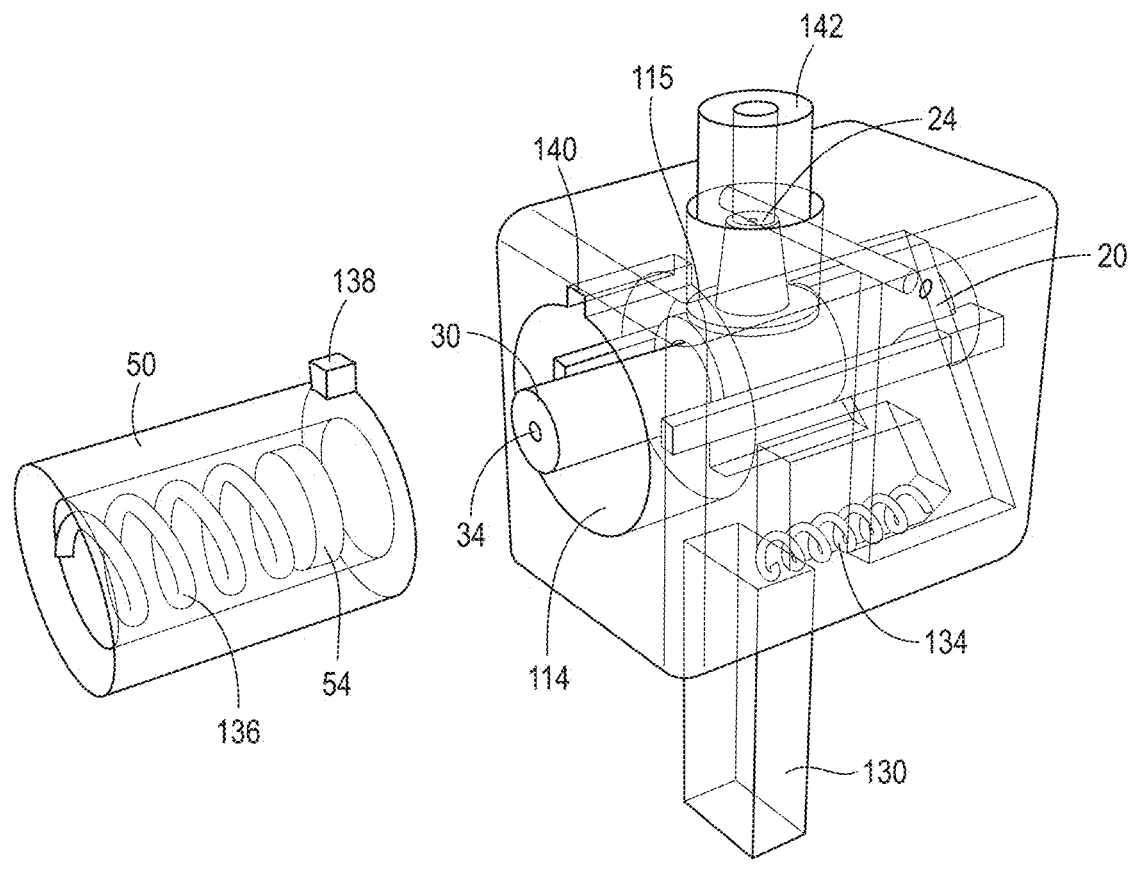
FIG. 19C shows an enlarged interior view of the eye drop propulsion device of FIGS. 19A-19B.
Figure 19D:
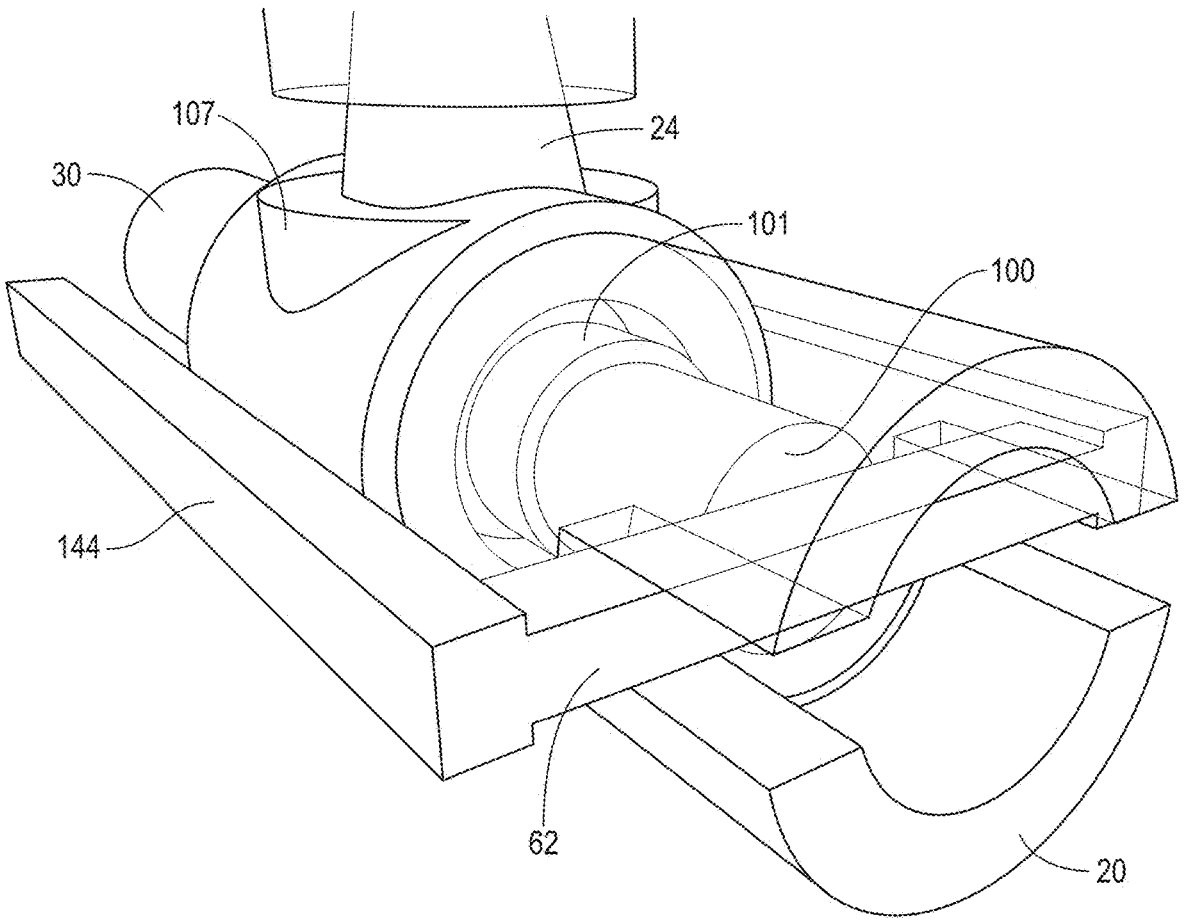
FIG. 19D shows an enlarged interior view of the plunger of the eye drop propulsion device of FIGS. 19A-19B.

FIGS. 18C-18D illustrates a preferred operation of the embodiment. As the lever arm 110 is pushed generally in the direction shown by arrow 114, it rotates on lever axle 112, which causes the rolling disk axle 120 and rolling disk 118 to roll generally in the direction shown by arrow 122 away from the eye-port 22, causing a vacuum in the compression chamber 20 and fluid to flow from the eye drop bottle 40 into the compression chamber 20. FIG. 18D shows the occluding eye-port cover 50 removed. As the lever arm 110 is pushed back generally in the direction shown by arrow 116, the rolling disk 118 is moved forward towards the eye-port 22 generally in the direction shown by arrow 121, which compresses the compression chamber 20 and causes a drop 98 to be propelled towards the eye (not shown) from the eye-port 22 generally in the direction shown by arrow 74.

In an alternative embodiment shown with reference to FIGS. 19-22, the compressor assembly 60 uses a spring-based compressor assembly. FIGS. 19A-19D show an embodiment of the eye drop propulsion device 10 including the compression chamber 20 having the eye-port 22 and the bottle-port 24 supported within a housing 64. The housing is preferably configured to further support the compressor assembly 60, which in this embodiment includes a stationary handle 130, a movable arm 132, and a compression spring 134 which together are configured to operate an actuator 144, moving it linearly to activate the compressor 62 as the movable arm 132 is depressed towards the stationary handle 130 to create a vacuum within the compression chamber 20.

The embodiment includes the dispenser aperture 34 along with the eye-port cover 50, which may be configured, for example, to be removably connected to the compressor assembly 60, compression chamber 20, or dispenser 30/housing 64, or some combination thereof, so long as it is able in operation to selectively occlude and open the dispenser aperture 34 to allow filling and expulsion of liquid from the compression chamber. In one embodiment, the eye-port cover 50 further includes an eye-port cap spring 136 attached to the occlusion cap 54, which compresses the occlusion cap 54 within the eye-port cover 50 to apply force against the dispenser aperture 34. In one embodiment, a cover flange 138 on the eye-port cover 50 is configured to mate with a correspondent housing groove 140 on the housing such when occlusion of the dispenser aperture is desired, the eye-port cover may be securely connected to the housing, for example via friction or twist-lock, and together with the cap spring 136 press the occlusion cap 54 against the dispenser aperture to occlude the aperture. In operation, once fluid is loaded into the compression chamber 20, the eye-port cover may be removed to open the dispenser aperture, allowing expulsion of the drop towards the eye. The eye drop bottle 40 is shown connected to the bottle-port 24 via the eye-port path extension of the compression chamber 20. In one embodiment, a bottle-port tube 142, preferably made of silicone, is configured to securely seal the nozzle 42 of the eye drop bottle 40 to the bottle-port 24 of the compression chamber 20. As more clearly shown with reference also to FIGS. 19C-19D, the compression chamber 20 is a syringe-like tube upon which is acted the plunger 100 when the compressor 62 is activated as the movable arm 132 is depressed towards the stationary handle 130. Specifically, as the plunger 100 is forced into the compression chamber 20, it causing an increase of pressure in the compression chamber, propelling liquid through the dispenser aperture 34.

The movement of fluid in this embodiment, and by extension similarly in principle to other embodiments of the present invention, is described with reference to FIG. 20. In FIG. 20A, the eye-port cover 50 and/or occlusion cap 54 comes in contact with and is positioned to occlude the dispenser aperture 34 (not shown) of the dispenser 30, which is connected to the compression chamber 20 via the eye-port path extension 107. In FIG. 20B, force is applied to the eye-port cover 50 and/or occlusion cap 54 generally in the direction shown by arrow 146, which in turn moves the actuators 144 (not shown) and the plunger 100, the latter of which is withdrawn at least in part from the compression chamber 20 generally in the direction shown by arrow 102, creating a vacuum and causing fluid to move out of the eye drop bottle 40 via the bottle-port 24 into the compression chamber 20, generally in the direction shown by arrow 72. In FIG. 20C, the eye-port cover 50 and/or occlusion cap 54 are removed, opening the eye-port 22 and dispenser aperture 34. This allows the pressure to equalize generally in the direction shown by arrow 104 in both the eye drop bottle 40 and the compression chamber 20. In FIG. 20D, and further with reference to FIG. 6, upon operation of the compression assembly 60 as the movable arm 132 is squeezed generally in the direction shown by arrow 148, the plunger 100 is moved towards the eye-port 22 and into the compression chamber 20 generally in the direction shown by arrow 106, creating positive pressure in the compression chamber and causing fluid to be expelled through the dispenser aperture 34 in the eye-port 22, specifically propelling typically the drop 98 generally in the direction shown by arrow 74 aimed above the lower lid margin 90 and towards the lower conjunctiva and fornix 94. Typically a small part of the liquid in the compression chamber 20 back into the eye drop bottle 40 generally in the direction shown by arrow 76.

Figure 21A:
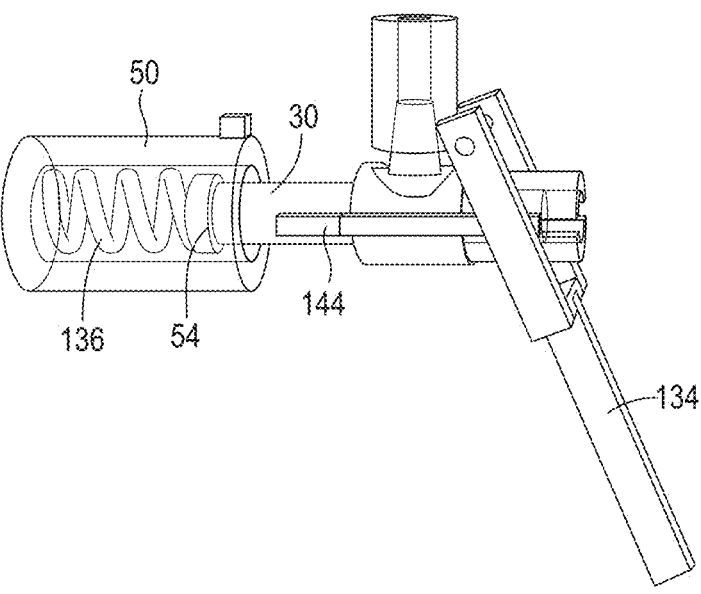
FIGS. 21A-21B show an eye drop propulsion device according to an embodiment of the present invention using a lever-based compressor assembly.
Figure 21B:
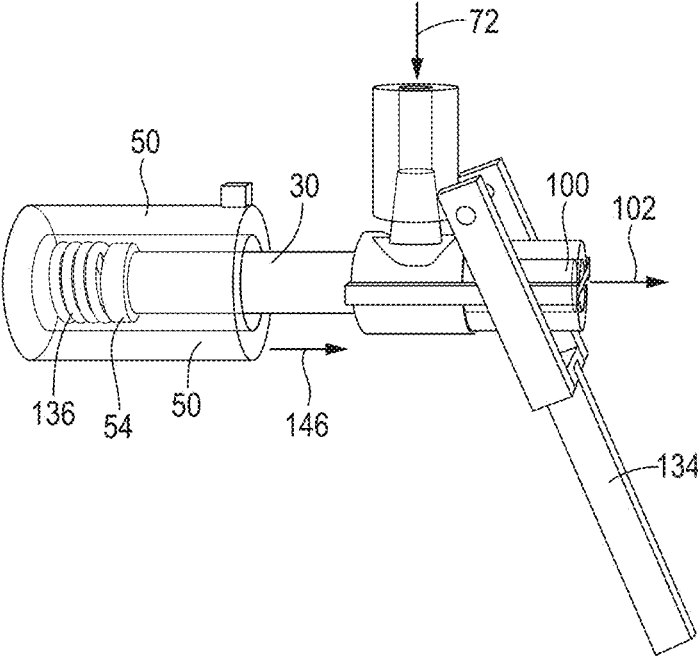

The operation of this embodiment is further described with reference to FIG. 21. More specifically FIGS. 21A-21B show the movement of the actuators by the eye-port cover 50 to load fluid into the compression chamber 20. As the eye-port cover 50 occludes the dispenser aperture 34, for example by connecting the eye-port cover 50 to the compressor assembly 60, the compression chamber 20, dispenser 30, housing 64, or some combination thereof, the occlusion cap 54 is pushed against the dispenser aperture 34 by the cap spring 136, thereby occluding the dispenser aperture 34. As the cover advances, the occlusion of the dispenser aperture 34 is maintained by the compression of the cap spring. Moreover, as the cover is pushed further towards the eye-port 22, the actuators 144 are pushed away from the eye-port 22 generally in the direction shown by arrow 146, resulting in the plunger 100 of the compression chamber 20 moving away from the eye-port 22 generally in the direction shown by arrow 102, causing a vacuum within the compression chamber that draws fluid into the compression chamber from the eye drop bottle 40 via the bottle-port 24.

Figures 22A, 22B:
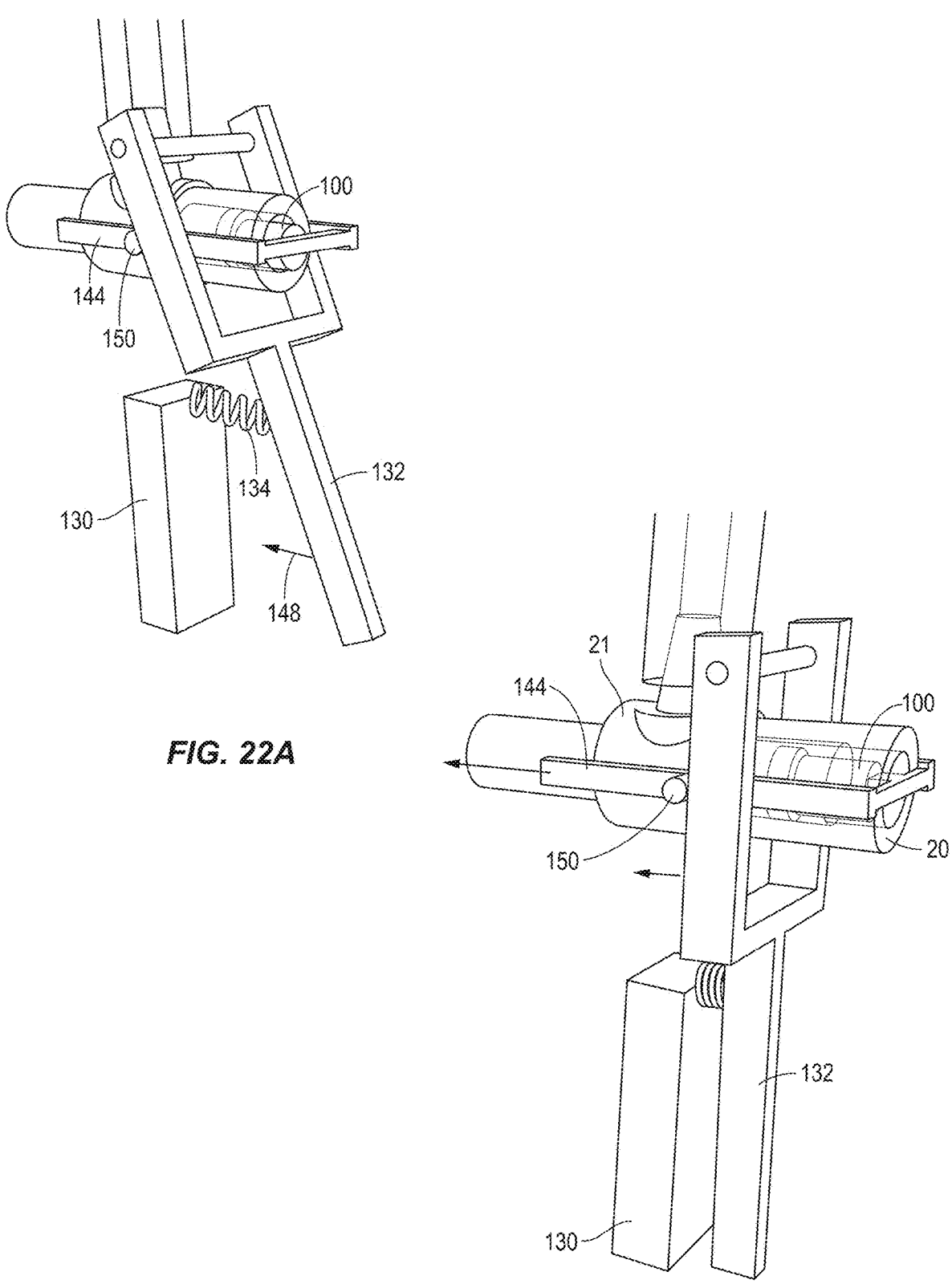
FIGS. 22A-22B show the operation of the eye drop propulsion device of FIGS. 21A-21B.

More specifically with reference to FIG. 22, the operation of dispensing the drop 98 towards the eye 86 is shown. FIGS. 22A-22B shown the exemplary embodiment with fluid loaded in the compression chamber 20 and the eye-port cover 50 removed such that the dispenser aperture 50 is no longer occluded. As the movable arm 132 is forced or squeezed towards the stationary handle 130, generally in the direction shown by arrow 148, it moves the actuators 144, in one example shown by engaging one or more actuator protrusions 150, which in turn moves the plunger 100 into the compression chamber 20 to expel typically a drop of fluid (not shown) from the compression chamber 20 through the eye-port path extension 107 into the dispenser aperture 34 towards the eye (not shown).

Figure 23A:
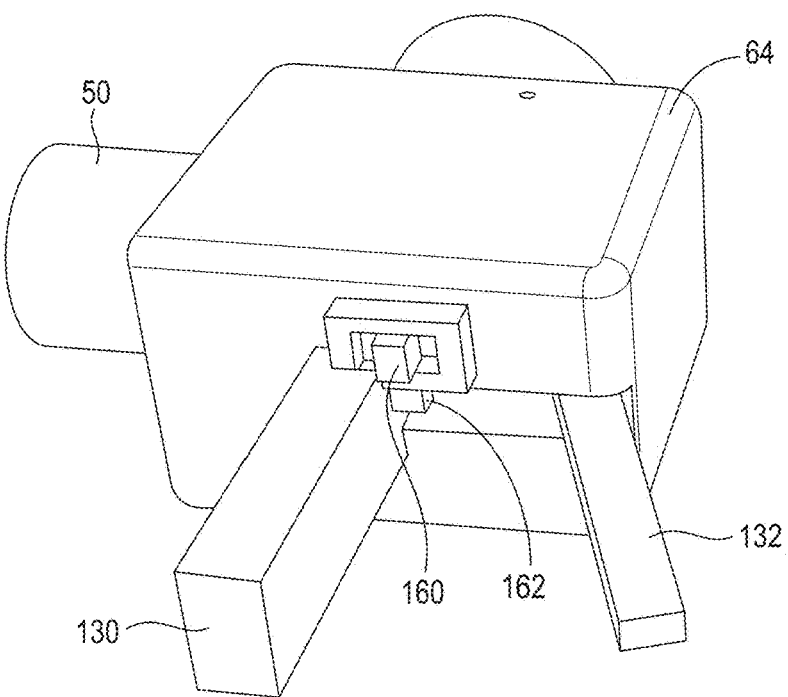
FIGS. 23A-23B show an eye drop propulsion device according to an embodiment of the present invention using a ratchet compressor assembly.
Figure 23B:
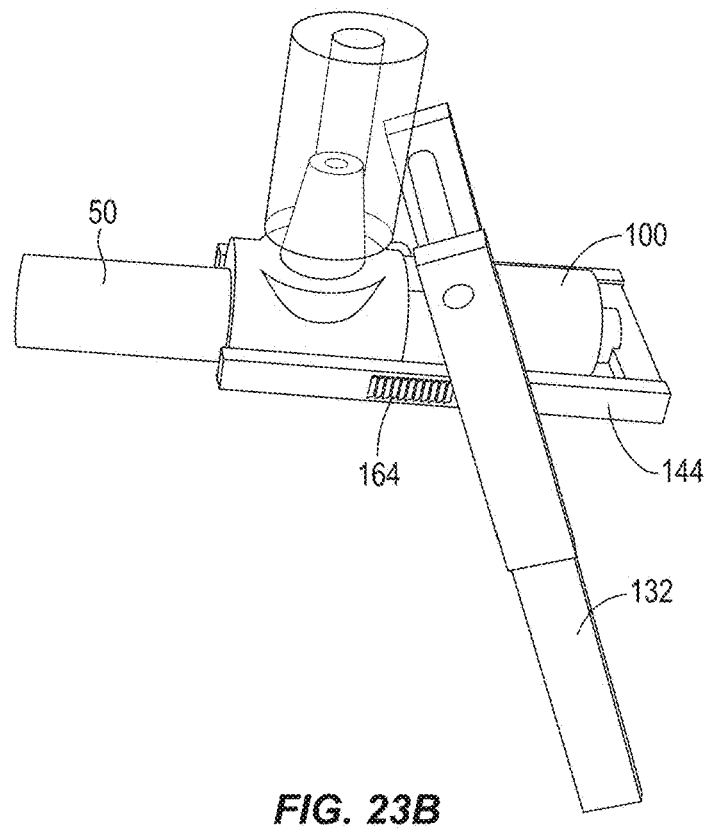

In an alternative embodiment shown with reference to FIGS. 23, a sliding tab 160 and slider flange 162 is configured to limit the distance that the movable arm 132 and therefore the plunger 100 can move, allowing modification of the size of the drop 98. The compressor assembly 60 may also use a modified ratchet mechanism compressor assembly.

Figures 24A, 24B, 24C, 24D, 24E, 24F:
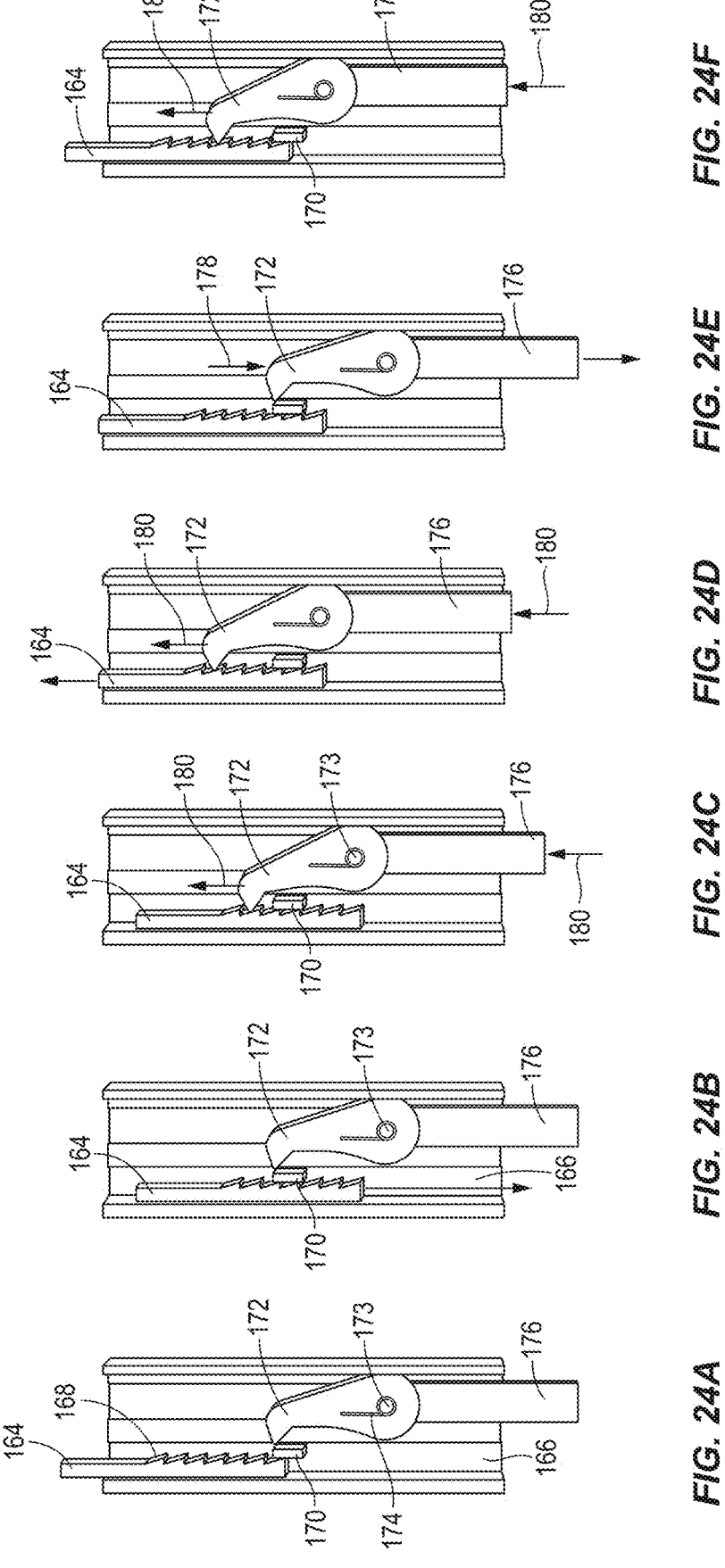
FIGS. 24A-24F show the operation of an exemplary eye drop propulsion device using a ratchet compressor assembly.

With reference to FIGS. 24A-24F, which illustrated operation of a variable ratchet embodiment, a ratchet 164 is configured limit the movement of the plunger 100 so that it advances forward incrementally into the compression chamber with each squeeze of the movable arm 132 so that a drop can be delivered to each eye without having to reload. In this embodiment, the compression chamber 20 the compressor assembly 60 and the housing 64, or some combination thereof, supports a variable ratchet 164 with ratchet teeth 168 which moves forward incrementally in a ratchet track 166. The variable ratchet 164 is attached to the plunger 100 and is configured to move the plunger forward into the compression chamber in increments each time the movable arm 132 is squeezed, thus allowing the patient to deliver a drop to each eye without having to reload the device. The variable ratchet 164 engages with a pawl 172, which is attached to a ratchet arm 176 by means of a pawl axle 173. A pawl spring 174, preferably a torsion spring, exerts a rotational force towards the variable ratchet 164. The ratchet arm is in turn attached engages the actuator by means of the actuator protrusion 150 (not shown). A pawl lift 170 disengages the pawl 172 from the ratchet teeth 168 as the pawl 172 moves over it. FIG. 24A shows the position of the variable ratchet 164 and the pawl 172 when the plunger 100 is fully advanced into the compression chamber 20 (not shown) and the eye-port cover 50 removed (not shown). FIG. 24B shows the positions after the eye-port cover 50 is in place, with the actuator 144 having moved the plunger out of the compression chamber 20 to fill the chamber. The variable ratchet 168 is able to move past the head of the pawl since the pawl lift 170 has disengaged the rachet teeth 168. FIGS. 24C-24D show the positions after the first squeeze of the movable arm 132 (not shown). The pawl 170 advances past the pawl lift 170 engages the rachet teeth 168, and advances the variable rachet 164 half the distance, thus advancing the plunger 100 halfway into the compression chamber 20, leaving it half full to dispense another drop without reloading. FIGS. 24E-24F show the positions after the release of the movable arm 132 (not shown). The pawl moves over the pawl lift 170, and then re-engages the ratchet teeth, to advance the variable ratchet 164 and the plunger 100 fully into the compression chamber 20 (not shown) to propel the second drop without having to reload.

It will be readily appreciated that the above-described ratcheting mechanism is only one of a wide range of similar mechanisms that can be used to alter the movement of the compression assembly 60 to modify the compression in the compression chamber 20, and thereby change the amount of fluid drawn or loaded into the compression chamber as well as the resulting number of drops that may be expelled in operation before reloading the compression chamber is required. For example, a ball point pen type mechanism could be configured to produce a repeatable two-step advancement of the movement of the plunger into the compression chamber, or a means to modify the compressor size to modify the drop. Similarly, while the preceding embodiment disclosed expelling two drops (e.g., one into each of a typical user's two eyes), modification of the variable ratchet 164 could readily be done using these same principals to change the number of drops from two to three, four or more, depending on the size and configuration of the compression chamber 20.

Figure 25E:
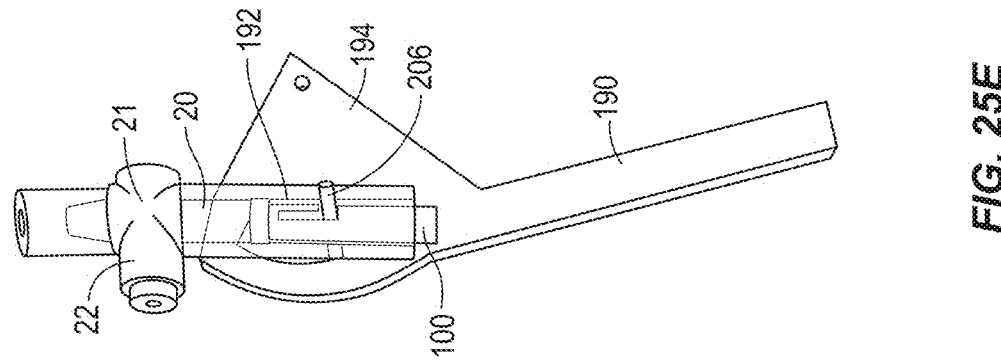
Figure 25D:
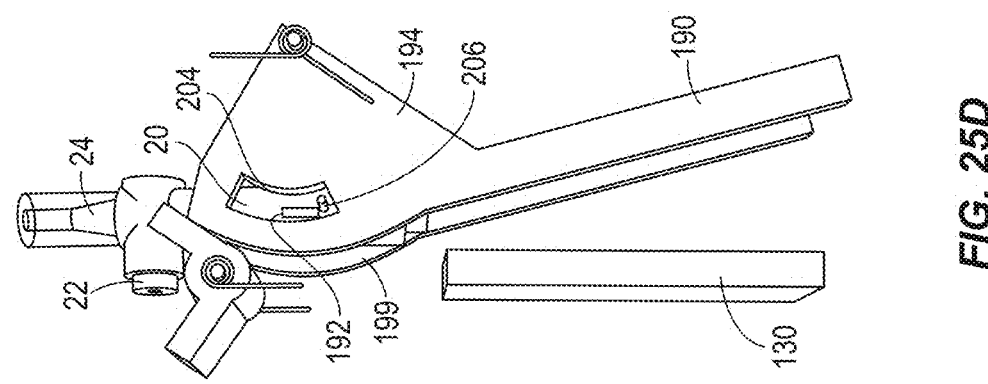
Figure 25C:
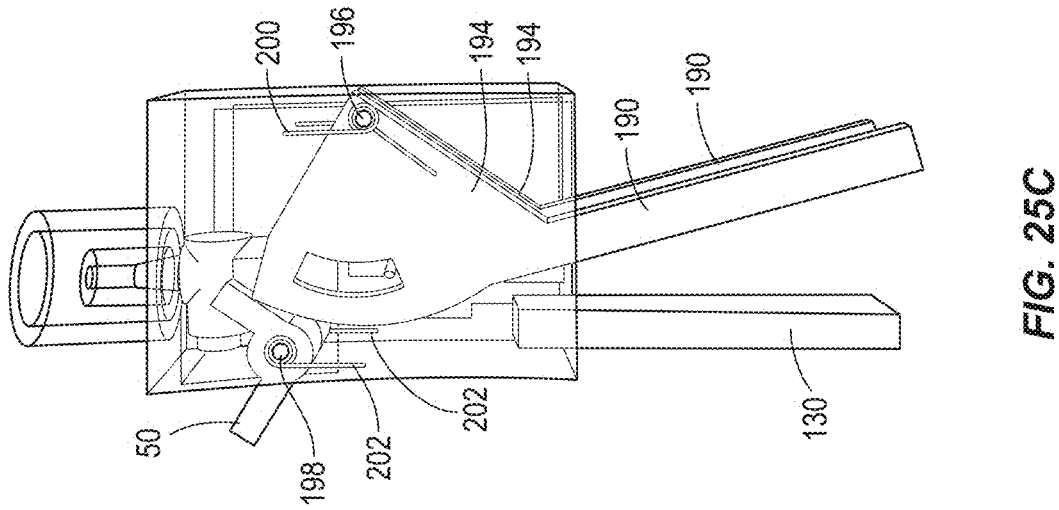

An alternative embodiment is shown with reference to FIGS. 25-27. This embodiment is configured to automatically cover and uncover the eye-port 22 and fill or load and discharge the compression chamber 20 in a single operation of the compressor assembly 60. In one embodiment, described with reference to FIGS. 25A-25E, the dispenser 30 supports the eye drop bottle 40 and facilitates connection between the eye drop bottle 40 and the compression chamber 20, for example via dispenser threads (not shown) that correspond to eye drop bottle threads (not shown), or via other attachment means such as friction fit, snap-lock configuration, or the like. Within the dispenser 30 resides the compression chamber 20, the eye-port path extension 107 connected to the eye-port 22 and dispenser aperture 34 and the bottle-port path extension 109 connected to the nozzle 42 of the eye drop bottle 40. In this embodiment the bottle-port 24 is generally vertically oriented to receive the eye drop bottle 40, while the eye-port 22 is generally horizontally oriented such that the dispenser aperture 34 can be readily aligned with the eye (not shown). Note that any non-linear angle may be equally effective in this or any other embodiment, while still allowing the eye drop bottle to be held substantially vertical with respect to the direction of drop propulsion to target the eye. The compressor assembly 60 includes the stationary handle 130 and the movable arm 132, shown here having two optional extensions 190, which are connected to the dispenser 30 and/or housing 64. This embodiment further includes the eye-port cover 50 and occlusion cap 54 connected to eye-port cover lever 208, which is hinged such that in the closed position the eye-port cover and/or occlusion cap 54 occlude the dispenser aperture 34. FIG. 25A shows the eye-port cover 50 in the closed position, wherein occlusion cap 54 (not shown) occludes the dispenser aperture 34. FIG. 25B shows the eye-port cover 50 in one of several open positions after the movable arm 132 is operated, which opens the dispenser aperture 34 to allow expulsion of the drop.

The compressor assembly 60 is configured to engage both the compression chamber 20 to load and discharge typically the drop, but also to, in the same action, open the eye-port cover 50 to discharge the fluid from the compression chamber 20, and then to close to load fluid into the compression chamber 20. In a preferred embodiment, the compression chamber 20 includes a vertical slot on at least one side of the chamber, shown here as vertical slots 192. As shown more specifically further with reference to FIGS. 25C-25E, the movable arm 132 and movable arm extensions 190 include at least one preferably pie-shaped head 194 that rotate on a movable arm axle 196 supported by the housing 64 as the movable arm extension(s) 190 are squeezed towards the stationary handle 130. Movable arm springs 200, preferably torsion springs, are attached to the at least one pie-shaped head 194 to exert rotational force to push the movable arm 132 away from the stationary handle 130. The eye-port cover 50 and/or occlusion cap 54 are configured to rotate on an eye-port cover axle 198 supported by the dispenser 30 and/or housing 64 with eye-port cap springs exerting rotational force to close and occlude the eye-port. As the movable arm extension(s) 190 are squeezed towards the stationary handle 130, the pie shaped head 194 pushes against the eye-port cover 50 and against the force of the eye-port cap spring 202 to open the eye-port 22. In this embodiment, the movable arm 132 is configured with at least one curved slot 204 aligned with the at least one vertical slot 192. By way of example, FIGS. 25C-25E show two pie-shaped heads 192, 192' that have two movable arm rounded slots 204, 204' that are aligned with two vertical slots 192, 192' on each side of the compression chamber 20. This embodiment further includes a plunger rod 206 connected to the plunger 100, wherein the plunger rod is configured to move within the vertical slot(s) 192 and movable arm curved slot(s) 204 as the movable arm 132 is squeezed and corresponding pie-shaped head 194 rotates in operation, which compresses and decompresses the compression chamber 20 to "load" fluid from the bottle into the compression chamber and then to "expel" fluid from the compression chamber via the dispenser aperture 34, respectively, to propel the drop towards the eye.

FIGS. 26A-26D provide further details illustrating this embodiment as the movable arm 132 is squeezed, preferably using at least one movable arm extension 190. FIG. 26A shows the position before the movable arm 132 is squeezed. The eye-port cover 50 is in the closed position, with its occluding cap 54 pressed against the dispenser aperture 34 and the eye-port cover lever 208 projecting posteriorly and above the pie-shaped head 194. The plunger rod 206 is positioned at the top of the of the movable arm curved slot 204 of the pie-shaped head 194 and at the bottom of the vertical slot(s) 192 of the compression chamber 20 and the plunger (not shown) is positioned at the lower end of the compression chamber 20. In FIG. 26B, as the movable arm 132 is forced or squeezed towards the stationary handle 130 generally in the direction shown by arrow 148, it rotates the pie-shaped head 194 to engage the eye-port cover lever 208. In FIG. 26C, continued force of the movable arm 132 causes the eye-port cover 50 to rotate generally in the direction shown by arrow 210, moving the eye-port cover 50 and occlusion cap 54 away from the dispenser aperture 34. The plunger rod 206 is now positioned at the bottom of the movable arm curved slot 204 of the pie-shaped head 194, and at or near the bottom of the vertical slots 192 of the compression chamber 20. In FIG. 26D, the movable arm 132 completes its rotation, causing the lower edge of the movable arm curved slot 204 to push the plunger rod 206 upward, in turn causing the plunger (not shown) to compress the compression chamber 20, resulting in the drop 98 being expelled from the dispenser aperture 34 towards the eye 86 generally in the direction shown by arrow 74.

Figure 27A:
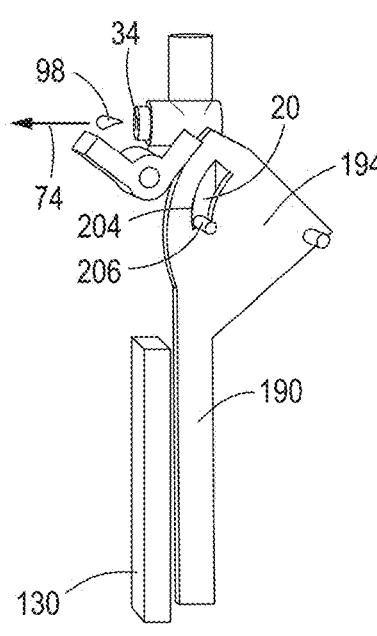
FIGS. 27A-27D show the operation of the eye drop propulsion device of FIGS. 25A-25E when force is released from the compressor assembly.
Figure 27B:
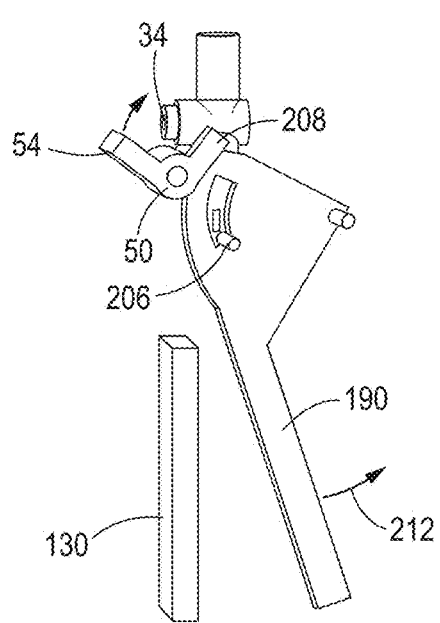
Figure 27C:
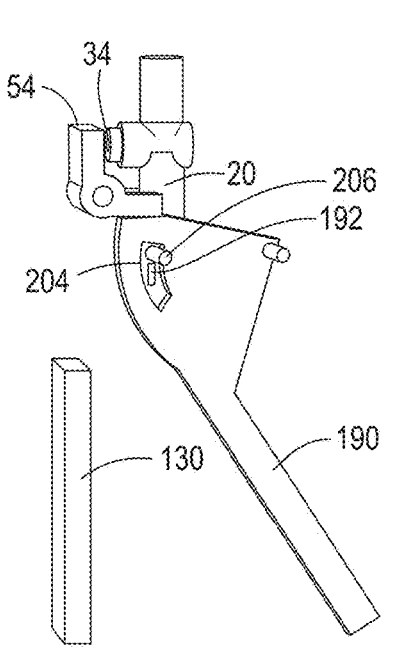
Figure 27D:
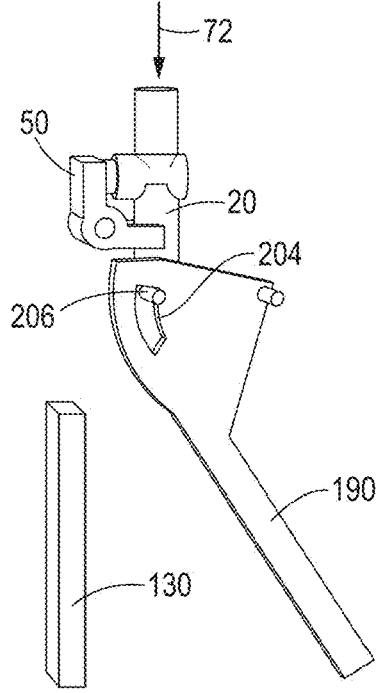

FIGS. 27A-27D provide further details illustrating this embodiment as the movable arm 132 is released. FIG. 27A shown a similar position as described with reference to FIG. 26D above, wherein the movable arm 132 is fully squeezed, for example after having just expelled the drop 86. FIG. 27B shows the force on the movable arm 132 starting to be released generally in the direction shown by arrow 212, which moves the rotating arm (and in this example the movable arm extension 190) away from the stationary handle 130 due to the countervailing force of movable arm spring(s) 200, and further releases the force on the eye-port cover lever 208, which thereby moves the eye-port cover 50 back towards the dispenser aperture 34 due to the force generated by the eye-port cap spring(s) 202. FIG. 27C shows that the further rotation moves the eye-port cover 50 and occlusion cap 54 to fully occlude the dispenser aperture 34, and moves the plunger rod 206 (216) to a position near or at the top edge of the movable arm curved slot 204, also at or near top of the vertical slot(s) (not shown) of the compression chamber 20. In FIG. 27D, as the movable arm 132 rotates back to its final position, the top edge of the movable arm curved slot 204 forces the plunger rod 206 to decompress the compression chamber 20, causing a portion of liquid in the eye drop bottle (not shown) to flow into the compression chamber 20 generally in the direction shown by arrow 72.

Figure 28A:
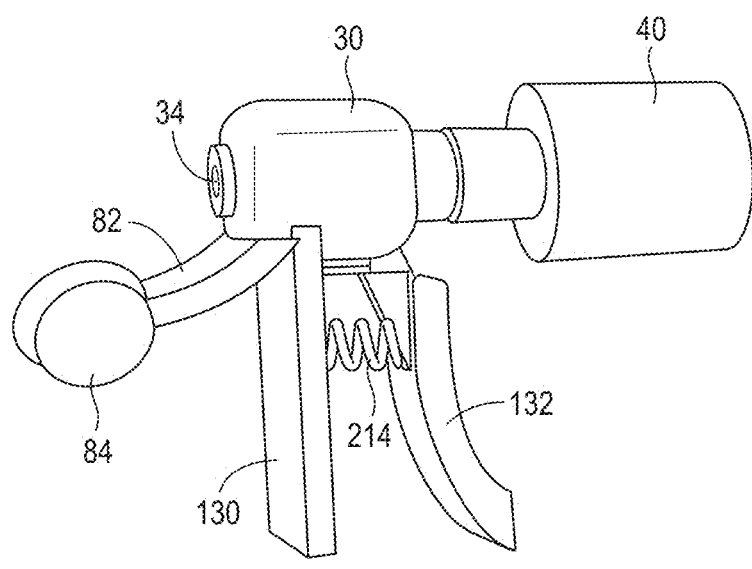
FIGS. 28A-28B show an eye drop propulsion device according to an embodiment of the present invention using a lever-based compressor assembly and including a retractor assembly.
Figure 28B:
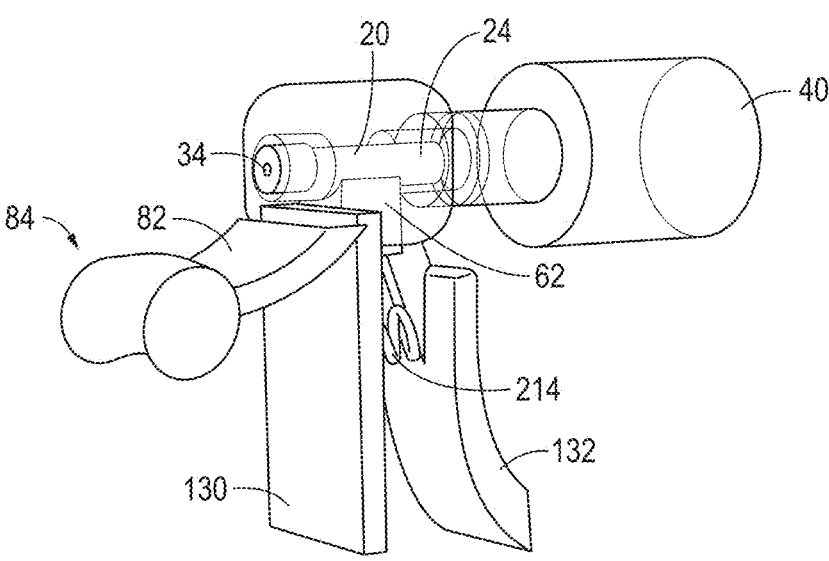
Figures 29A, 29B, 29C, 29D, 29E, 29F:
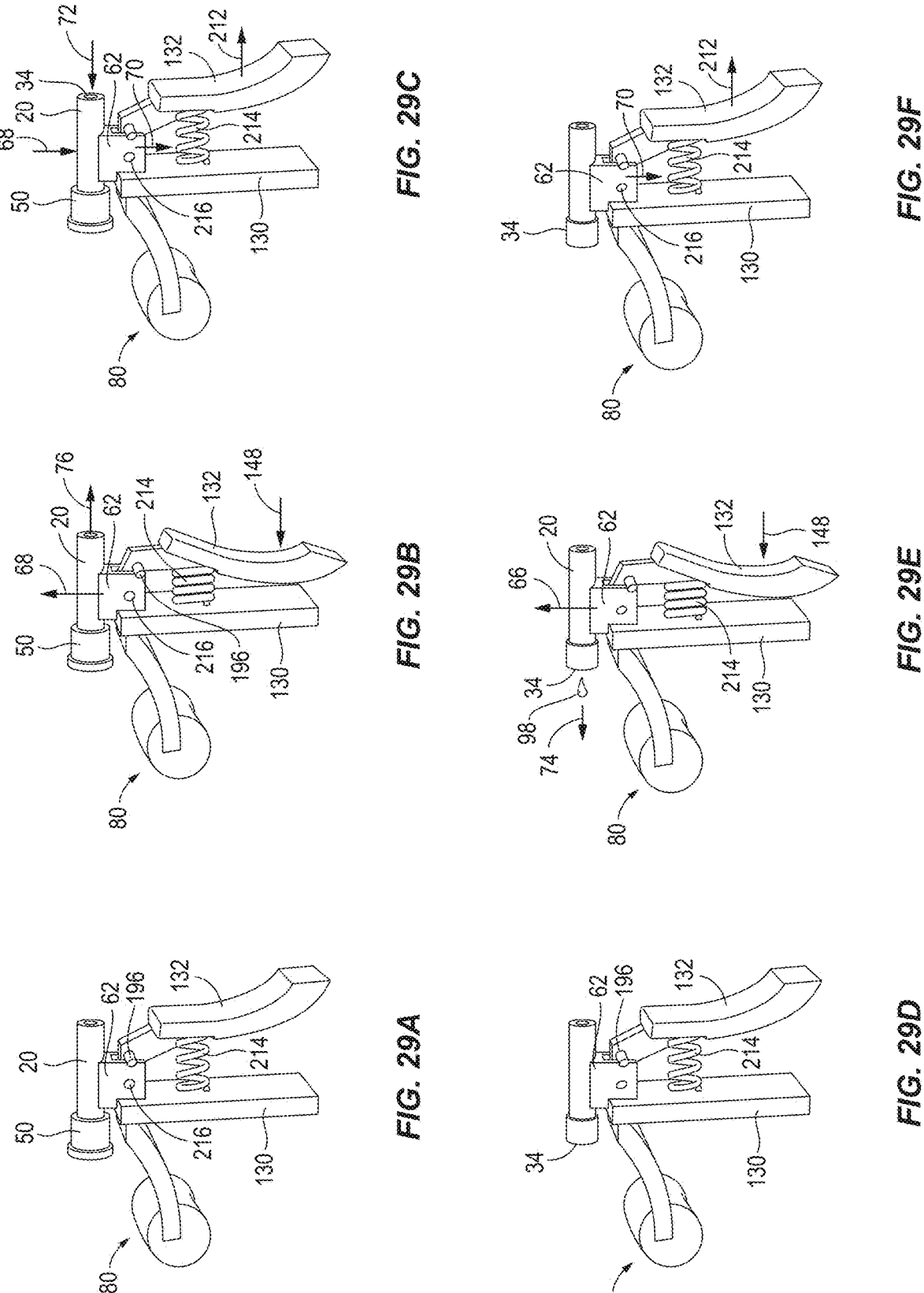
FIGS. 29A-29F show the operation of the eye drop propulsion device of FIGS. 23A-23B.
Figure 30:
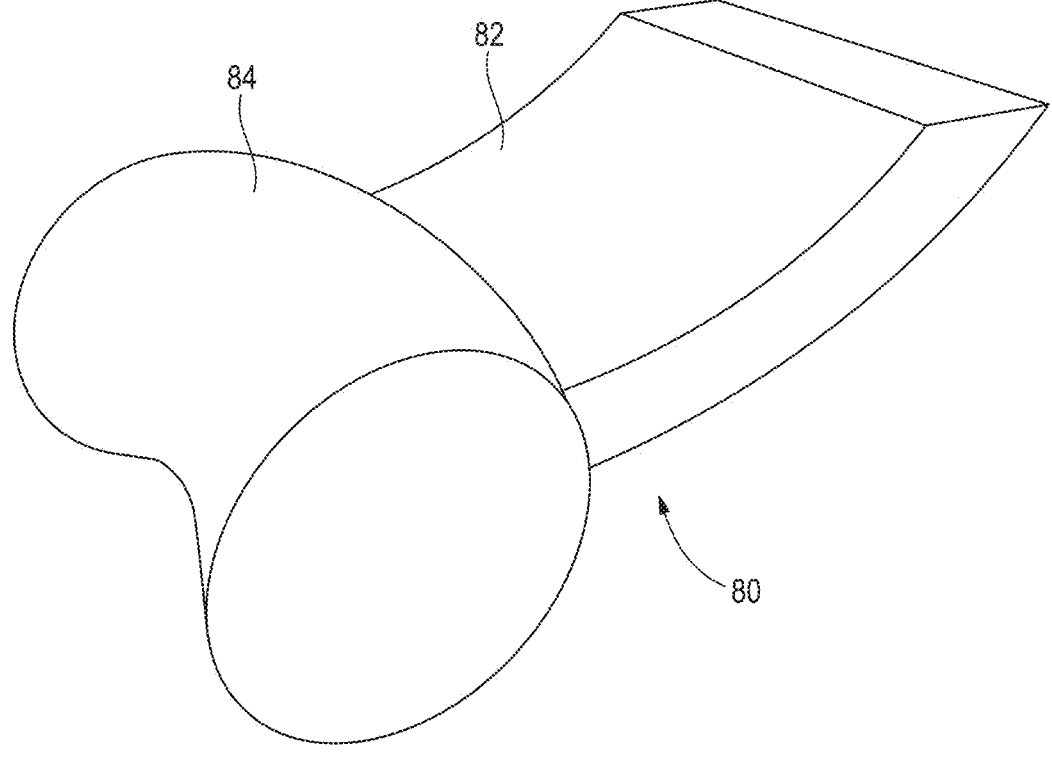
FIG. 30 shows an enlarged view of the optional retractor assembly of a variation of the eye drop propulsion device of FIGS. 28A-28B.

As shown with reference to FIGS. 28-30, an alternative embodiment of the present invention includes a retractor assembly 80 having the retractor 82 and the retractor pad 84, in this example configured to permanently extend from the dispenser 30 (which may or may not further include a housing 64) having the dispenser aperture 34, and the compression chamber 20. The nozzle 42 of the eye drop bottle 40 is attached to the bottle-port 24 of the eye drop bottle 40 preferably in a removable fashion, for example by friction fit, screwed into threads on the nozzle or bottle corresponding to threads in the bottle-port, or the like, but may also be secured in a non-removable fashion, for example by glue, manufacturing the tube to the nozzle, or the like. FIG. 28A show the eye-port cover 50 in place occluding the dispenser aperture 34, which may be held in place via friction, threads (not shown), or the like. As shown further with reference to FIG. 28B, the compressor assembly 60 includes the stationary handle 130, the movable arm 132, and a handle spring 214 configured to bias the movable arm away from the stationary handle in its natural position (shown in FIG. 28A) to a compressed position (shown in FIG. 28B), in which the movable arm 132 is forced or squeezed towards the stationary handle 130 against the tension of the handle spring 214. The compressor assembly 60 also includes the compressor 62, connected to the movable arm 132, which is configured to compress or decompress the compression chamber 20 upon movement of the movable arm 132.

The structure, functionality and operation of this embodiment is further described with reference to FIGS. 29A-29F, which shows the two-step loading and expelling of at least one drop of fluid towards an eye. The first or loading step is described with reference to FIGS. 29A-29C. FIG. 29A shows the eye-port cover 50 in place occluding the compression chamber 20. The movable arm 132 rotates on movable arm axle 196, which may be supported by dispenser 30 or housing 64 (not shown), which is configured to apply pressure to the compression chamber 20 via the compressor 62. In FIG. 29B, the movable arm 132 is forced or squeezed generally in the direction shown by arrow 148, against the tension of handle spring 214, which causes the compressor 62 to move against the compression chamber 20 generally in the direction shown by arrow 68, thereby compressing the compression chamber and forcing air into the eye drop bottle 40 generally in the direction shown by arrow 76 In one alternative embodiment shown, a compressor axle 216 may be used to allow the compressor 62 to remain parallel to the compression chamber 20 as the movable arm 132 rotates on movable arm axle 196. In FIG. 29C, the movable arm 132 is released, and the tension of handle spring 214 moves the movable arm 132 generally in the direction shown by arrow 212, allowing the compressor 62 to move away from the compression chamber 20 generally in the direction shown by arrow 70, which causes the compression chamber 20 to create a negative pressure to draw fluid from the eye drop bottle 40 through the bottle-port 24 into the compression chamber 20, generally in the direction shown by arrow 72, thereby loading fluid into the compression chamber 20.

The second or expelling step is described with reference to FIGS. 29D-29F. In FIG. 29D, the eye-port cover 50 is shown removed, revealing the dispenser aperture 34. In FIG. 29E, the movable arm 132 is forced or squeezed generally in the direction shown by arrow 148, against the tension of handle spring 214, which causes the compressor 62 to move against the compression chamber 20 generally in the direction shown by arrow 66, thereby compressing the compression chamber and propelling preferably the drop 98 from the dispenser aperture 34 towards the eye 86 generally in the direction shown by arrow 74. FIG. 29F shows the movable arm 132 released, causing the tension of handle spring 214 to move the movable arm 132 generally in the direction shown by arrow 212, allowing the compressor 62 to move away from the compression chamber 20 generally in the direction shown by arrow 70 to is original position. The handle spring 214 also diminishes or prevents any slight pressure on the moveable arm 132 when it is being held from causing leakage from the dispenser aperture 34.

FIG. 30 shows an enlarged view of the optional retractor assembly 80, which includes the retractor 82 and the retractor pad 84. It is preferably configured to naturally fit in the infraorbital area (the soft tissue just below the lower lid). The diameter of the retractor pad 84 should preferably approximate the diameter of an index finger. There are two curves, one parallel to the horizontal plane and one parallel to the vertical plane. The contact member rotated along its long axis so that it is angled downwards and towards the eye. This size and geometry allow the patient to effortlessly position the device, comfortably support the device, and retract the lower lid. Placement is made easier by having the patient initially place the contact member on the upper cheek and then sliding the retractor pad 84 upwards to until it encounters the lower lid 88. Additional embodiments might include an adjustable retractor 82 or retractor pad 84 to move the position of the retractor pad 84 up or down slightly to fine-tune the line-of-fire to accommodate a varying periocular anatomy.

Figure 31A:
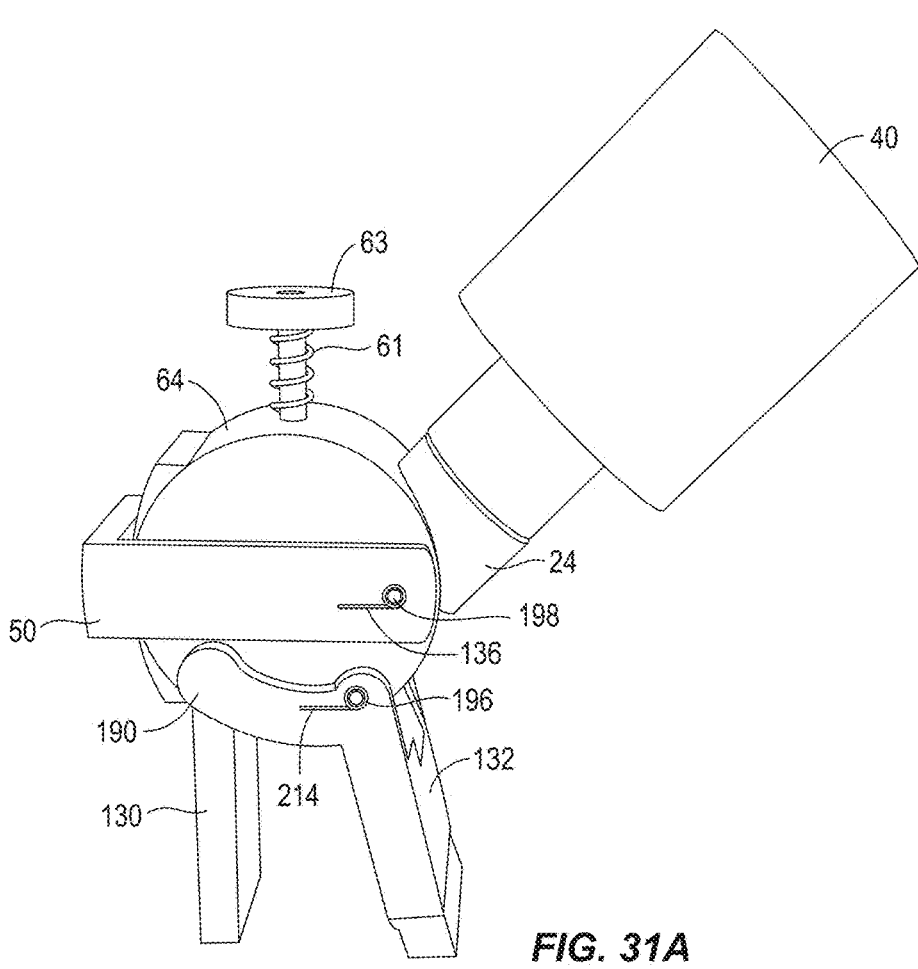
FIGS. 31A-31C show an eye drop propulsion device according to an embodiment of the present invention illustrating a variation of the eye drop propulsion device of FIG. 28 having a retractable retractor assembly.
Figure 31B:
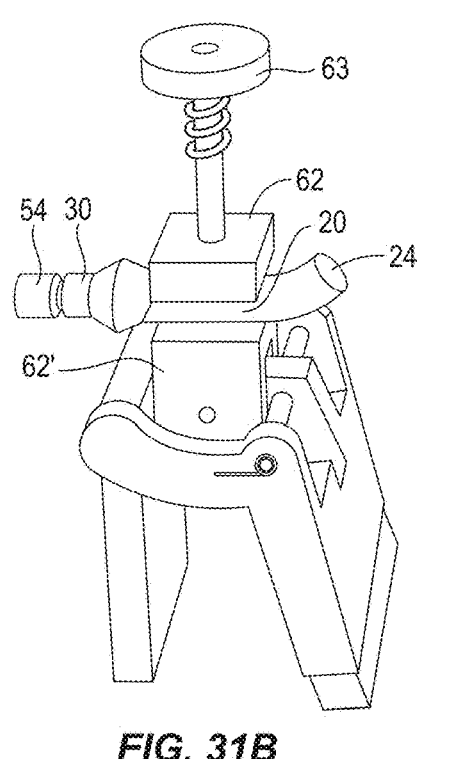
Figure 31C:
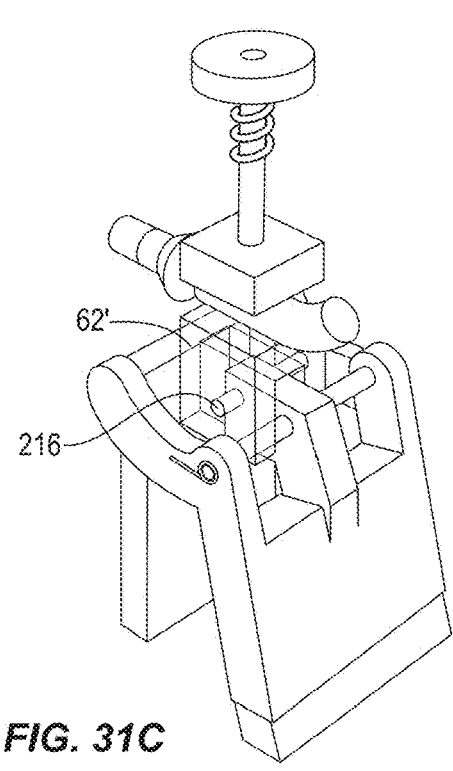

FIGS. 31A-31C show an eye drop propulsion device according to an embodiment of the present invention illustrating a variation of the eye drop propulsion device of FIG. 28 having a retractable retractor assembly and a loading button. This embodiment includes a loading button 63 and preferably a loading button spring configures to bias the loading button away from the device. It should be noted that the loading button may be configured to be sufficiently biased away from the device without use of a loading button spring in certain embodiments. The loading button 63 is preferably oriented at a top position with respect to the housing 64, but may be positioned otherwise. A movable arm 132 with movable arm extensions 190 rotate on movable arm axle 196 toward the stationary handle 130 with a handle spring 214, preferably a torsion spring, exerting rotational force away from the stationary handle 130. The eye-port cover 50 rotates on eye-port cover axle 198 with a cap spring 136, preferably a torsion spring, exerting rotational force to rotate the occlusion cap 54 towards the dispenser aperture 34. The cap is preferably made of a compressible rubber, and it protrudes inwards slightly from the eye-port cover 50 such that it exerts sufficient pressure against the dispenser aperture 34, but without excessive pressure to impair rotation of the cover 50. The bottle-port 24 is positioned at an angle so that it is not necessary to invert the eye drop bottle 40 while loading. Note that the specific angle of the eye drop bottle 40 is not particularly important, so long as it is generally downwards, sufficiently aligned with gravity that liquid within the eye drop bottle is concentrated at the nozzle. Referring more specifically to FIGS. 31B and 31C, which show a cutaway view, the loading button 63 is connected to the upper compressor 62. The compression chamber 20 is connected to the bottle-port 24, and may be curved or otherwise aligned depending on the angle of the eye drop bottle to facilitate connection. The dispenser aperture 34 of the dispenser 30 is occluded by the occlusion cap 54. The lower compressor 62' rotates slightly on compressor axle 216, which articulates with the movable arm extension 190. FIG. 31C shows a see-through view of the articulation of the lower compressor 62' with the movable arm extension 190 and compressor axle 216.

Figure 32C:
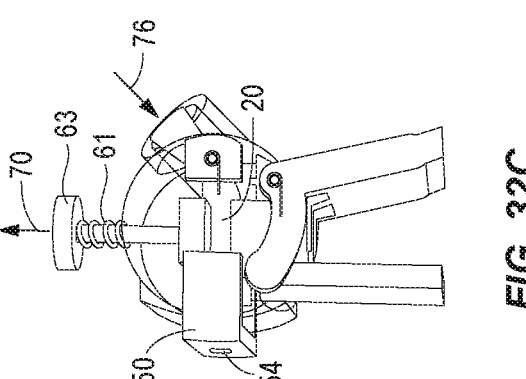
FIGS. 32A-32F show the operation of the eye drop propulsion device of FIG. 31.
Figure 32F:
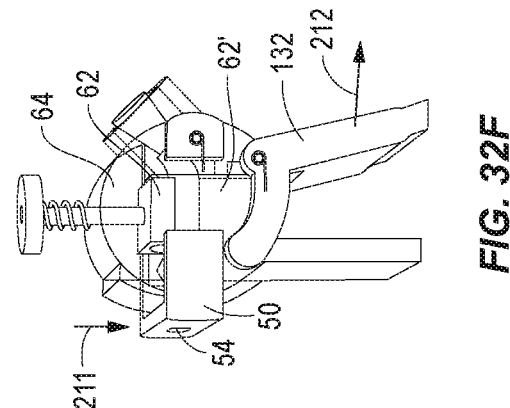
Figure 32B:
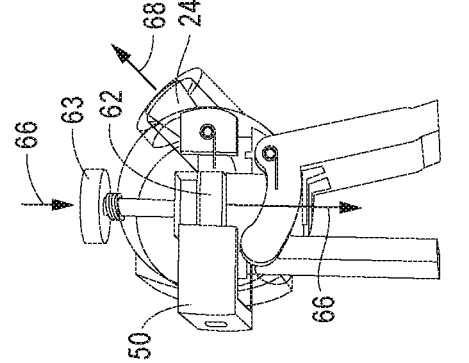
Figure 32E:
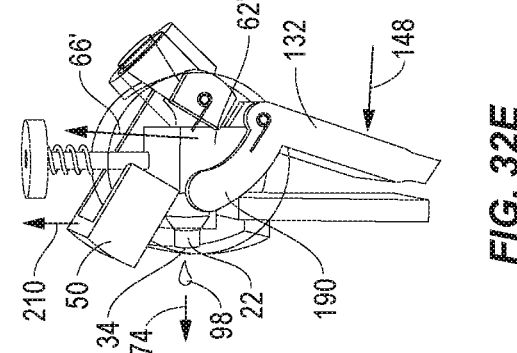
Figure 32A:
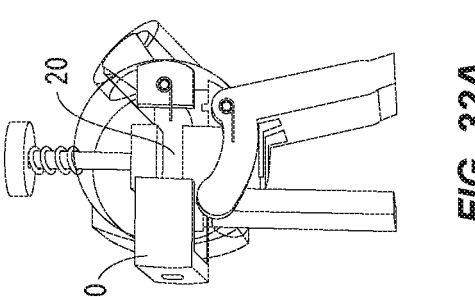
Figure 32D:
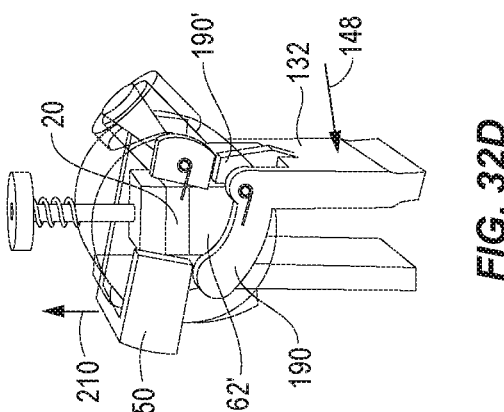

FIGS. 32A-32F show the operation of the eye drop propulsion device of FIG. 31. FIG. 32A shows a cut-away view of the operation of loading the compression chamber 20 with the eye drop propulsion device 10 at rest with the dispenser aperture 34 covered and occluded by the rotational eye-port cover 50 and occlusion cap 54. In FIG. 32B, the loading button 63 is pushed downwards generally in the direction shown by arrow 66. This pushes the upper compressor 62 down, and since the dispenser aperture 34 is occluded by the eye-port cover 50, air is forced through the bottle-port 24 and into the eye drop bottle (not shown) generally in the direction shown by arrow 68. In FIG. 32C, the loading button 63 is released generally in the direction shown by arrow 70, driven by both the elasticity of the compression chamber 20, preferably in this embodiment a silicone tube, and by the compression spring of the loading button spring 61. As noted above, the loading button spring may not be required if the elasticity of the compression chamber 20 is otherwise sufficient to bias the loading button 63. This allows the compression chamber 20 to be deactivated, creating a vacuum in the compression chamber 20, which causes fluid to flow from the eye drop bottle (not shown) into the compression chamber 20, generally in the direction shown by arrow 76. In FIG. 32D, the movable arm 132 is activated (squeezed) towards the stationary handle 130 generally in the direction shown by arrow 148. As it begins its rotation, the movable arm extensions 190 rotate, pushing the rotating eye-port cover 50 upwards generally in the direction shown by arrow 210, which opens the dispenser aperture 34. Even though the dispenser aperture 34 has been opened, the lower compressor 62' is configured so that it does not reach the compression chamber 20 early in the rotation of the eye-port cover 50. In FIG. 32E, the movable arm 190 continues to be squeezed towards the stationary handle 130 generally in the direction shown by arrow 148. The movable arm extensions 190 further rotate the eye-port cover 50 away from the dispenser aperture 34 generally in the direction shown by arrow 210, and the movable arm extension 190 activates the lower compressor 62' generally in the direction shown by arrow 66', which results in the propelling of the drop 98 from the dispenser aperture 34 generally in the direction shown by arrow 74. In FIG. 32F, the movable arm 132 is released generally in the direction shown by arrow 212, which allows the eye-port cover 50 to return to its starting position generally in the direction shown by arrow 211, where it occludes the dispenser aperture 34. It should be noted that the housing 64 may be configured to restrict movement of the compressors 62 and 62', preventing backwards movement when one compressor is pushing against the other on either side of the compression chamber 20.

Figure 33C:
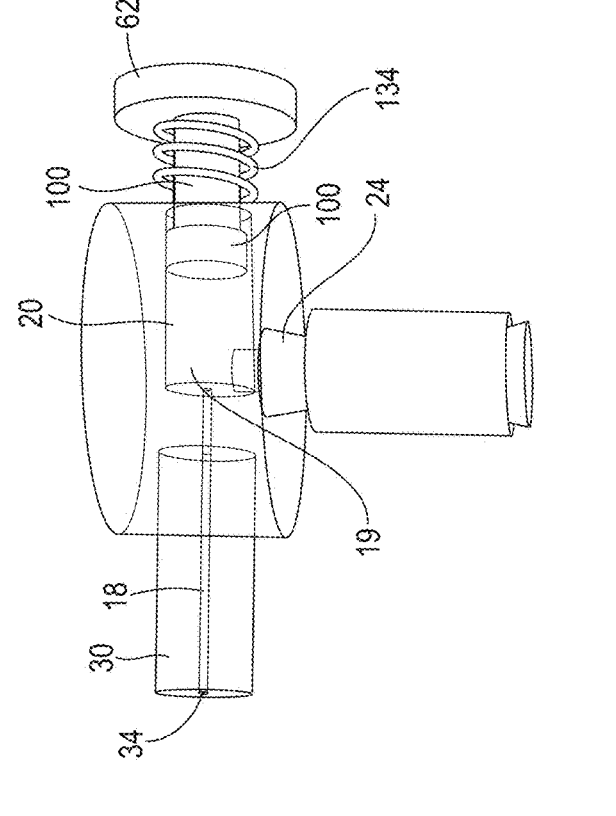
FIGS. 33A-33C show an eye drop propulsion device according to an embodiment of the present invention illustrating a self-occluding option in a horizontal configuration, both with and without a retractable retractor assembly.
Figure 33B:
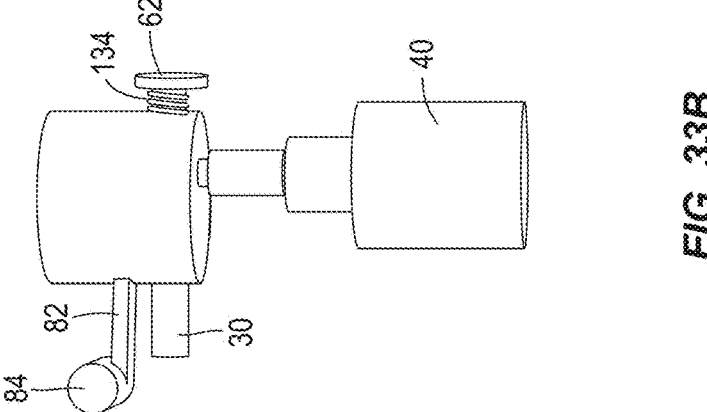
Figure 33A:
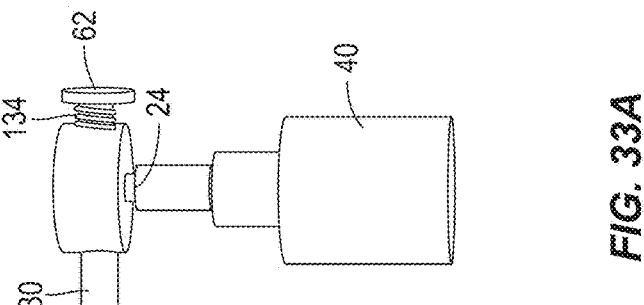

FIGS. 33A-33C show an eye drop propulsion device according to an embodiment of the present invention illustrating a self-occluding option in a horizontal configuration, both with and without a retractable retractor assembly. FIG. 33A shows an embodiment with the compressor 62 opposite the dispenser 30 and the bottle-port 24 oriented beneath the housing 64. FIG. 33B shows an embodiment that includes the retractor assembly 80 having the retractor 82 and the retractor pad 84. FIG. 33C shows a see-through view illustrating that the dispenser may extend inside the housing 64. In alternative embodiments, the dispenser 30 may be partially or fully enclosed within the housing 64, with only the dispenser aperture 34 at or external to the house 64. In this embodiment, the dispenser includes a dispenser tunnel 18 extending from the compression chamber 20 to the dispenser aperture 34. The diameter and length of the dispenser tunnel 18 and its size vis-à-vis the dispenser aperture 34 is dependent on the viscosity of the fluid used in the eye drop propulsion device 10. A smaller dispenser tunnel 18 diameter and elongated length create a significant resistance to the flow of both fluid (as generally detailed under the Hagen-Poiseuille law, which describes how the flow is inversely proportional to the 4th power of the radius of the lumen) and air. This increased resistance has been shown experimentally to act functionally like an eye-port cover 50 and/or occlusion cap 54 to selectively occlude the dispenser aperture 34, preventing or reducing air from entering the compression chamber 20 when the compressor 62 is deactivated, and to allow fluid to be propelled from the dispenser aperture 34 when the compressor is activated. Based on experimentation, when used with viscosity comparable to that in a typical eye drop solution, a dispenser aperture of approximately 0.15 mm in diameter (significantly smaller than the aperture in the nozzle of the eye-drop bottle) and a dispenser tunnel length of approximately 15 mm has been found to provide sufficient occlusion to operate as described herein. In this embodiment the bottle-port 24, eye-port 22, and dispenser tunnel 18 need not join paths before entering compression chamber 20. The compression chamber 20 may act as a reservoir for fluid from the eye drop bottle 40. Alternatively, a fluid cavity (not shown) could be configured between the compression chamber 20 and dispenser 30 to act as a reservoir for fluid used in device operation. The plunger 100 and rubber tip 101 are attached to the compressor 62, and a compressor spring 134 exerts bias of the compressor 62 away from the eye-port 22.

Figure 34C:
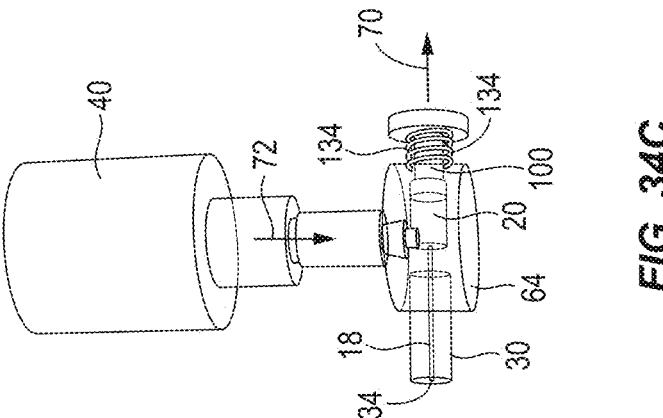
FIGS. 34A-34C show the operation of a variation of the eye drop propulsion device of FIG. 33.
Figure 34B:
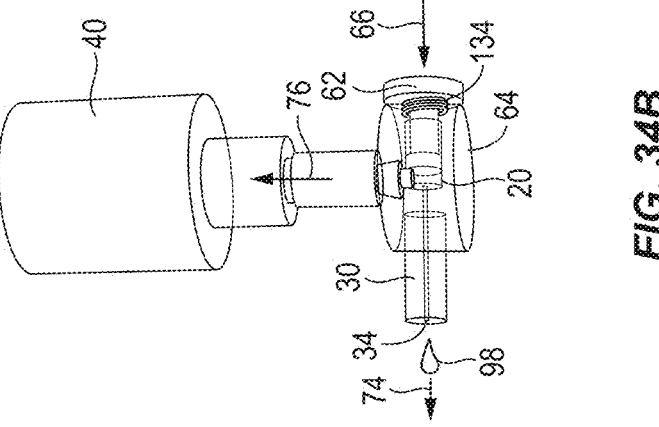
Figure 34A:
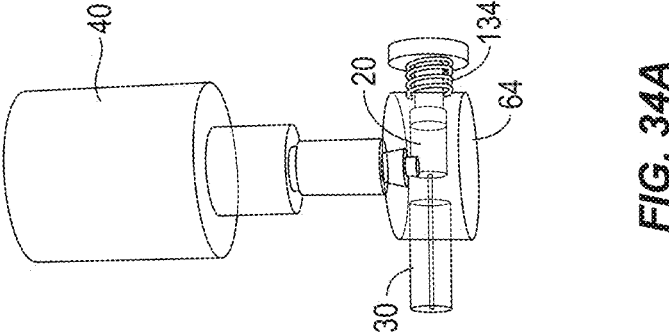

FIGS. 34A-34C show the operation of the eye drop propulsion device of FIG. 33. In FIG. 34A, the eye drop propulsion device 10 and eye drop bottle 40 are shown inverted (sufficiently aligned with gravity that liquid within the eye drop bottle is concentrated at the nozzle) and the compression chamber 20 is already at least partially filled with liquid. In FIG. 34B, the compressor 62 is pressed generally in the direction shown by arrow 66, which moves the plunger 100 into the compression chamber 20. This increases pressure in the compression chamber 20 and the eye-drop bottle 40 and causes the drop 98 of liquid to be propelled through the dispenser tunnel 18 and out through the dispenser aperture 34 generally in the direction shown by arrow 74. As previously noted, this operation may cause some fluid to flow into the eye-drop bottle 40 generally in the direction shown by arrow 76. In FIG. 34C, the compressor spring 134 exerts force to move the plunger 100 out of the compression chamber 20 generally in the direction shown by arrow 70. Since the resistance of the dispenser tunnel 18 functionally occludes the dispenser aperture 34, a vacuum in the compression chamber 20 is created as the plunger 100 is pulled out of the compression chamber 20. This causes fluid from the eye-drop bottle 40 (which has an increased pressure) into the compression chamber 20 generally in the direction shown by arrow 72. The system comes to equilibrium as air percolates in through the dispenser tunnel 18.

FIGS. 35A-35C show an eye drop propulsion device according to an embodiment of the present invention illustrating a self-occluding option in a horizontal configuration, both with and without a retractable retractor assembly. FIG. 35A shows another variation with the compressor 62 oriented vertically and opposite the bottle-port 24, with the eye-port 22 and dispenser 30 oriented horizontally, preferably within the housing 64. FIG. 35B shows an embodiment that includes the retractor assembly 80 having the retractor 82 and the retractor pad 84. FIG. 35C shows a see-through view illustrating that the dispenser may extend inside the housing 64, now oriented vertically and opposite the bottle-port 24. In alternative embodiments, the dispenser 30 may be partially or fully enclosed within the housing 64, with only the dispenser aperture 34 at or external to the house 64. In this embodiment, the dispenser includes a dispenser tunnel 18 extending from the compression chamber 20 to the dispenser aperture 34. The dispenser 30 has the elongated dispenser tunnel 18. The plunger 100 and rubber tip 101 are attached to the compressor 62, and a compressor spring 134 exerts a force on the compressor 62 away from the eye-port 22. As noted above with respect to the horizontal variation, the bottle-port 24, eye-port 22 and dispenser tunnel 18 do not join paths before entering the compression chamber 20 (or in an alternative embodiment a fluid cavity, not shown). Shown in this embodiment is an optional plunger stop 250 configured to prevent the plunger 100 from blocking or otherwise restricting the eye-port 22 or the bottle-port 24.

Figure 36C:
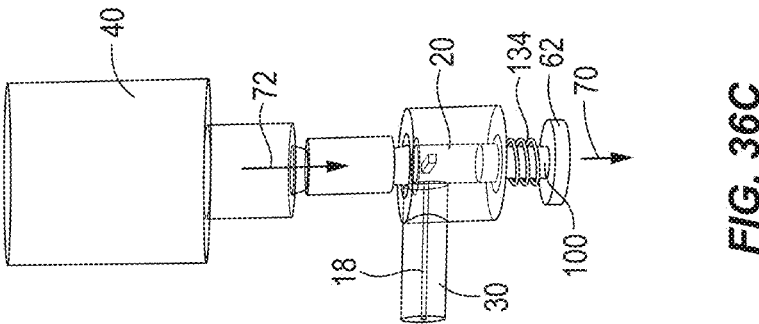
FIGS. 36A-36C show the operation of a variation of the eye drop propulsion device of FIG. 35.
Figure 36B:
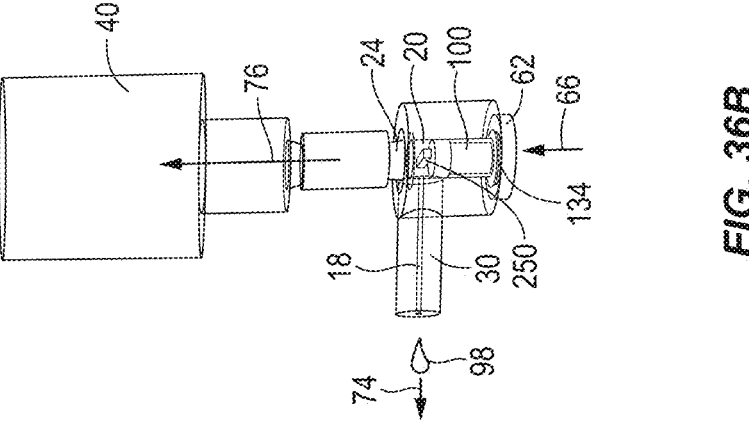
Figure 36A:
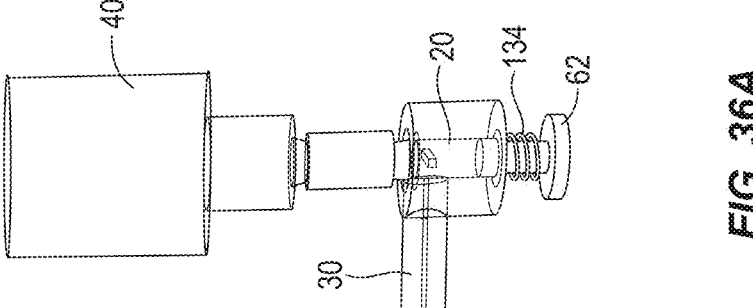

FIGS. 36A-36C show the operation of the eye drop propulsion device of FIG. 35. In FIG. 36A, the eye drop propulsion device 10 and eye drop bottle 40 are shown inverted (sufficiently aligned with gravity that liquid within the eye drop bottle is concentrated at the nozzle) and the compression chamber 20 is already at least partially filled with liquid. In FIG. 36B, the compressor 62 is pressed generally in the direction shown by arrow 66, which moves the plunger 100 into the compression chamber 20. This increases pressure in the compression chamber 20 and the eye-drop bottle 40 and causes the drop 98 of liquid to be propelled through the dispenser tunnel 18 and out through the dispenser aperture 34 generally in the direction shown by arrow 74. As previously noted, this operation may cause some fluid to flow into the eye-drop bottle 40 generally in the direction shown by arrow 76. In this embodiment, the plunger stop 250 stops the plunger from reaching the end of the compression chamber 20, which prevents the plunger 100 from blocking from blocking or otherwise restricting the eye-port 22 or the bottle-port 24. In FIG. 36C, the compressor spring 134 exerts force to move the plunger 100 out of the compression chamber 20 generally in the direction shown by arrow 70. Since the resistance of the dispenser tunnel 18 functionally occludes the dispenser aperture 34, a vacuum in the compression chamber 20 is created as the plunger 100 is pulled out of the compression chamber 20. This causes fluid from the eye-drop bottle 40 (which has an increased pressure) into the compression chamber 20 generally in the direction shown by arrow 72. The system comes to equilibrium as air percolates in through the dispenser tunnel 18.

FIGS. 37A-37E show an embodiment of another configuration with a self-occluding option. FIG. 37A shows the housing 64 supporting the eye drop bottle 40 along with the retractor 82 and retractor pad 84. In this example, the compression chamber 20 is preferably a silicone tube that is slightly curved at the bottle-port 24 to allow for an inclined angle of the eye drop bottle 40 to facilitate liquid contained therein to pool near the bottle-port 24, and an eye-port 22 having a dispenser aperture 34. FIG. 37B shows an enlarged view of the dispenser aperture 34, which in this embodiment is a slit approximately 1 mm in length. Other embodiments could have a very small hole or other geometric shape, and not limited to a single small slit. In this embodiment, the nature of the silicone material causes the dispenser aperture 34 to be occluded or closed when not under pressure, while not occluded or open when under pressure. If the compression chamber is not already filled or "loaded" with fluid, then an initial activation of the compression chamber 20 would be required to fill with liquid, for example by compressing and releasing compressors 62 (in this example, a user's finger or fingers). In such situation, when the compressor 62 is activated or pressed, the dispenser aperture 34 is initially occluded, then as pressure is applied the dispenser aperture 34 is opened and air residing in the compression chamber 20 is forced to flow from the compression chamber into the eye drop bottle 40 (as well as out the dispenser aperture). When the compressor 62 is deactivated or released, the dispenser aperture 34 is again occluded by the silicone material and a vacuum is created in the compression chamber 20 causing a portion of fluid in the eye drop bottle 40 to flow into the compression chamber 20, thereby "loading" the compression chamber.

FIGS. 37C-37E show the operation of this embodiment, in this example with the compression chamber 20 already filled or "loaded" with fluid. In FIG. 37C, the device is supported and aligned towards the eye 86, with the eye drop bottle 40 at a slightly tilted angle. In FIG. 37D, compressor (2) 62, in this case fingers of a user, are used to compress the silicone tube of the compression chamber 20 generally in the direction shown by arrow 66, preferably via a finger positioned above (or on top in the orientation shown) and a thumb positioned below (or on the bottom in the orientation shown). Depending on the degree of pressure applied, use of only a single finger applying pressure against the compression chamber 20 may be required. Pressure from the compressor(s) propel a drop 98 of fluid towards the eye (not shown) generally in the direction shown by arrow 74. In FIG. 37E, the compression chamber 20 is released generally in the direction shown by arrow 70. In this embodiment, the dispenser aperture 34 is occluded by the self-occluding behavior of the silicone material, since it only becomes an actual opening in the silicone when there is positive pressure in the compression chamber forcing it to open. As shown with reference to FIG. 37F, another variation of self-occluding opening is a one way ball valve 264 having a ball 266 constrained near the dispenser aperture 34 by a ball catch 270 and used to unseal a valve aperture 268 when pressure is applied and seal valve aperture 268 when pressure is released, thereby allowing or restrictive the flow of liquid and/or air within the compression chamber 20. Although the embodiment shown and described in FIG. 37 illustrates a single path (2-pole) configuration, the same or similar self-occluding structure readily be applied to a dual path (3-pole) configuration without departing from the scope of the present invention.

Figure 37G:
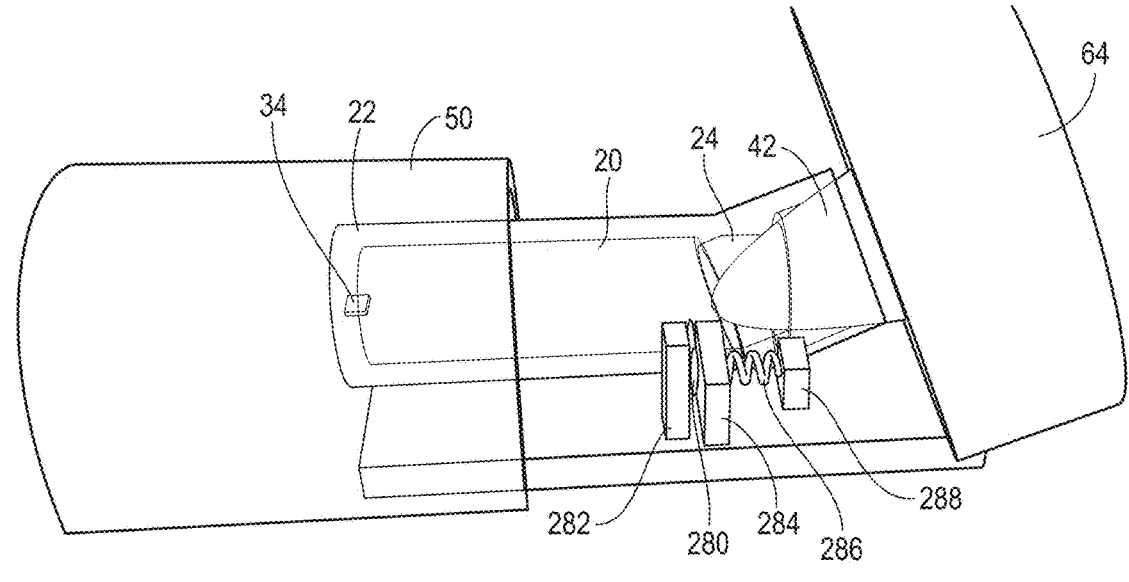
Figure 37H:
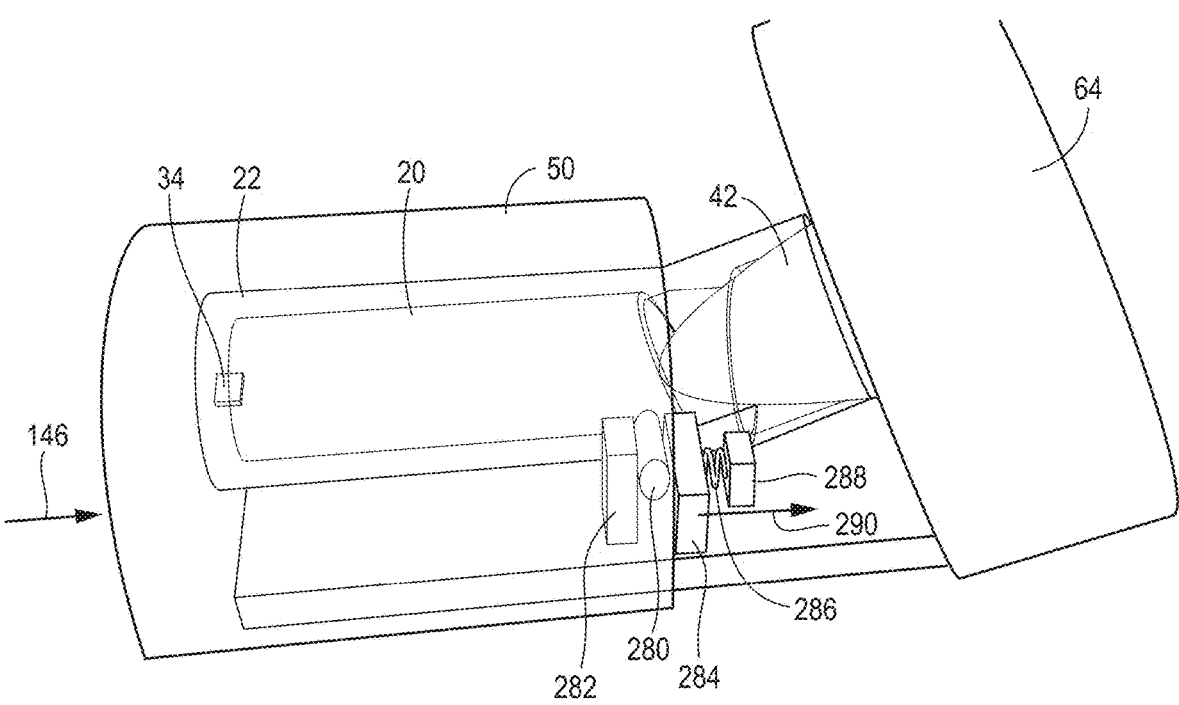

In this embodiment, a vacuum is created in the compression chamber 20 and fluid flows from the eye drop bottle 40 into the compression chamber 20 in the general direction of arrow 72. Experimentation has shown that multiple drops can be dispensed reliably, but a persistent vacuum may eventually develop in the eye drop bottle, which may require the removal of the eye drop bottle to alleviate the vacuum before reengaging the device. Experimentation has also shown that there may be a small flow of air back into the compression chamber 20 through the slit 34, which in turn helps prevent a persistent vacuum, given that a user typically dispenses drops over many days. Other embodiments may include a vacuum release button (not shown), for example activated each time the compression chamber 20 is connected to the eye drop bottle 40 around the nozzle 42, which would make removal of the eye drop bottle to alleviate the vacuum unnecessary. Other embodiments could include a spring loaded vacuum release tunnel in the compression chamber 20 near the bottle-port 24 configured such that it would be closed while the device is in use and would be opened when a cover is applied to the device and eye drop bottle 40. FIGS. 37G and 37H shows one such alternative embodiment of a spring-loaded vacuum release tunnel. In FIG. 37G, the eye-port cover 50 is shown partially placed in preparation of moving to cover the eye-port 22 and at least part of the compression chamber 20. In this embodiment, the eye-port cover 50 may be supported in part by the housing 64. A vacuum release tunnel 280, preferably located near the bottle-port 24, provides external communication into the compression chamber 20 when not occluded to alleviate the vacuum within the eye drop bottle 40. The vacuum release tunnel could alternatively be an aperture in the compression chamber with a cover, lid or the like to keep it occluded when in operation and opened or closed by movement of the cover, compressor, retractor, or separate actuator. It could also be a self-occluding slit opened by application of the cover or by movement of the compressor. As shown in FIG. 37G, when in operation (when the eye-port cover 50 is not fully in place and/or the eye drop propulsion device 10 is in operation), the vacuum release tunnel 280 is occluded, in this example by being pinched or squeezed between a compressor stop 282 and a tunnel compressor 284, which is movably connected to a compressor spring 286 held in place by a compressor spring mount 288. In this position the compressor spring 286 exerts force against the tunnel compressor 284, pushing it against the compressor stop 282, thereby occluding the vacuum release tunnel. The compressor spring mount may be separate from or an integrated component of the housing 64. In FIG. 37H, as the eye-port cover 50 is moved into place to cover the eye-port 22 generally in the direction shown by arrow 146, the eye-port cover 50 forces the compressor spring 286 away from the compressor stop 282 generally in the direction shown by arrow 290, thereby removing pressure from and opening the vacuum release tunnel 280, which alleviates vacuum within the eye drop bottle 40.

FIGS. 38A-38I show a variation the present invention that does not need a selectively occludable eye-port 22, dispenser aperture 34, or a vacuum to be created in the compression chamber 20. Instead, it relies on the configuration of the compression chamber, namely, the relative position of the nozzle 42 of the eye drop bottle 40 to the dispenser aperture 34 of the eye-port 22. In this embodiment, there is sufficient space within the compression chamber or reservoir to allow liquid to flow in from the nozzle and be retained away from the nozzle to ensure that liquid is not drawn back into the eye drop bottle due to change in pressure within the compression chamber or reservoir. Also in this embodiment, the dispenser aperture of the eye-port is positioned above the liquid fill level during filling but below the liquid fill level when at least a drop of the liquid is propelled via the dispenser aperture. In this embodiment, to move liquid from the eye drop bottle 40 into the compression chamber 20 or reservoir, the nozzle 42 is pointed generally downwards (sufficiently aligned with gravity that liquid within the eye drop bottle is concentrated at the nozzle) to position the dispenser aperture below the liquid fill level.

Figures 38A, 38B, 38C, 38D, 38E, 38F, 38G, 38H, 38I:
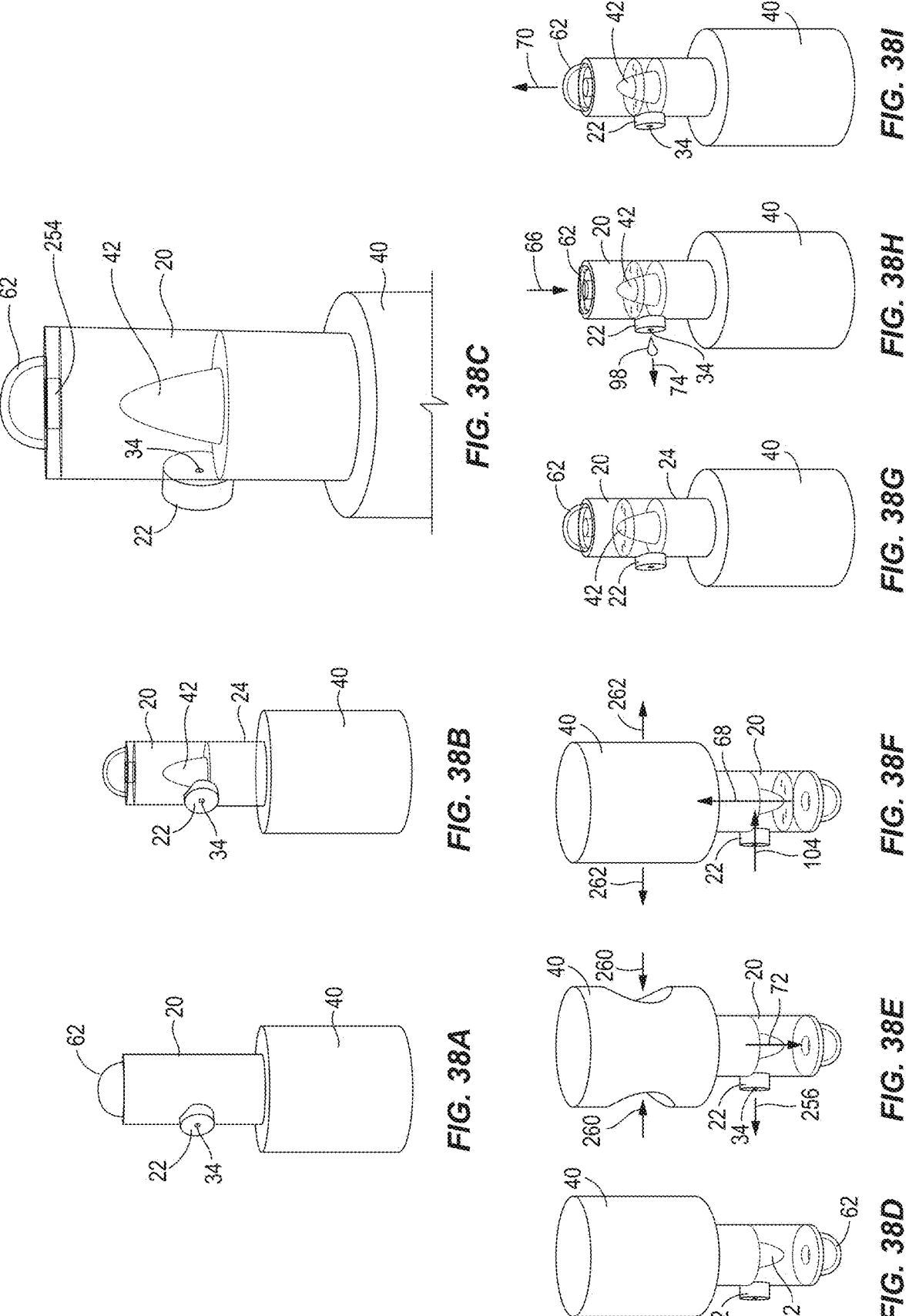
FIGS. 38A-38I show a variation the present invention that does not utilize a selectively occludable dispenser aperture.

FIG. 38A illustrates the compression chamber 20, the eye-port 22, the eye drop bottle 40, and the compressor 62. Referring to FIG. 38B and the enlargement in FIG. 38C (a see-through view of the compression chamber 20), the eye drop bottle 40 is secured to the bottle-port 24, preferably in a watertight fashion, with the nozzle 42 extending into the compression chamber 20 such that fluid in the compression chamber 20 can flow freely to reach the dispenser aperture 34 when the device is in an operable (preferably upright) orientation. In this embodiment, the compressor 62 is preferably a hollow, compressible silicone dome connected via a compression conduit 254 of the compression chamber 20. FIGS. 38D-38I show a preferred operation of this embodiment. In FIG. 38D, the device and the eye drop bottle 40 are inverted or at least aligned such that the nozzle 42 is pointed generally downwards (sufficiently aligned with gravity that liquid within the eye drop bottle is concentrated at the nozzle). In FIG. 38E, an eye drop bottle compressor(s) (not shown) (in this example fingers of a user, preferably a finger and a thumb positioned on either side of the eye drop bottle) are activated to compress the eye drop bottle 40 generally in the direction shown by arrow 260, which forces liquid into the compression chamber 20 in the general direction of arrow 72. Fluid can readily flow into to compression chamber 20 since the dispenser aperture 34 is open and air flows out of the compression chamber through the eye-port 22 generally in the direction shown by arrow 256. In this orientation, fluid from the nozzle 42 will fall towards the bottom of the inverted compression chamber 20 generally in the direction shown by arrow 72, away from the nozzle 42. Fluid will not come out of the dispenser aperture 34 since in this orientation it is positioned towards the top of the inverted compression chamber 20. In FIG. 38F, the eye drop bottle compressor(s) (not shown) are deactivated, removing pressure against the eye drop bottle 40, generally in the direction shown by arrows 262, resulting in air flowing into compression chamber 20 through the dispenser aperture 34 generally in the direction shown by arrow 104, and into the eye drop bottle generally in the direction shown by arrow 68. If more liquid than is needed for the application was moved out of the eye drop bottle 40 into the compression chamber 20, the excess fluid is drawn back into the eye drop bottle 40, maintaining the fluid level in the compression chamber 20 at approximately the height of the top (depending on the orientation) of the opening of the nozzle 42, which helps to ensure that the compression chamber 20 is not overfilled. In FIG. 38G, the device is turned upright, or at least aligned such that the liquid in the compression chamber 20 is at a sufficient level to allow a drop of desired size to flow via the eye-port 22 through the dispenser aperture 34, and the fluid in the compression chamber 20 flows to the bottom (depending on the orientation) of the compression well 252 towards the nozzle 42, at this point adjacent the eye-port 24 and dispenser aperture 34. In FIG. 38H, the compressor 62 is activated or pressed generally in the direction shown by arrow 66, which propels a drop 98 towards the eye (not shown) generally in the direction shown by arrow 74. In this embodiment, the volume inside the compressor 62 determines the size of the drop. Because the volume of liquid in the compression well 252 is significantly larger than the volume of liquid inside the compressor 62, it is possible to dispense several drops without having to invert the bottle to "reload" the compression chamber 20. In FIG. 38I, the compressor 62 is released generally in the direction shown by arrow 70, and the system returns to equilibrium. Although this embodiment is shown and described having a plastic compression chamber 20 and a silicone compressor 62, other embodiments may utilize a silicone compression chamber and a silicone compressor all made as a single piece, or utilize other materials having similar characteristics, which may have production benefits.

Figure 39B:
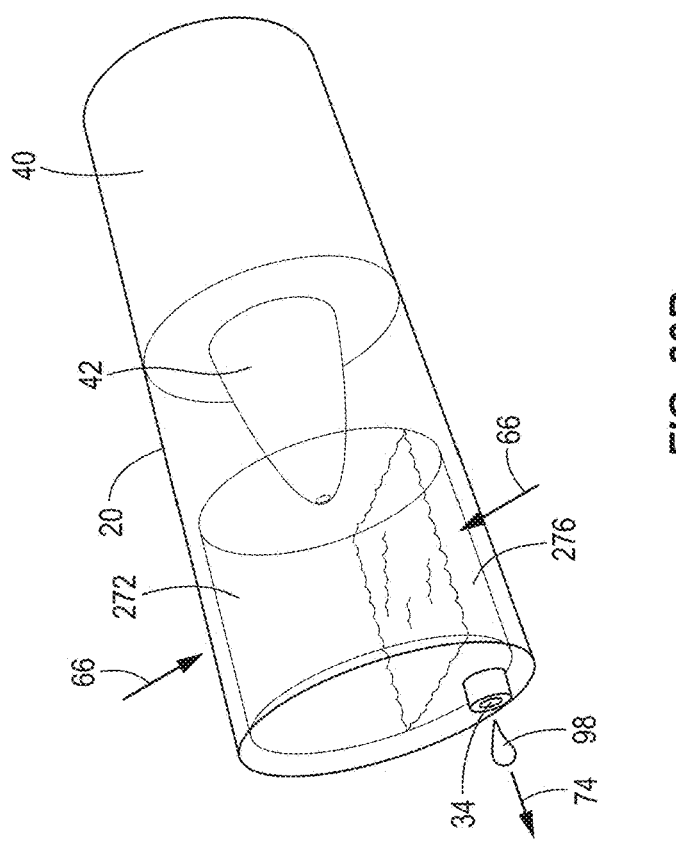
FIGS. 39A-39B show a variation of the eye drop propulsion device of FIG. 37.
Figure 39A:
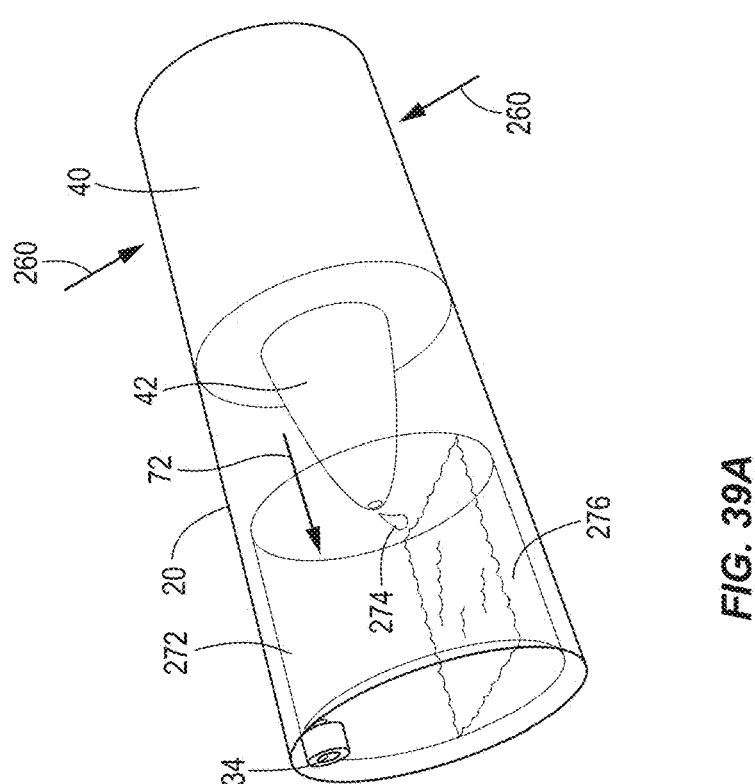

In an alternative configuration of the embodiment shown in FIG. 38, illustrated in FIGS. 39A-39B, the compression chamber 20 is shown as made entirely from malleable silicone. In this example, the eye-port 22 and dispenser aperture 34 are positioned such that they are isolated from the nozzle 42 when a loading drop 274 of loading liquid 276 is forced into the compression chamber 20 or, as shown here, a separate liquid reservoir 272 in communication with both the nozzle 42 and the eye-port 22. FIG. 39A shows the loading drop 274 joining existing loading liquid 276 in the reservoir 272 while the eye-port 22 and dispenser aperture 34 is positioned above the liquid fill level when the eye drop bottle compressor(s) (not shown) (in this example fingers of a user, preferably a finger and a thumb positioned on either side of the eye drop bottle) are activated to compress the eye drop bottle 40 generally in the direction shown by arrow 260, which forces liquid into the compression chamber 20 (or in this case the reservoir 272) in the general direction of arrow 72. FIG. 39B shows the eye-port 22 and dispenser aperture 34 positioned below the liquid fill level when the compressor 62 is activated (in this example fingers of a user, preferably a finger and a thumb positioned on either side of the compression chamber 20) or pressed generally in the direction shown by arrow 66, which propels a drop 98 towards the eye (not shown) generally in the direction shown by arrow 74.

Many variations of the described embodiments are possible without departing from the unique principles of the present invention. A multitude of mechanisms to obstruct the outflow and inflow are possible. There are a multitude of methods to attach the cover to obstruct the dispenser aperture, such as a snap or hinged cover. The eye-port cover or occlusion cap described herein are only a few of the occlusion configurations that may be used to achieve the functionality of the present invention. Instead of an eye-port cover or occlusion cap located exterior to the dispenser or compression chamber eye-port, the dispenser aperture could be occluded internally, for example by closing or otherwise obstructing the dispenser aperture at the exit, along the length or at an end of the dispenser aperture closest to the compression chamber. An obstruction or restriction of the flow of air and/or liquid at any point between within or between the compression chamber and the dispenser aperture may likewise be used, for example via a clamp or other restriction structure. As describe above, depending on the viscosity of the fluid used in a particular application, a restriction in the size, length or other configuration of the dispenser aperture or eye-port path extension may sufficiently occlude the dispenser aperture without the need for a separate structural member used for obstruction. In yet another example, mechanical levers can close the inflow and outflow. Obstructing ball valves that automatically move the balls depending on the position of the bottle are possible. One such variation would be a ball in the compressing chamber such that in the inverted position, the ball would sink and obstruct the outflow from the eye-port, and in the upright position, the ball would obstruct outflow through the bottle-port.

As noted above, various configurations of compressing chambers are possible other than a tube, such as a flat circular disc that can be fit into the lid. Thin, silicone channels that can easily be compressed can be incorporated into the walls of the compressing chamber. Springs around the compressing chamber can increase the vacuum and the volume of fluid drawn into the compressing chamber. A multitude of materials of differing hardness and elasticity can vary the force and volume. A multitude of shapes and sizes can influence the performance. Additionally, different directions of propulsion could be advantageous, such as the propulsion being at a right angle to the bottle, helping with the ergonomics. An extremely simple embodiment would be one where compressor is just the patient's finger, and the compressing chamber itself is the housing.

Another embodiment would be to retract the lid with a finger instead of a separate member. An alternative embodiment may include a structure to support and position the device that provides an opening to allow a user's finder to retract the lower eyelid. Another embodiment could include a supporting structure rather than a retracting structure; this would encircle the eye, or rest on the brow and cheek, to position and support the EDPD without retracting the lid. Another embodiment could allow support to aim the eye-port at an oblique angle from the side rather than directed directly in front. Another variation would be to have a support ring that the patient would center by looking straight into the target, and simply look up before the drop is dispensed to get the drop to hit the lower conjunctiva. Still another embodiment might include a motorized compression of the compression chamber or eye-port occlusion. Also, variations of the compressor assembly 60 and compressor 62 would allow mechanical advantage to make it so that less force would be needed to compress the compression chamber. Other embodiments might include a means to fully occlude the bottle-port rather than relying on the small aperture inside the nozzle of the eye drop bottle to impede the backflow; this would improve the efficiency and volume of the eye drop.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. An eye drop propulsion device for propelling a drop of fluid towards an eye for use with an eye drop bottle having a nozzle, comprising:

a compression chamber having a nozzle end configured to connect to the eye drop bottle to allow for communication of fluid from the nozzle of the eye drop bottle to the compression chamber; and a dispenser aperture configured to be selectively occluded or not occluded, wherein when the compression chamber is first activated when the dispenser aperture is occluded, air is forced to flow from the compression chamber into the eye drop bottle, and when the compression chamber is deactivated, a portion of fluid in the eye drop bottle flows into the compression chamber; and when the compression chamber is second activated when the dispenser aperture is not occluded, a drop of fluid is propelled towards the eye.

2. The propulsion device of claim 1, further comprising a reservoir connected to the compression chamber and configured to retain fluid and communicate that fluid towards the dispenser aperture.

3. The propulsion device of claim 1, wherein the eye drop bottle is oriented such that it is inverted before the compression chamber is deactivated when the dispenser aperture is occluded.

4. The propulsion device of claim 1, wherein the compression chamber is configured to connect to the eye drop bottle without the use of a valve between the compression chamber and the eye drop bottle.

5. The propulsion device of claim 1, wherein the dispenser aperture is selectively occluded or not occluded downstream of the compression chamber.

6. The propulsion device of claim 1, wherein the drop is propelled towards the eye without the aid of gravity.

7. The propulsion device of claim 1, further comprising a cover configured to selectively occlude the dispenser aperture.

8. The propulsion device of claim 1, further comprising a retractor configured to support the propulsion device aligned with the eye before the drop of the fluid is propelled towards the eye.

9. The propulsion device of claim 1, further comprising a retractor configured to retract a lower lid of the eye before the drop of the fluid is propelled towards the eye.

10. The propulsion device of claim 1, wherein the drop of fluid is propelled towards the eye with sufficient velocity to reach the eye.

11. The propulsion device of claim 1, wherein at least one of the compression chamber and dispenser aperture are sized to allow the drop of fluid to be propelled.

* * * * *